(12) United States Patent
Makower et al.

(10) Patent No.: US 10,589,009 B2
(45) Date of Patent: *Mar. 17, 2020

(54) BREAST PUMP SYSTEM AND METHODS

(71) Applicant: EXPLORAMED NC7, INC., Mountain View, CA (US)

(72) Inventors: Joshua Makower, Los Altos Hills, CA (US); John Y Chang, Los Altos, CA (US); Michele Torosis, Los Altos, CA (US); Michael Landry, Austin, TX (US); Earl Bright, II, Los Altos, CA (US); Alan W Cannon, Union City, CA (US)

(73) Assignee: ExploraMed NC7, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/362,920

(22) Filed: Nov. 29, 2016

(65) Prior Publication Data

US 2017/0072118 A1    Mar. 16, 2017

Related U.S. Application Data

(63) Continuation of application No. PCT/US2015/041277, filed on Jul. 21, 2015.

(60) Provisional application No. 62/053,095, filed on Sep. 19, 2014, provisional application No. 62/027,685, filed on Jul. 22, 2014.

(51) Int. Cl.
*A61M 1/06* (2006.01)
*A61J 13/00* (2006.01)

(52) U.S. Cl.
CPC .............. *A61M 1/062* (2014.02); *A61M 1/06* (2013.01); *A61J 13/00* (2013.01); *A61M 2205/3334* (2013.01); *A61M 2205/50* (2013.01)

(58) Field of Classification Search
CPC ........ A61M 1/06; A61M 1/062; A61M 1/064; A61M 1/066; A61M 1/068; A61M 2210/1007; A61B 2018/00333; A61J 13/00

See application file for complete search history.

(56) References Cited

U.S. PATENT DOCUMENTS

| 1,197,011 A | 9/1916 | Cilino |
| 4,263,912 A | 4/1981 | Adams |

(Continued)

FOREIGN PATENT DOCUMENTS

| CN | 2628060 Y | 7/2004 |
| EP | 2456482 B1 | 11/2016 |

(Continued)

OTHER PUBLICATIONS

Chiu et a., Development of a piezoelectric polyvinylidene fluoride (PVDF) polymer based sensor patch for simultaneous heartbeat and respiration monitoring, Sensors and Actuators A: Physical, vol. 189, Jan. 15, 2013, pp. 328-334.

(Continued)

*Primary Examiner* — Bhisma Mehta
*Assistant Examiner* — William R Frehe

(57) ABSTRACT

Systems and methods for pumping milk from a breast, wherein the milk is expressed from the breast under suction and milk is expulsed from the pumping mechanism to a collection container under positive pressure.

28 Claims, 30 Drawing Sheets

(56) References Cited

U.S. PATENT DOCUMENTS

| | | | |
|---|---|---|---|
| 4,311,141 A | 1/1982 | Diamond | |
| 4,768,547 A * | 9/1988 | Danby | A61M 5/14224 |
| | | | 137/454.4 |
| 5,542,921 A | 8/1996 | Meyers et al. | |
| 5,634,468 A | 6/1997 | Platt et al. | |
| 5,827,191 A | 10/1998 | Rosenfeld | |
| 6,273,868 B1 | 8/2001 | Nordvik | |
| 6,287,252 B1 | 9/2001 | Lugo | |
| 6,328,082 B1 | 12/2001 | Lafond | |
| D459,233 S | 6/2002 | Young | |
| 6,440,100 B1 | 8/2002 | Prentiss | |
| 6,547,756 B1 | 4/2003 | Greter et al. | |
| 6,579,258 B1 * | 6/2003 | Atkin | A61M 1/066 |
| | | | 604/74 |
| 6,712,785 B2 | 3/2004 | Morton et al. | |
| 7,201,735 B2 | 4/2007 | Atkin et al. | |
| 7,223,255 B2 | 5/2007 | Myers et al. | |
| 7,621,797 B1 | 11/2009 | Hershkovich | |
| 7,824,363 B2 | 11/2010 | Myers | |
| 7,988,661 B2 | 8/2011 | Silver et al. | |
| 8,057,425 B1 | 11/2011 | Myers et al. | |
| 8,070,715 B2 | 12/2011 | Quackenbush et al. | |
| 8,070,716 B2 | 12/2011 | Sutrina et al. | |
| 8,262,606 B2 | 9/2012 | Greter et al. | |
| 8,282,596 B2 | 10/2012 | Greter et al. | |
| 8,353,865 B2 | 1/2013 | Thilwind et al. | |
| 8,376,986 B2 | 2/2013 | Van Schijndel et al. | |
| 8,671,701 B2 | 3/2014 | McKendry | |
| 8,684,961 B2 | 4/2014 | Gottenbos et al. | |
| 8,801,495 B1 | 8/2014 | Guindon | |
| 9,050,404 B2 | 6/2015 | Silver et al. | |
| 9,162,016 B2 | 10/2015 | Geddes | |
| 9,173,587 B2 | 11/2015 | Van Schijndel et al. | |
| 9,199,017 B2 | 12/2015 | Greter | |
| 9,278,167 B2 | 3/2016 | Aalders et al. | |
| 10,398,816 B2 * | 9/2019 | Chang | A61M 1/06 |
| 2003/0191433 A1 | 10/2003 | Prentiss | |
| 2004/0024351 A1 | 2/2004 | Greter et al. | |
| 2004/0101414 A1 | 5/2004 | Gharib et al. | |
| 2004/0127845 A1 * | 7/2004 | Renz | A45C 3/06 |
| | | | 604/74 |
| 2005/0059928 A1 | 3/2005 | Larsson | |
| 2005/0131332 A1 | 6/2005 | Kelly et al. | |
| 2005/0234370 A1 | 10/2005 | Beal et al. | |
| 2006/0106334 A1 | 5/2006 | Jordan et al. | |
| 2008/0045888 A1 | 2/2008 | Edwards et al. | |
| 2008/0177224 A1 * | 7/2008 | Kelly | A61M 1/0037 |
| | | | 604/74 |
| 2008/0243059 A1 * | 10/2008 | Yamashita | A61M 1/06 |
| | | | 604/74 |
| 2009/0024080 A1 | 1/2009 | Rohrig | |
| 2010/0217148 A1 | 8/2010 | Binder | |
| 2011/0071466 A1 | 3/2011 | Silver et al. | |
| 2011/0196291 A1 | 8/2011 | Vischer et al. | |
| 2011/0245763 A1 | 10/2011 | Myers | |
| 2012/0101575 A1 | 4/2012 | Horne et al. | |
| 2012/0277636 A1 | 11/2012 | Blondheim et al. | |
| 2012/0277728 A1 | 11/2012 | Weber et al. | |
| 2013/0023821 A1 * | 1/2013 | Khalil | A61M 1/064 |
| | | | 604/74 |
| 2013/0123688 A1 | 5/2013 | Bosman et al. | |
| 2013/0131588 A1 | 5/2013 | Silver et al. | |
| 2013/0177455 A1 | 7/2013 | Kamen et al. | |
| 2014/0066734 A1 | 3/2014 | Zdeblick | |
| 2014/0330200 A1 * | 11/2014 | Scheidegger | A61M 1/06 |
| | | | 604/74 |
| 2015/0100016 A1 | 4/2015 | Liao | |
| 2015/0292500 A1 | 10/2015 | Girard et al. | |
| 2016/0256618 A1 | 9/2016 | Embleton | |

FOREIGN PATENT DOCUMENTS

| | | |
|---|---|---|
| EP | 3151876 B1 | 11/2017 |
| GB | 2342446 A | 4/2000 |
| JP | 2005279044 | 10/2005 |
| RU | 2012 107356 | 5/2012 |
| WO | WO 2000/57934 | 10/2000 |
| WO | WO2001054488 | 8/2001 |
| WO | WO2011010255 | 1/2011 |
| WO | WO2011144984 A | 11/2011 |
| WO | WO2012037848 | 3/2012 |
| WO | WO 2013/076055 | 5/2013 |
| WO | WO 2013076055 | 5/2013 |
| WO | WO 2013166462 | 5/2013 |
| WO | WO2013088310 | 6/2013 |
| WO | WO 2013/187763 | 12/2013 |
| WO | WO2013184004 | 12/2013 |
| WO | WO2015120321 | 8/2015 |

OTHER PUBLICATIONS

Double Electric Breast Pump/Dr. Brown's, http://www.drbrownsbaby.com/breastfeeding-product/breast-pumps/double-electric, May 15, 2014.

* cited by examiner

FIG. 13C  FIG. 13D

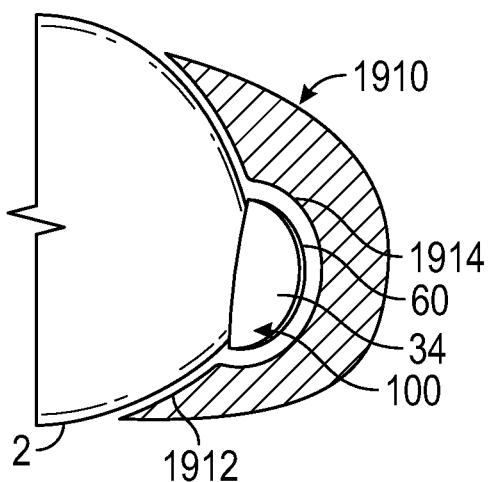
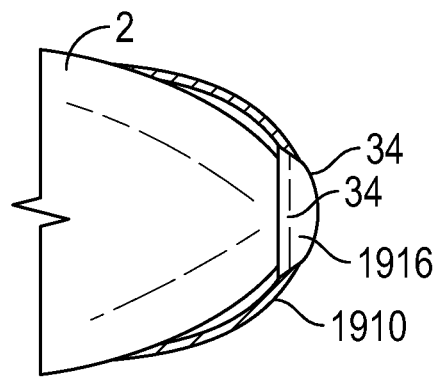
FIG. 19C
FIG. 19D
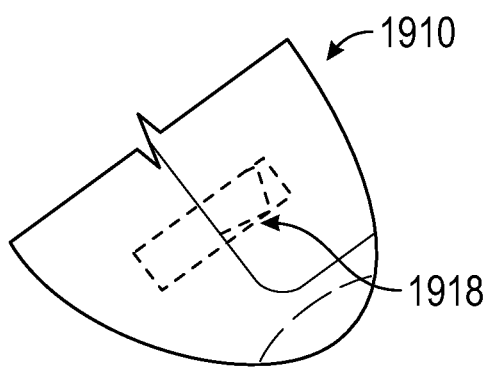
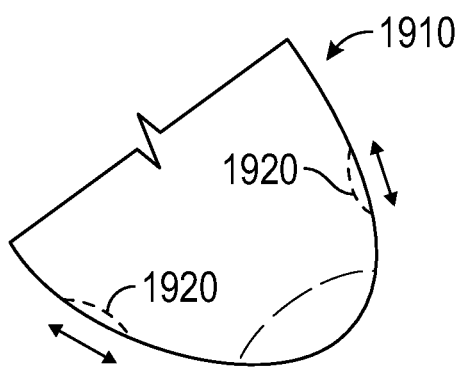
FIG. 19E
FIG. 19F
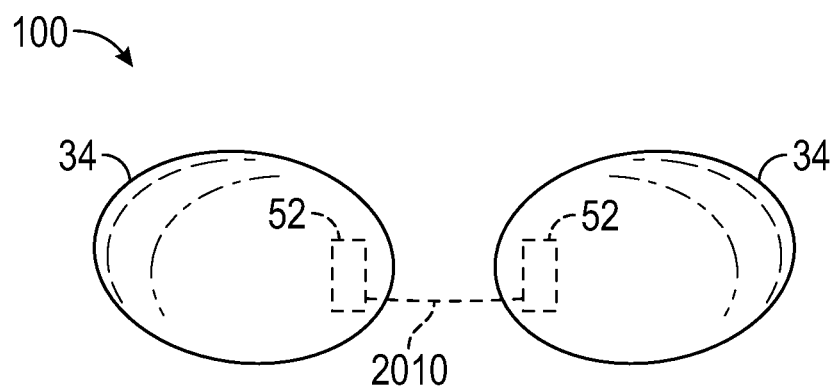
FIG. 20

BREAST PUMP SYSTEM AND METHODS

FIELD OF THE DISCLOSURE

The present disclosure generally relates to portable, energy efficient breast pump systems and methods for collecting milk from a breast of a nursing mother.

BACKGROUND OF THE DISCLOSURE

As more women become aware that breastfeeding is the best source of nutrition for a baby, and also offers health benefits to the nursing mother, the need is increasing for breast pump solutions that are user-friendly, quiet, discrete and versatile for use by a nursing mother in various situations. This is particularly true for the working mother, who is away from the home for eight to ten hours or more and needs to pump breast milk in order to have it available for her baby, but it is also a requirement for many other situations where the mother is away from the privacy of the home for an extended period, such as during shopping, going out to dinner or other activities.

Although a variety of breast pumps are available, most are awkward and cumbersome, requiring many parts and assemblies and being difficult to transport. Hand pump varieties that are manually driven are onerous to use and can be painful to use. Some powered breast pumps require an AC power source to plug into during use. Some systems are battery driven, but draw down the battery power fairly rapidly as the motorized pump continuously operates to maintain suction during the milk extraction process. Many of the breast pumps available are clearly visible to an observer when the mother is using it, and many also expose the breast of the mother during use.

There is a continuing need for a small, portable, self-powered, energy efficient, wearable breast pump system that is easy to use and is discrete by not exposing the breast of the user and being invisible or nearly unnoticeable when worn.

SUMMARY OF THE DISCLOSURE

Briefly and in general terms, the present disclosure is directed towards breast pump systems and methods. The system can include breast contacting structure, a storage container and structure that facilitates transfer of extracted mild from the breast to the storage container. The method can involve pumping milk from a breast and delivering mild to the storage container. In one particular approach, a controller is further provided which controls the breast pump, and in one embodiment, controls the pumping of milk from a plurality of breast pumps.

According to one aspect of the present disclosure, a system for pumping milk from a breast can included a skin contact member configured to form a seal with the breast. The system can additionally or alternatively include one or more of a conduit in fluid communication with and connected to the skin contact member and a driving mechanism configured to compress a first region of the conduit, wherein the first region in the conduit has a first cross-sectional area, wherein a second region of the conduit has a second cross-sectional area, wherein a third region of the conduit has a third cross-sectional area, and wherein the first cross-sectional area is larger than the second cross-sectional area and larger than the third cross-sectional area.

In various of the disclosed embodiments, the system defines a natural breast profile. The natural breast profile is contemplated to fit comfortably and conveniently into a bra of a user and to present a natural look. As such, the profile is characterized by having a non-circular base. Moreover, like natural breasts, the profile of the device or system is contemplated to define one or more asymmetric curves and off-center inertial centers.

In at least one embodiment, the skin contact member, the conduit and the driving mechanism are contained within a main body that is configured to be attached to the breast and supported by a bra. The system can further include a one-way valve attached to a proximal end of the conduit and a storage container for storing the milk pumped from the breast. The system can also further include a one-way valve attached to a proximal end of the conduit and configured to attach to the storage container to place the conduit in fluid communication with the storage container.

A driving mechanism can be provided and be further configured to retract away from the first region of the conduit, and wherein a suction created by compressing the first region of the conduit and allowing the first region of the conduit to rebound is a driving force for extracting milk from the breast.

In at least one embodiment, the conduit, the driving mechanism and the controller are contained within a main body, the system further including controls on the main body that are operable by a user to select or modify at least one of: pumping mode, frequency of pumping cycle, maximum suction pressure achieved during a pumping cycle, latch suction pressure achieved during the pumping cycle, pumping force and pumping session time. The skin contact member may be incorporated in the main body, the main body being configured to be attached to the breast and supported by a bra. In at least one embodiment, the main body is connected to the skin contact member via a second conduit.

In at least one embodiment, the driving mechanism and the controller are contained within a main body, the system further including one or more of: an external computer external of the main body; the controller being configured to send signals to and receive signals from the external computer. The controller can include a wireless transmitter and wireless receiver for wirelessly sending the signal to and receiving the signals from the external computer. The external computer can also include a processor and instructions, which when executed, cause the processor to: customize pump functions based on the signals received from the controller; and send the customized pump functions to the controller. Further, the external computer includes a processor and instructions, which when executed, cause the processor to: calculate volume of milk extracted, to track expression efficiency and monitor it over time, based on the signals received from the controller. Additionally, the external computer can include a processor and instructions, which when executed, cause the processor to track of inventory of previous pumping sessions, including tracking at least one of: dates of the previous pumping sessions, volumes pumped in the previous pumping sessions, and specific tracking numbers for specific milk collection containers into which milk has been pumped in the previous pumping sessions. Alternatively or additionally, the external computer can send the customized pump functions to the controller in real time, during a pumping session.

The main body is contemplated to include a battery electrically connected to the controller and the pumping mechanism, and the external computer includes a processor and instructions, which when executed, cause the processor to one or more of: monitor remaining battery power of the battery and output a warning when the battery reaches a predetermined low level of charge. The customized pump functions include modifications to at least one of: maximum suction pressure level, latch suction pressure level, suction pressure waveform over a pumping cycle, phases of extraction or feeding times, rest times, heating temperatures and times, vibration frequency and duration, and pumping session time.

In at least one embodiment, the external computer includes a display, and a processor and instructions, which when executed, cause the processor to: display one or more photos of a user's baby during a pumping session.

In at least one embodiment, the external computer includes a processor and instructions, which when executed, cause the processor to: compile a histogram, using signals received from the controller; and display the histogram on a display of the external computer.

In at least one embodiment, the external computer is further configured to receive inputs from a user when the user uses an input feature of the external computer; wherein the external computer includes a processor and instructions, which when executed, cause the processor to produce at least one of: customized pump functions, recommendations to the user, or a histogram based on the signals received from the controller and inputs received from the user.

According to another aspect of the present disclosure, a system for pumping milk from a breast including a skin contact member to form a seal with the breast includes one or more of: a conduit in fluid communication with, the skin contact member at a first end portion of the conduit; a one-way valve connected at a second end portion of the conduit; and a driving mechanism configured to compress and release compression of at least one region of the conduit; wherein the compression and release of the compression provide driving forces for extracting the milk from the breast and pumping the milk out of the second end portion of the conduit.

In at least one embodiment, the skin contact member comprises a proximally extending segment joining the conduit and forming a chamber between the breast and the conduit.

In at least one embodiment, the segment forming the chamber extends downwardly from a nipple of the breast when the skin contact member is sealed to the breast.

In at least one embodiment, the segment comprises an outlet located where the conduit joins the segment, the outlet located in a lower portion of segment, so that milk, when contained in the segment extends to a fluid level above the outlet.

In at least one embodiment, the skin contact member comprises a flange comprising a compliant material.

In at least one embodiment, the segment comprises a flap which covers a predetermined portion of an opening of the segment, said flap being mounted on a living hinged such that a nipple of the breast bends the flap over to open the opening when inserted into the segment, and upon withdrawing the nipple from the segment, the flap returns to a position covering said predetermined portion of said opening.

In at least one embodiment, the flange comprises a stiff region comprising a stiff material less compliant than the compliant material.

In at least one embodiment, the stiff region is formed by an insert comprising the stiff material.

In at least one embodiment, the stiff region is integral with the flange.

In at least one embodiment, the skin contact member and the conduit are integrally formed.

In at least one embodiment, the skin contact member and the conduit are formed in portions dividable along axis aligned with a flow path of the conduit; wherein the portions can be opened up along the axis to facilitate cleaning internal surfaces of the skin contact member and the conduit.

In at least one embodiment, a segment of the portions is joined by a hinge, such that upon opening the portions for cleaning, the portions remain connected to one another via the hinge.

In at least one embodiment, the portions comprise mating connectors along perimeters thereof, to facilitate attachment and detachment of the portions to and from one another.

In at least one embodiment, the perimeters form an airtight seal upon connecting the portions together.

In at least one embodiment, the system further includes rigid frames that contact perimeters of the mating portions, providing a backing to facilitate forming a seal between the perimeters of the portions.

In at least one embodiment, the conduit includes a first region, a second region and a third region, the second region being upstream of the first region and the third region being downstream of the first region; wherein the first region has a first cross-sectional area, the second region has a second cross-sectional area, and the third region of has a third cross-sectional area; and wherein the first cross-sectional area is larger than the second cross-sectional area and larger than the third cross-sectional area.

In at least one embodiment, the second region is reinforced with at least one biasing member.

In at least one embodiment, the driving mechanism comprises at least one motor.

In at least one embodiment, the driving mechanism comprises an encoder cooperating with the motor to tract a current position of the motor.

In at least one embodiment, the skin contact member, the conduit and the driving mechanism are contained within a main body that is configured to be attached to the breast and supported by a bra.

In at least one embodiment, the system further includes a flange member releasably attachable to the main body to provide an appearance of a natural breast contour when clothing is worn over the flange member attached to the main body having been attached to the breast.

In at least one embodiment, the system further includes a contouring shell configured to receive the main body therein and to provide an appearance of a natural breast contour when the skin contact member is sealed to the breast.

In at least one embodiment, the system further includes a second skin contact member configured and dimensioned to form a seal with a second breast; and a second conduit in fluid communication with the second skin contact member.

In at least one embodiment, the driving mechanism is a first driving mechanism, the system further including: a second driving mechanism configured to compress and release compression of at least one region of the second conduit; wherein the compression and release of the compression of the at least one region of the second conduit provide driving forces for extracting the milk from the second breast and pumping the milk out of the second conduit.

In at least one embodiment, the second conduit is in fluid communication with the driving mechanism.

In at least one embodiment, the system further includes a controller configured to control operations of the driving mechanism.

In at least one embodiment, the system further includes a sensor configured to sense at least one dynamically changing characteristic within the system, the sensor being configured to input signals representative of the at least one dynamically changing characteristic to the controller.

In at least one embodiment, the sensor comprises a pressure sensor.

In at least one embodiment, the controller uses inputs signals from the sensor to control operations of the driving mechanism with a negative closed loop feedback mechanism, to extract milk from the first and second breasts.

In at least one embodiment, the system further includes a first controller configured to control operations of the first driving mechanism, and a second controller configured to control operations of the second driving mechanism.

In at least one embodiment, the system further includes a first sensor configured to sense at least one dynamically changing characteristic within the system, and a second sensor configured to sense the at least one dynamically changing characteristic within the system, the first sensor being configured to input signals representative of the at least one dynamically changing characteristic to the first controller and the second sensor being configured to input signals representative of the at least one dynamically changing characteristic to the second controller.

In at least one embodiment, the first sensor comprises a first pressure sensor and the second sensor comprises a second pressure sensor.

In at least one embodiment, the first controller uses input signals from the first sensor to control operations of the first driving mechanism with a negative closed loop feedback mechanism, to extract milk from the first breast and the second controller uses input signals from the second sensor to control operations of the second driving mechanism with a negative closed loop feedback mechanism, to extract milk from the second breast.

In at least one embodiment, the first and second controllers are configured to transmit and receive signals from one another for coordinated control of the first and second driving mechanisms.

In at least one embodiment, the system further includes one or more of an external computer comprising a processor, transmitter and receiver, the external computer configured to receive signals from the controller, calculate modified controlled parameters and send the modified control parameters to the controller, wherein upon receiving the modified control parameters, the controller modifies operation of the driving mechanism in accordance with the modified control parameters.

In at least one embodiment, the system further includes a cleaning bottle configured to input cleaning fluid into the skin contact member and the conduit for cleaning internal surfaces of the skin contact member and the conduit.

In at least one embodiment, the system further includes a cleaning implement configured to make physical contact with inner surfaces of the conduit for cleaning the conduit.

In at least one embodiment, the cleaning implement comprises a brush.

According to another aspect of the present disclosure, a method of pumping milk from a breast includes one or more of: generating suction pressure in a conduit in fluid communication with the nipple of the breast; monitoring at least one dynamic characteristic; and modifying the suction pressure in the conduit, as a result of feedback received from the monitoring.

In at least one embodiment, the monitoring comprises monitoring pressure.

In at least one embodiment, the monitoring comprises monitoring milk flow rate.

In at least one embodiment, the method further includes automatically ceasing suction pressure generation based on feedback received from the monitoring.

In at least one embodiment, the monitoring and the modifying are performed by a controller onboard a pumping system that includes a driving mechanism that generates the suction, the method further including: transmitting data from the controller to an external computer having at least one processor.

In at least one embodiment, the method further includes instructions which, when executed by the at least one processor cause the processor to: receive data transmitted by the controller; calculate at least one result using the data as inputs; and perform at least one of transmitting the at least one result to the controller and display the at least one result on a display of the external computer.

In at least one embodiment, the monitoring and the modifying are performed by a controller onboard a pumping system that includes a driving mechanism that generates the suction, the method further including: modifying, with an external computer external of the pumping system, instructions for carrying out at least one pump function by the pumping system; and transmitting the instruction to the controller.

In at least one embodiment, the monitoring and the modifying are performed by a controller onboard a pumping system that includes a driving mechanism that generates the suction, the method further including one or more of: providing an external computer external to the system; receiving data from the controller; and performing at least one of: customizing at least one pump function, calculating volume of milk extracted, tracking expression efficiency; monitoring expression efficiency over time, tracking inventory of expressed milk, tracking dates of milk pumping sessions, and tracking specific containers used in specific pumping sessions, based on data received by the external computer from the controller.

In at least one embodiment, the at least one pump function comprises at least one of: suction levels, suction waveforms, amplitude and duration of application of suction, phases of extraction or feeding times, rest programming, heating temperatures and times, vibration frequency and duration and pumping session duration.

In at least one embodiment, the method further includes displaying at least one image of a user's baby on a display of the external computer when milk is being pumped from the breast.

According to another aspect of the present disclosure, a method of improving breast pumping includes one or more of: generating suction pressure with a breast pump to cause expression of milk from the breast; monitoring at least one dynamic characteristic created by the breast pump; sending pumping data from the breast pump to an external computer; compiling, by the external computer, data received; and providing to a user at least one output calculated from the pumping data received from the breast pump.

In at least one embodiment, the at least one output comprises recommendations to a user about future breast pumping sessions.

In at least one embodiment, the at least one output comprises a histogram compiled by the external computer.

In at least one embodiment, the method further includes one or more of: modifying, by the external computer, instructions for at least one pump function, based on data received from the breast pump; transmitting the instructions for at least one pump function having been modified to the breast pump; and operating the breast pump using the instructions for at least one pump function having been modified.

In at least one embodiment, an interactive feature is provided on the external computer, wherein the external computer prompts a user to request input from the user when a downtrend is seen in milk extraction production, as to whether the mother is weaning.

According to another aspect of the present disclosure, a method of operating a breast pump includes one or more of: attaching a skin contact member of the breast pump to the breast to form a seal therewith; selecting a pumping mode; actuating a compression member to cycle through compression and retraction strokes, according to the pumping mode to generate suction to express milk from the breast; and automatically modifying the pumping mode based on feedback provided by a sensor in the breast pump.

In at least one embodiment, the method further includes one or more of: attaching a second skin contact member of a second breast pump to a second breast to form a seal therewith; selecting a pumping mode for the second breast pump; actuating a second compression member to cycle through compression and retraction strokes, according to the pumping mode to generate suction to express milk from the second breast; communicating data between the first and second breast pumps; and automatically modifying the pumping mode of at least one of the first and second breast pumps, based on the data communicated between the first and second breast pumps.

According to another aspect of the present disclosure, a method of facilitating breast pumping includes one or more of: a user providing personal data about at least one of the user and the user's baby into a program on a computer; sending pumping data from a breast pump during a breast pumping session to the computer; customizing a pumping mode tailored to the user based on the pumping data received from the breast pump and personal data inputted by the user; sending the customized pumping mode to the breast pump; and pumping milk from the user's breast according to instructions contained in the customized pumping mode.

These and other features of the disclosure will become apparent to those persons skilled in the art upon reading the details of the systems and methods as more fully described below.

BRIEF DESCRIPTION OF THE DRAWINGS

FIG. 13C is a side view of the embodiment shown in FIG. 13A, but shown with the external shell of the main body.

FIG. 13D is a side view of the embodiment shown in FIG. 13B, but shown with the external shell of the main body.

FIG. 19C shows a variant of the contouring shell of FIG. 19A.

FIG. 19D is a cross-sectional view of a contouring shell according to another embodiment of the present disclosure.

FIG. 19E is a cross-sectional view of a contouring shell according to another embodiment of the present disclosure.

FIG. 19F is a cross-sectional view of a contouring shell according to another embodiment of the present disclosure.

FIG. 20 illustrates a system wherein two devices are used together, according to an embodiment of the present disclosure.

DETAILED DESCRIPTION OF THE DISCLOSURE

Before the present systems and methods are described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a valve" includes a plurality of such valves and reference to "the pump" includes reference to one or more pumps and equivalents thereof known to those skilled in the art, and so forth.

The publications discussed herein are provided solely for their disclosure prior to the filing date of the present application. The dates of publication provided may be different from the actual publication dates which may need to be independently confirmed.

Figure 1A:
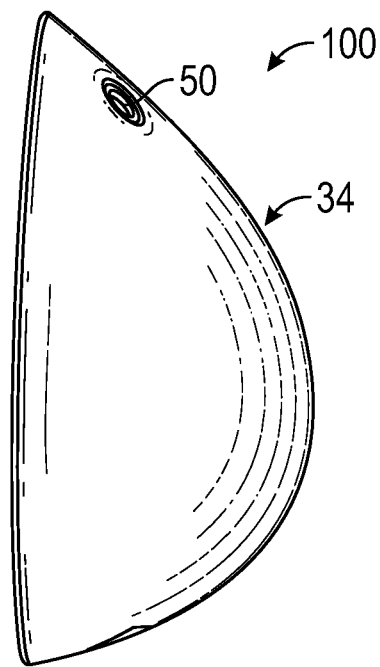
FIG. 1A is a side view of a breast pump system (without milk collection container) according to an embodiment of the present disclosure.
Figure 1B:
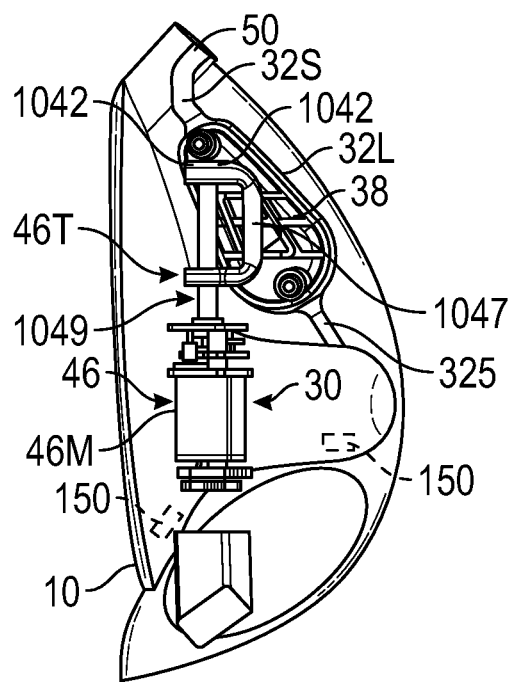
FIG. 1B illustrates components of the breast pump system of FIG. 1A with the exterior of the main body having been removed.
Figure 1C:
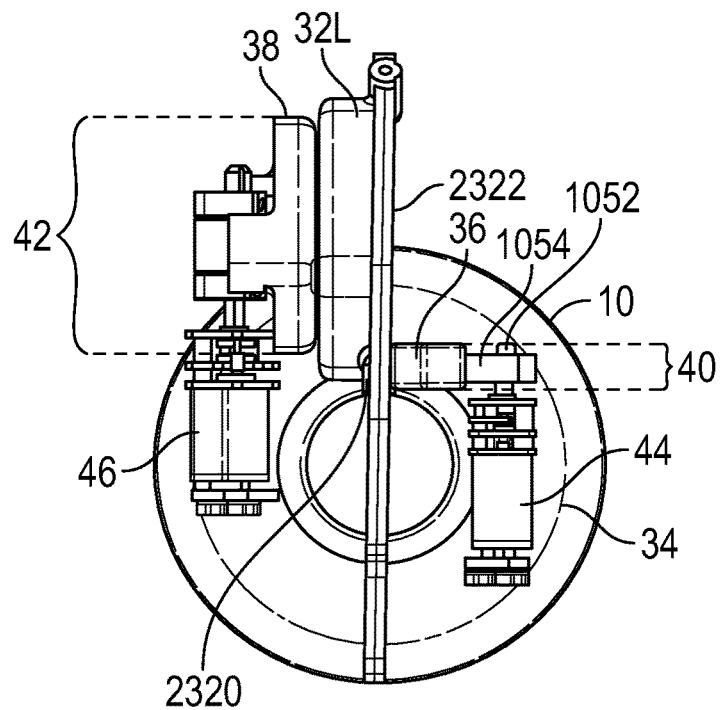
FIG. 1C shows a proximal end view of FIG. 1B.

FIG. 1A is a side view of a breast pump system 100 (without milk collection container) according to an embodiment of the present disclosure. The main body 34 of system 100 is shaped and configured to be contoured to the breast of a user and to thus provide a more natural appearance when under the clothing of the user. As can be appreciated from the figures, the system can define a natural breast profile. The natural breast profile is contemplated to fit comfortably and conveniently into a bra of a user and to present a natural look. As such, the profile is characterized by having a non-circular base unlike that embodied in a generally dome-shaped configuration. Extending from the base are curved surfaces having asymmetric patterns. Moreover, like natural breasts, the profile of the device or system is contemplated to define one or more asymmetric curves and off-center inertial centers. Various natural breast shapes can be provided to choose from to the tastes and needs of a user. FIG. 1B illustrates components of the breast pump system 100 with the exterior of the main body 34 having been removed. System 100 includes a skin contact member 10 (such as the breast flange shown in FIG. 1B, or member having a different shape, but configured to seal to the breast of a wearer and provide fluid communication with the pump) a pumping region 30 and a conduit 32. FIG. 1C shows a proximal end view of FIG. 1B, to illustrate more details of the pumping region 30.

Figure 9A:
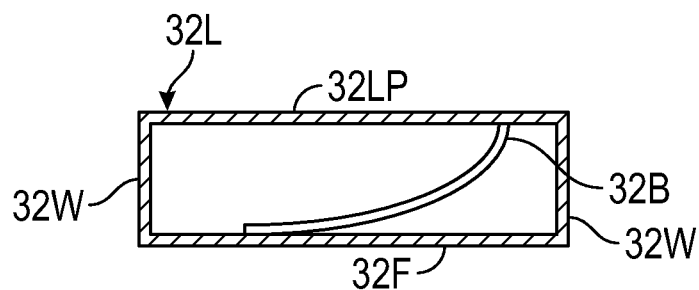
FIG. 9A a biasing member inside a chamber according to an embodiment of the present disclosure.
Figure 9B:
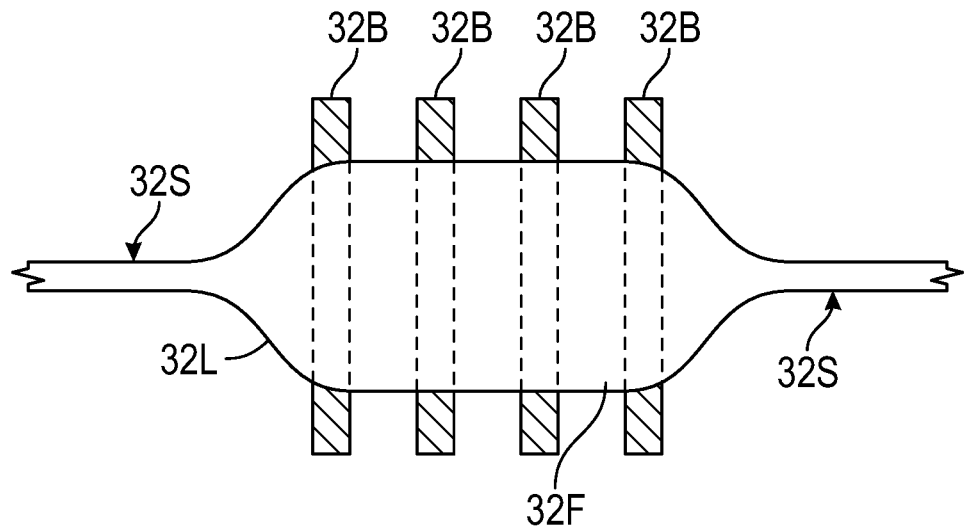
FIG. 9B illustrates resilient ribs attached to a backing face of a chamber according to an embodiment of the present disclosure.
Figure 9C:
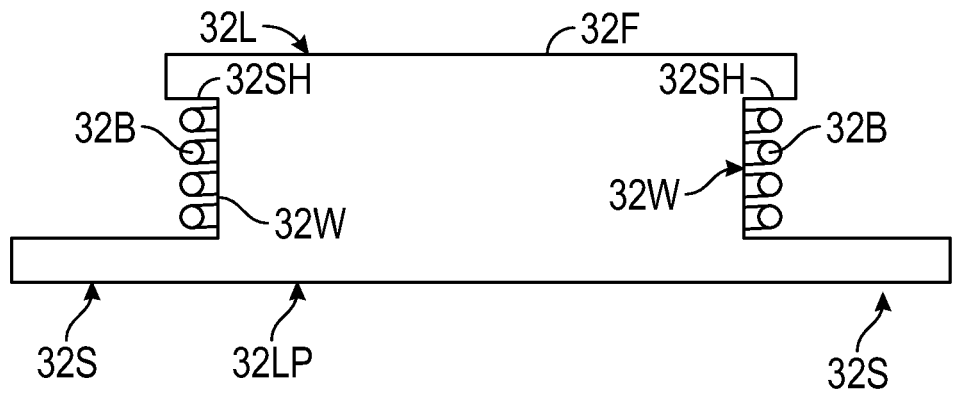
FIG. 9C illustrates compression springs installed along walls of a chamber according to according to an embodiment of the present disclosure.

The conduit region 32L in the embodiment of FIGS. 1A-1C in not cylindrical, but is formed as a pump chamber having a substantially oval face 32F and walls that extend substantially perpendicular thereto. The backing face 32LP, such as the backing plate 32LP shown in FIG. 2 is substantially oval in shape with a substantially flat surface the joins the walls 32W (see FIG. 9) of the chamber to seal the chamber. The conduit portions 32S are cylindrical as shown, but do not need to be tubular or circular in cross section. When tubular, the cross-sections may be oval, square, other polyhedral shape, non-symmetrical, or non-geometric shape. In one embodiment where tubing/conduit regions 32S are circular in cross section, 32S has an inside diameter of 0.104 inches and a wall thickness of 0.044 inches. Tubing 32S can have inside diameter dimensions in the range of 0.040 inches to 0.25 inches and wall thickness dimensions in the range of 0.006 inches to 3/32 inches. The hardness of the materials used to make tubing region 32S that is compressed by compression member 36 and compression chamber 32L (but not the backing member 32LP) can be in the range of 20 to 70 Shore A Durometer, typically in the range of 45 to 55 Shore A Durometer. However, these values may vary, depending upon the geometry of the portions 32S and 32L. Also, the material(s) used for the portions 32S, 32L is chosen for the ability to rebound against the high vacuum generated by the system. If the rebound is generated in another way, or assisted with another feature, the wall thicknesses and durometers of portions 32S and 32L can be relatively lower. Examples of assist features include, but are not limited to: ribbed reinforcement of portion 32L; attachment of compression members 36, 38 to portions 32S, 32L, respectively; and/or provision of one or more biasing members 32B such as a spring to provide or assist in providing rebound force, as illustrated in FIG. 9A, for example. One or more biasing members 32B may be incorporated into or the walls 32W and/or face 32LP of the chamber 32L. FIG. 9B illustrates resilient ribs 32B attached to the backing face 32LP of the chamber 32L. FIG. 9C illustrates compression springs 32B installed along walls 32W in between stiffened shoulders 32SH extending from face 32F and stiffened regions of conduit 32S or extensions of the still backing face 32LP. Alternatively, a single compression spring could be installed around all four walls between faces 32F, 32LP. Alternatively or additionally, one or more biasing members 32B may be positioned inside the chamber as illustrated in FIG. 9A. When positioned inside the chamber, the one or more biasing members are made as thin as functionally possible, to limit the amount of restriction to milk flow caused thereby.

Figure 9D:
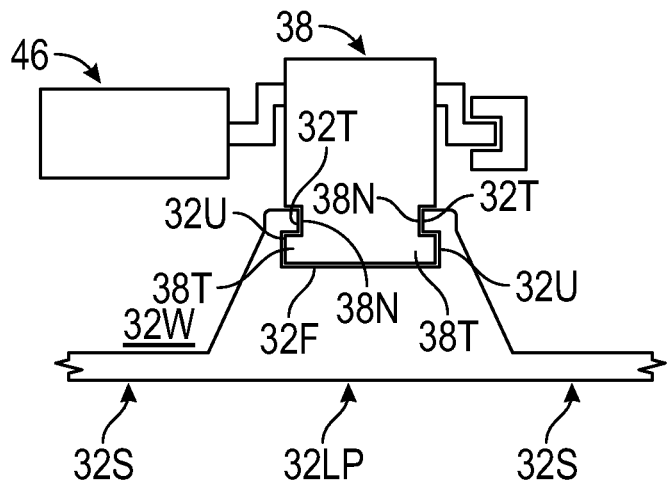
FIG. 9D illustrates a compression member attached to a conduit portion, according to an embodiment of the present disclosure.

Further alternatively or in addition to use of one or more biasing members, the face 32LP may include features that can attach to the compression member 38, so that when the compression member 38 moves in a direction away from the conduit portion 32L, the face 32F is drawn by the pulling force of the compression member 38, thereby facilitating its re-expansion or rebound from the compressed configuration. FIG. 9D illustrates one embodiment of this feature, in which undercuts or notches 32U are formed in the face 32F to mate with tabs 38T formed in compression member 38. Optionally, as also shown in FIG. 9D, notches 38N can be formed in compression member 38 to mate with tabs 32T extending from face 32F to further secure the connection between the compression member 38 and face 32F. The attachment between the compression member 38 and face 32 can be readily manually separated, thereby facilitating easy removal of subassembly 35 for cleaning, replacement, etc.

Two active compression elements 36, 38 are operable to compress and allow decompression of the conduit portions 32S and 32L, respectively at compressible regions 40 and 42, respectively. Although the preferred embodiment uses two active compression elements as shown, alternative embodiments could have three or more active compression elements. Resilient conduit 32 is preferably made of silicone, but could alternatively be made from other thermoplastic elastomers exhibiting the desired performance characteristics described herein, including, but not limited to polyurethanes and/or PEBAX. Different regions of conduit 32 may be made of different materials/material properties. The regions can all be molded of the same material, overmolded, glued or otherwise attached, constructed, etc. In at least one embodiment, the compressible regions 40, 42 may have different properties from other non "active" regions—such as those non active regions being rigid (e.g., tubing 32S upstream and/or downstream of the pumping region and/or other non-active regions) to improve pumping efficiency by reducing energy losses due to expansion and contraction of regions not intended to be active. The non-active regions can be made of different materials from the active regions or otherwise reinforced. The various regions can also be other shapes than circular in cross-section. The material(s) from which the compression regions 40, 42 of conduit 32L are made can be the same as that of the skin contact member 10, only differing optionally by thickness. Further alternatively, the material(s) from which the compression regions 40, 42 are made can differ from one another. A factor in the choice of material and material thickness and length is the response time required to expand the compression regions 40, 42 from a target compressed shape/state to an original, unbiased rebound configuration (e.g., return to a fully unbiased shape), force required to compress to the desired target compressed shape, expansile force (pressure drop) achieved when allowing the conduit portion 32L to self-expand, volume within the regions 40 and 42, compatibility with the materials for the remainder of the skin contact member 10 (nipple housing), resiliency to maintain its material properties through multiple wash, aging and use cycles, surface and depth characteristics such as material transparency, clarity and texture/feel against the skin, visual appearance, mechanical durability, tear resistance, shape memory, soft/hardness, biocompatibility, non-reactivity and free of leachables, heat/cold resistance, etc.

Examples of tubes 32S include, but are not limited to: silicone tubing, such as used in peristaltic pumps, both platinum-cured and peroxide-cured silicone tubes. Dimensions can range greatly in inside diameter and wall thickness, as noted above. Walls may also range to impact properties, with preferred embodiments in the ranges noted above. Inside diameters and wall thicknesses can be varied, as needed, with ensuing appropriate lengths of tubing 32. Likewise, the dimensions, wall thicknesses and volume capacity of chamber 32L may vary, as noted above. Other factors that are considered for material choice and geometry of portions 32L and 32S include characteristics of the material for hysteresis, under the pressures (vacuum levels) experienced during use over repeated cycles, elongation, tensile strength modulus of elasticity and tear strength, etc.

In the embodiment of FIG. 1C, compression element 36 is minimized, so that length 94 is in the range of about 1 to 4 mm, preferably about 1 to 2 mm, so that it is effective to seal off the tubing 32S, but operates in concert with compression element 38 to establish sufficient suction/vacuum for extracting milk. The length 94 at the proximal end of the compression element 36 is in the range of about 0.25 inches to 1.0 inch, in at least one embodiment, about 0.75 inches, and tapers to a length 97 of about 1/16 inch to about 3/16", typically about 1/8 inch. The compression element tapers nearly to a point, but not too sharp to run the risk of cutting the tube 32S. Thus, the initial contact surface of compression element 36 against tube 32S is minimized to minimize the amount of force required to initiate collapsing of the tube 32S. Because the contact surface spans across the entire width of the tube 32S, it pinches off the tube 32S against the anvil surface 2320, thus sealing this location in an airtight, liquid-tight manner, so that the suction level experienced by the breast does not change as the compression element 38 works to change the suction level in the conduit 32 downstream of the compression member 36.

The width of compression element 36 is typically at least as great as the inside diameter/width of the conduit 32S at region 40, most typically greater than or equal to the outside diameter/width of portion 32S, but could be equal or slightly less than the inside diameter/width or less than the outside diameter/width but greater than the inside diameter/width, since the compressive action of the compression element 36 against portion 32S extends slightly past the ends of the compression element 36. By minimizing the length 94, less force is required to seal off the tube 32S, as compared to the force necessary to seal the tube 32S using a compression element 36 having a greater length. Also, the relatively smaller diameter/width of conduit portion 32S compared to cross-sectional width of conduit portion 32L allows the conduit portion 32S to be sealed with a relatively shorter throw of the compression element 36, thereby reducing power requirements of the system 100, which can lead to a smaller driver 44 being used, a smaller battery due to the lower energy requirements, and/or longer operational time before the system 100 needs to be recharged or plugged in to an AC power source (in embodiments where this is possible). Response times of the system 100 may also be faster. The time required for the compression element 36 and the conduit region 32S to completely seal at 40 or release may be shorter. Also, there is less volume that is moved on the final close during feedback, so if the sealing element 36 is near closing and waiting for the pressure feedback controlling the larger compression element 38 to establish the desired pressure before closing, the smaller profile corresponds with less volume change on that final seal motion. Therefore the sealing can be more precisely and accurately controlled.

Figure 10:
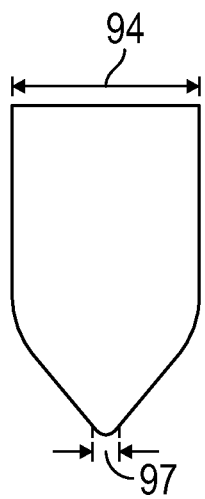
FIG. 10 illustrates a view of a compression member according to an embodiment of the present disclosure.

The compression elements 36 and 38 are driven by dedicated compression drivers 44, 46. Alternatively, compression elements 36 and 38 could be driven by a single compression driver, controlled by controller 52 to drive each of the compression elements 36, 38 in the manner desired. In a mechanical system (linkage or cable), a clutch or toggle switch can be used to engage and disengage the compression element 36 at the appropriate time. In a hydraulic or pneumatic system, an additional solenoid valve can be used to shunt power to the compression element 36. As shown, the compression elements 36, 38 comprise pistons, but alternative features could be used to accomplish the same function, such as lever arms, screw drives, clamps, cams, pincers, rollers, magnets, electro-magnets, linear drives, solenoids, gears, stepper motors, or other features, respectively. The compression surfaces of the compression elements 36, 38 may be formed as flat paddles to allow complete crushing of the regions 40, 42 without residual volume. Alternatively, one or both compression surfaces may be formed with a "V-shaped" or "U-shaped" edge (such as in the embodiment of compression member shown in FIG. 10). When so configured, the U-shaped or V-shaped edge of compression member 36 is transverse to the direction of flow through region 40 and the U-shaped or V-shaped edge of compression member 48 is aligned with the direction of flow to allow less force to compress conduit 32 to the same distance of compression, relative to a flat surface paddle.

One or both compression surfaces may be formed as roller paddles having curved surfaces so that the compression action is not simply straight into the tubing 32. The roller paddle surface can roll on the conduit 32 to seal and move in a given direction. Dual action of the roller can be provided, so that, initially the roller comes down in compression against the conduit 32 and seals the tube 32, which may be capable of being performed with relatively low force. Secondarily, the roller paddle can roll the compression surface in a predetermined direction along the length of the tube 32 and squeeze a volume of milk or air or combination in a given direction. This can be useful to maximize both increase and decrease in pressure changes and fluid movement.

Each compression element 36, 38 is operatively connected to a driver 44, 46, respectively, for independent but coordinated driving and retraction of the compression elements 36, 38. When electrically-powered drivers are used, a battery 48 is electrically connected to the drivers 44, 46 and supplies the power necessary to operate the drivers 44, 46 to drive the compression and retraction of the compression elements 36, 38 (see FIG. 14). Battery 48 may be induction charged to allow for more water resistance of the device. In an induction-chargeable embodiment, no plug is required to charge the battery 48, but rather the device can be placed on an induction charger that optionally includes a magnet to keep the induction charger properly aligned with the battery for induction charging. For embodiments not employing induction charging, the device can be charged via plug in to an AC charger. Further optionally, a battery brick can be provided in an accessory bag, so that when the device is placed in the accessory bag, it begins charging off the larger battery contained in the "battery brick". Additionally, the battery brick can be plugged into an AC outlet to charge itself, without the need to remove the battery brick from the accessory bag. Further advantageously the battery brick can be configured to charge a pair of devices (pumps) simultaneously when both device are placed in the accessory bag.

A sensor 54 (see FIGS. 2 and 3, which show alternative placement locations) is used to provide feedback to the controller 52 for controlling the pumping cycles to achieve and/or maintain desired vacuum levels. In this way, milk ducts are not overly collapsed during a rest or lower suction pressure phase but rather the ducts are allowed to fill like when a baby is latched to a breast. This re-filling allows for more efficiency in milk extraction more similar to a baby than conventional pump devices. Sensor 54 is preferred to be a pressure sensor but could also be a flow, temperature, proximity, motion sensor or other sensor capable of providing information usable to monitor the safety or function of the pump mechanism of system 100. In a preferred embodiment, the pressure sensor is a non-contact type that does not come into contact with the milk. For example sensor 54 can be a thinner wall (or otherwise configured to be more flexible) than the surrounding locations, so that it flexes with changes in pressure, and the positions of the flexing thin wall can be monitored by a sensitive physical gauge (e.g., pressure sensitive resistor, strain gauge, etc.) that contacts the flexing thin wall of an optical monitor, each of which inputs to the controller 52, so that the controller can calculate the pressure relative to the position of the thin wall. Other embodiments of non-contact sensor that can be used are disclosed in provisional application Ser. No. 62/027,685, filed Jul. 22, 2014, which is hereby incorporated herein, in its entirety, by reference thereto. Alternatively, a contact type pressure sensor 54 can be employed. Examples of contact-type pressure sensors 54 that can be employed are disclosed in provisional application Ser. No. 62/050,810, filed Sep. 16, 2014, which is hereby incorporated herein, in its entirety, by reference thereto. Upon powering up the system the controller 52 calibrates the pressure sensor 54 to atmospheric pressure, so that it is accurate regardless of the elevation at which it is being used. Preferably sensor 54 is located nearby where the tip of the nipple 3 of the breast 2 is located to determine actual pressure being exposed to the breast 2/nipple 3, but other sensors 54 may be located within the system 100, for example, near where the one-way valve 50 is located, and can be used to monitor other features such as container 60 contents or expulsion pressure or flow rate. With at least one sensor 54 present, by monitoring either flow or pressure directly or indirectly and also taking into account the cycles and actual positions of the compression elements 36, 38 over time, it is possible to derive/calculate approximately the volume of milk produced during a pumping session as well as understand the flow-rate at any particular time in a pumping session. The accuracy of this measurement is greatest when there is no leak of air around the breast 2 and also when there is negligible air within the tube 32, after elimination by a few cycles of the pumping mechanism.

A one-way valve 50 such as a duckbill valve or other type of one-way valve is provided at the end of conduit 32 (see FIG. 1B where it enters the milk collection/storage container 60) or is connected in fluid communication with another conduit 32' that can connect to a milk collection/storage container 60. Valve 50 prevents back flow of milk into the tube 32, as well as preventing air from entering the proximal end of the tube and thereby maintains the suction (vacuum) level in the conduit 32. Valve 50 can further be designed to open in the reverse direction, for safety purposes, if a predetermined maximum vacuum level is exceed in tubing 32, such as greater than 250 mm Hg vacuum (−250 mm Hg pressure), for example. In at least one embodiment, the pressure at which the valve 50 opens to allow flow into the milk collection container 60 is about 25 mm Hg. In an alternative embodiment, a pressure relief valve 150 (see FIG. 1B) can optionally be provided in the system 100, such as in the skin contact member 10, or other location along conduit 32. The pressure relief valve 150 can be configured to release at vacuums greater than a predetermined amount, (e.g., vacuums greater than 250 mm Hg (pressures less than −250 mm Hg), or some other predetermined maximum vacuum level). If vacuum at the breast 2 were to get too strong, the pressure relief valve 150 provides a mechanical release to prevent vacuum from getting stronger. For example, the pressure relief valve may be set at −250 mmHg, the prevent any suction pressure less than −250 mm Hg. The pressure relief valve 150 can be in the form of a spring and ball, pin and O-ring, or other equivalent mechanical means of providing pressure relief. The one-way valve 50 can be configured and designed such that it allows fluid to flow through it only when the pressure in tubing 32 is positive, e.g., about 25 mm Hg, or some other predesigned "crack pressure". The action of the compression elements cycles between increasing vacuum when the compression elements move in a direction away from conduit 32 and decreasing vacuum when the compression elements compress the conduit 32 (regions 40, 42), but typically should not increase the vacuum to greater than the predetermined maximum vacuum. As the compression elements 36, 38 compress the conduit 32 (against anvil surfaces 2320, 2322, respectively, see FIG. 3C), the pressure in the system 100 goes up and reaches the minimum suction level (e.g., −60 mmHg, −30 mm Hg, or some other predetermined minimum suction level), at which time the compression member 36 seals off portion 32S (region 40) thereby maintaining the minimum suction against the breast 2. Continued compression of portion 32L by compression member 38 continues to increase the pressure downstream of compression member 36, until the crack pressure is reached (e.g., 25 mm Hg or some other predetermined, positive crack pressure), that opens the one-way valve 50. The compression elements 36, 38 continue compressing tube 32, pumping fluid (milk) through the one-way valve 50 and into the collection container 60 until the compression element 38 reaches an end point in travel (typically before "bottoming out" against the anvil). The end point in travel of the compression element 38 against portion 32L may be predetermined, or may be calculated on the fly by the controller 52 using feedback from pressure sensor 54 and feedback from the driver of the compression element 38, from which the controller 52 can calculate the relative position of the compression element 38 over the course of its travel. The compression member 36 remains closed throughout this process, as it is used to seal off the conduit 32 at region 40 the entire time that the compression element 38 is pumping milk out of the region 42 and into the collection container 60. As the compression elements 36, 38 reverse direction and pull away from the conduit 32, they start the cycle again.

Figure 2A:
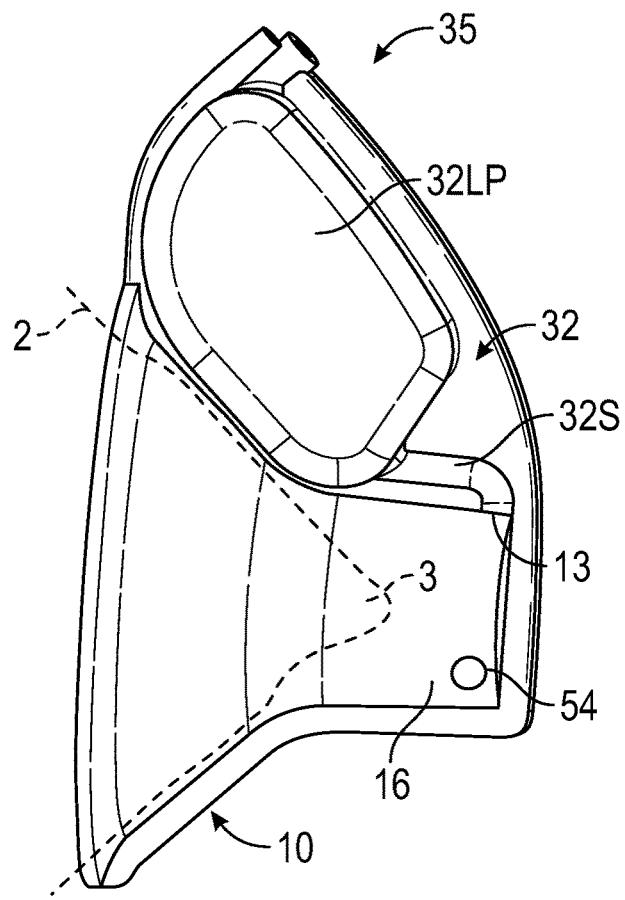
FIG. 2A is a perspective view of a skin contact member integrally formed with a conduit, according to an embodiment of the present disclosure.
Figure 2B:
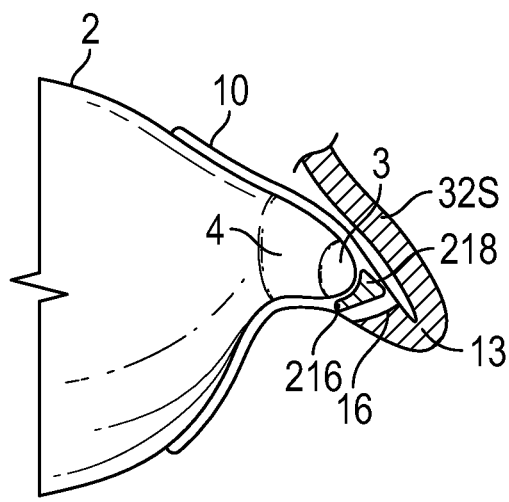
FIG. 2B illustrates a skin contact portion with a downwardly sloping proximal segment, according to an embodiment of the present disclosure.

FIG. 2A is a perspective view of the skin contact member 10 integrally formed with the conduit 32, according to an embodiment of the present disclosure. An open segment 16 within the housing of the skin contact member 10 is configured and dimensioned to allow for at least some clearance and space in front of the nipple 3 to permit milk to exit the nipple even when the nipple is pulled forward by suction. Open segment 16 is typically distinct from the main body of the flange 10 as the flange 10 tapers to meet the generally non-tapered chamber of the open segment 16. In the embodiment shown in FIG. 2, an outlet 13 is formed at or near the top of the proximal end portion of the segment 16 when the flange 10 is attached to the breast 2. This ensures that any air present between the breast 2 and the flange 10 is expelled initially, prior to pumping of milk. In an alternative embodiment, outlet 13 is formed at or near the bottom of the proximal end portion of the segment 16 when flange 10 is attached to the breast 2, as illustrated in FIG. 2B. This placement of the outlet 13 facilitates pumping milk out of the flange 10 after a breast pumping session has ended and the flange 10 has been removed from the breast 2. In addition to placing the outlet 13 at the bottom of the proximal end portion of segment 16, the embodiment in FIG. 2B provides a skin contact member 10 has a segment 16 that angles downwardly away from the nipple 3 when skin contact member 10 is attached to the breast. This orientation helps to minimize the volume of milk remaining in the skin contact member 10/segment 16 at the end of a pumping cycle, as the milk drains by gravity to the lowest level in the segment 16, where the outlet 13 is located. Also, the downwardly projecting angle of the segment and skin contact member 10 directs the nipple 3 downwardly and minimizes air/dead volume 216. Also, the teat is pulled into the skin contact member 10 with less pressure swing and less movement so segment 16 can be designed as a relatively smaller volume, again leaving less milk 218 at the end of a pumping cycle, and with less risk of chafing or bottoming out of the nipple (teat) in the segment 16. The outlet 13 is below the level where the breast 2 contacts the skin contact member most proximally. Accordingly, this reduces the chances of spilling milk when the skin contact member 10 is removed from the breast. The descending angle of the segment 16 also permits the user to tilt back to a certain degree (such as reclining in a chair or bed) while still maintaining the level of the milk 218 below the proximal most contact between the breast 2 and the skin contact member.

Further alternatively, the outlet 13 can be formed intermediate the top and bottom of the proximal end portion of the segment 16 when flange 10 is attached to the breast 2, in any of the embodiments described. This placement facilitates some extraction of air out of the space in the flange 10, while also facilitating pumping milk out of the flange 10 when the flange has been removed from the breast 2.

The subassembly 35 shown in FIG. 2 contains the only components that come in contact with the milk of the user (other than the milk collection container). The subassembly of FIG. 2 is made to be readily removable from the system 100 for cleaning and, in a preferred embodiment, is machine washable. After cleaning the subassembly of FIG. 2 can be easily reinstalled to the system for the next pumping session. In an alternative embodiment, subassembly 35 is made as a disposable part of the system 100 that is removable and replaceable. In one embodiment, the entire subassembly 35 of FIG. 2 is made integral. In another embodiment, the subassembly 35 is made with a split casing so that first and second side portions (which may be hinged, or may be completely separable from one another) can be opened to allow easier cleaning.

Figure 3:
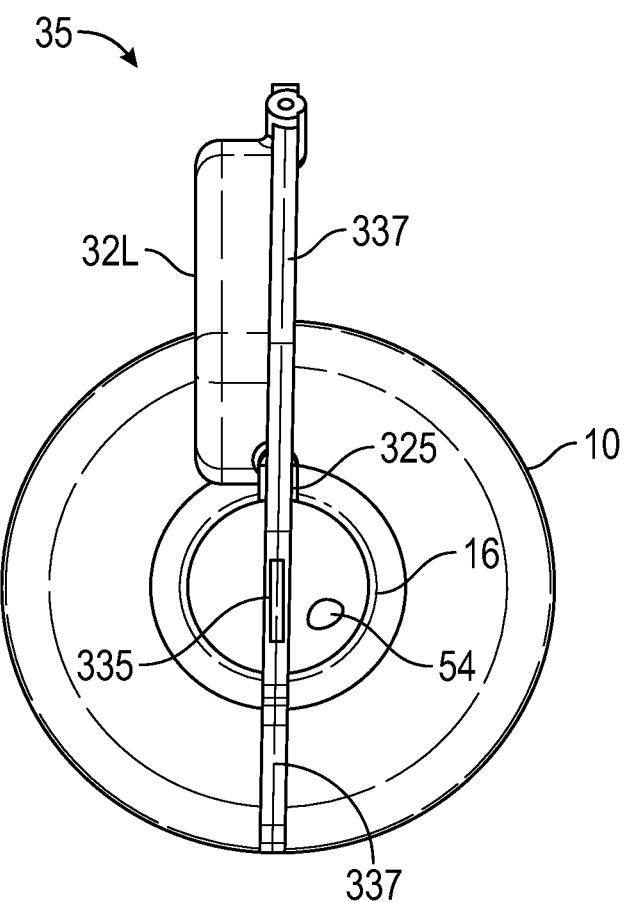
FIG. 3 shows a proximal end view of a subassembly according to an embodiment of the present disclosure.

FIG. 3 shows a proximal end view of a subassembly 35 that includes the split casing mentioned above. In this embodiment, a living hinge (or other hinge mechanism) 335 joins the two portions of the subassembly, even when they are separated along the juncture 337. In an alternative embodiment, hinge 335 is not present, such that the two portions can be completely separated from one another.

FIG. 4A illustrates a cleaning accessory 410 provided to facilitate cleaning of the subassembly 35 either when the subassembly 35 is still installed within the system 100, or after having removed the subassembly 35 from the system, such as like shown in FIG. 2. In this embodiment, cleaning accessory 410 includes a squeeze bottle 412 that is compressible to force cleaning fluid under pressure through the skin attachment member 10 (chamber 16) and conduit 32, and out of the subassembly to flush and clean the interior surfaces thereof. An application tip 414 of the cleaning accessory 410 is configured with a flange shape to seal with the skin contact member 10 so that back flow of the cleaning fluid around where the application tip 414 meets the skin contact member 10 is eliminated or minimized and pressure application is enhanced. The connection tubing 416 joining the application tip 414 to the squeeze bottle 412 in fluid communication, can be angled, as shown, or extend straight out of the bottle 412.

Figure 5:
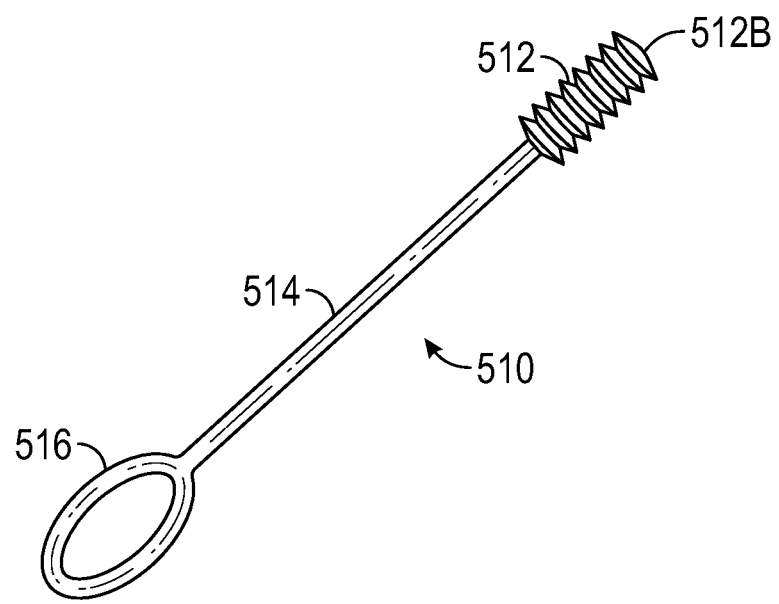
FIG. 5 illustrates a cleaning implement according to an embodiment of the present disclosure.

FIG. 5 is an illustration of a cleaning accessory 510 according to another embodiment of the present disclosure. Accessory 510 can be used separately of, or in conjunction with accessory 410. Accessory 51 comprises a distal end portion comprising a bottle brush 512 sized and dimensioned to fit within the small conduit portions 32S with some compression of the bristles 512B of the brush. The shaft 514 of the accessory 510 is resiliently flexible, allowing the brush portion 512 to be advanced into the conduit 32 up to and through the large portion 32L of the conduit. Optionally, a handle 516 may be provided at the proximal end of the accessory 510 to facilitate handling and operation by the user.

Figure 4:
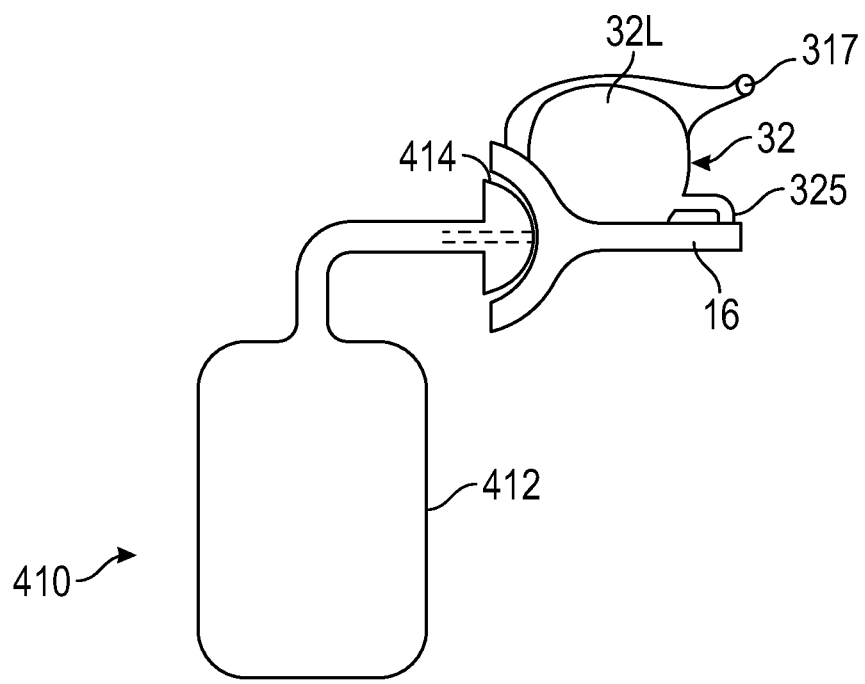
FIG. 4 illustrates a cleaning bottle administering cleaning fluid to a skin contact member and conduit, according to an embodiment of the present disclosure.

Further alternatively, or in addition to use of one or both of the accessories described with regard to FIGS. 4-5 and/or dishwashing and/or manual washing, the system can be provided with a wash mode in which the pumps of the system are operable to pump cleaning fluid through the chamber 16 and conduit 32 to clean the milk contacting surfaces.

Figure 6:
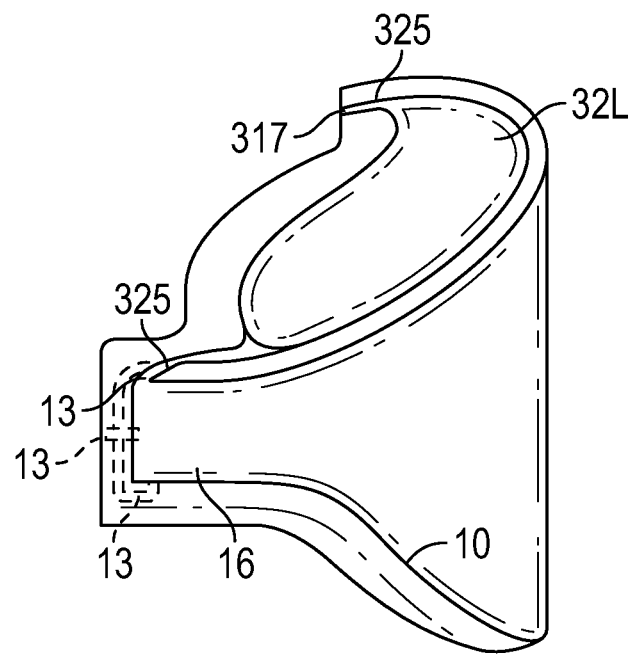
FIG. 6 shows one side portion of the subassembly of FIG. 3.

FIG. 6 shows one side portion (the left side portion of the illustration of FIG. 3) of the subassembly 35 showing the internal surfaces thereof. The fluid pathway provided by the subassembly starts at the interface with the breast 2, within skin contact member 10 through segment 16, outlet 13, small conduit portion 32S, large conduit portion 32L (pump chamber, in this embodiment), proximal small conduit portion 32 and out of the subassembly, through a one-way valve (not shown in FIG. 6) and into a milk collection container (also not shown in FIG. 6). As shown in FIG. 6, outlet 13 is provided at the top of the proximal end portion of segment 16. Alternatively, outlet 13 may be form at the bottom of the proximal end portion of segment 16, or intermediate the top and bottom of the proximal end portion of segment 16, as illustrated in phantom in FIG. 6. The volume of the internal chamber formed by the pump chamber (portion 32L) of the conduit 32 is typically in the range of about two to eight $cm^3$, in at least one embodiment, the volume was about four $cm^3$. The dimensions of the pump chamber could be any combination of dimensions that provide the volume described above. In one embodiment, 32L formed as a tubular structure had an inside diameter of about 0.5" (but could be within a range of about 0.25" to about 0.75") with a length set by the volume requirements. Other shapes include rectangular, oblong shape (such as an oblong tube, conical tube, etc.), or any other shape designed to fit into the form factor of the device and meet the functional requirements.

As shown in FIGS. 3 and 6, the large conduit portion (pump chamber) 32L is formed so that the capacity of the chamber is all on one side of the subassembly (the side shown in FIG. 6), with a flat backing plate formed to oppose it. Alternatively, the capacity of the chamber could be formed all on the other side, or could be divided among both sides, either symmetrically or asymmetrically. By providing the capacity all on one or the other sides, this facilitates the provision of a flat backing plate that is stiffer than the remainder of the large conduit portion/pump chamber 32L. The small conduit portion 32S that is configured to be compressed by compression member 36 is formed symmetrically about both sides of the subassembly 35, but could alternatively be formed asymmetrically. Likewise, the small conduit portion 32S leading out of the large conduit portion 32L and having an exit opening 317 for delivering milk out of the subassembly 35 and into the milk collection container, is formed symmetrically about both sides of the subassembly 35, but could alternatively be formed asymmetrically. Although the tubing portions 32S are round in cross-section in the embodiment shown, they could alternatively be made to have different shapes, such as oval, trapezoidal, other polygonal shape or other non-polygonal shape, as long as the shape is open so as to provide a lumen therethrough, and functions with the mechanical characteristics desired.

Figure 7:
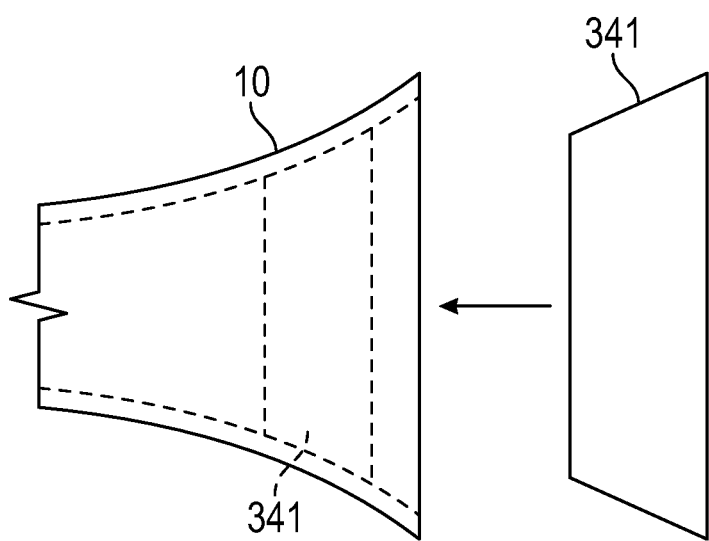
FIG. 7 illustrates a flange stiffener according to an embodiment of the present disclosure.

All the components of the subassembly 35 are compliant and resilient, except for backing member 339 which is made stiff and relatively rigid, so as to resist deformation when compression member 38 is driven toward it. Optionally, a portion of flange 10 may be made stiffer than the compliant material of the subassembly and/or an insert 341 of stiffer material may be placed in the flange as illustrated in FIG. 7. Alternative to the placement shown in FIG. 7, the insert 341 could be configured and dimensioned to stiffen the outer rim of the flange 10, or a portion further proximal of the location shown in FIG. 7. Further alternatively, rather than an insert 341, any of these portions could be integrally formed with a stiffer material, or insert 341 could be molded within the flange 10. Further alternatively, combinations or all of the aforementioned portions could be made stiff. If a removable insert 341 is used, the present disclosure includes customizing the size and shape of an insert to the particular needs of the individual user, including size and shape of the breast, as well as user preferences regarding comfort. Further alternatively, a plurality of inserts 341 of various sizes, shapes and/or stiffnesses can be provided, among which the user can select for the desired fit and comfort. Still further alternatively, an insert 341 can be made adjustable so as to fit different sized breasts and the individual comfort requirements of the user.

Figure 8:
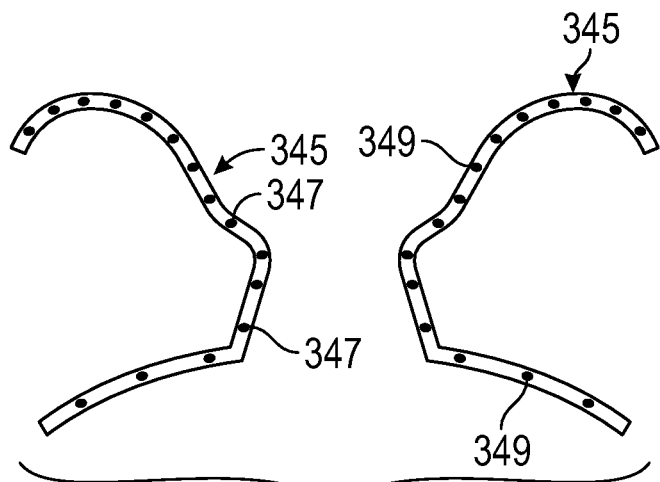
FIG. 8 illustrates rigid frames according to an embodiment of the present disclosure.

For embodiments of the subassembly 35 that are separable, either with our without the hinge 335, a rigid frame 345 can be provided to fit over the borders of the left and right subassembly portions where they can snap together to form a seal upon rejoining the portions, see FIG. 8. The frames 345, see FIG. 8, are made of a rigid material such as stainless steel, titanium, ABS plastic or other rigid plastic. The borders of the left and right subassembly portions that are sandwiched by the frames 345 are compliant and form an airtight, liquid tight seal between them when rejoining the subassembly portions. For example, the borders may be made of silicone, or any other compliant polymer disclosed for making the tubing 32 and skin contact member 10 in Provisional Application No. 62/050,810, which was incorporated herein, in its entirety, by reference thereto, above.

Optionally, male members 347 (e.g., pushpins, barbs, male portions of snaps or other protruding extensions) may extend from frame 345 and the border that frame 345 covers, and female members 345 (e.g., openings, female portions of snaps, nuts, etc.) that mate with male members 347 may be formed in the opposite frame and align with openings through the opposite border that the opposite frame covers. Upon pressing the two portions of the subassembly 35 together, the male members 347 pass through the openings 349 in the opposite border and frame 345 and retain the male members 347, with a force sufficient to compress the borders together to form an airtight, fluid-tight seal. The retention of the male members 347 by the female members 349 can be overcome when manually separating the portions of the subassembly 35, using manual force greater than the compressive forces applied to the borders. The suction that is generated within the subassembly 35 during use further enhances the seal between the borders. Further alternatively, the borders can be sealed and unsealed using a zipping mechanism similar to what is used in food storage bags.

Figure 11:
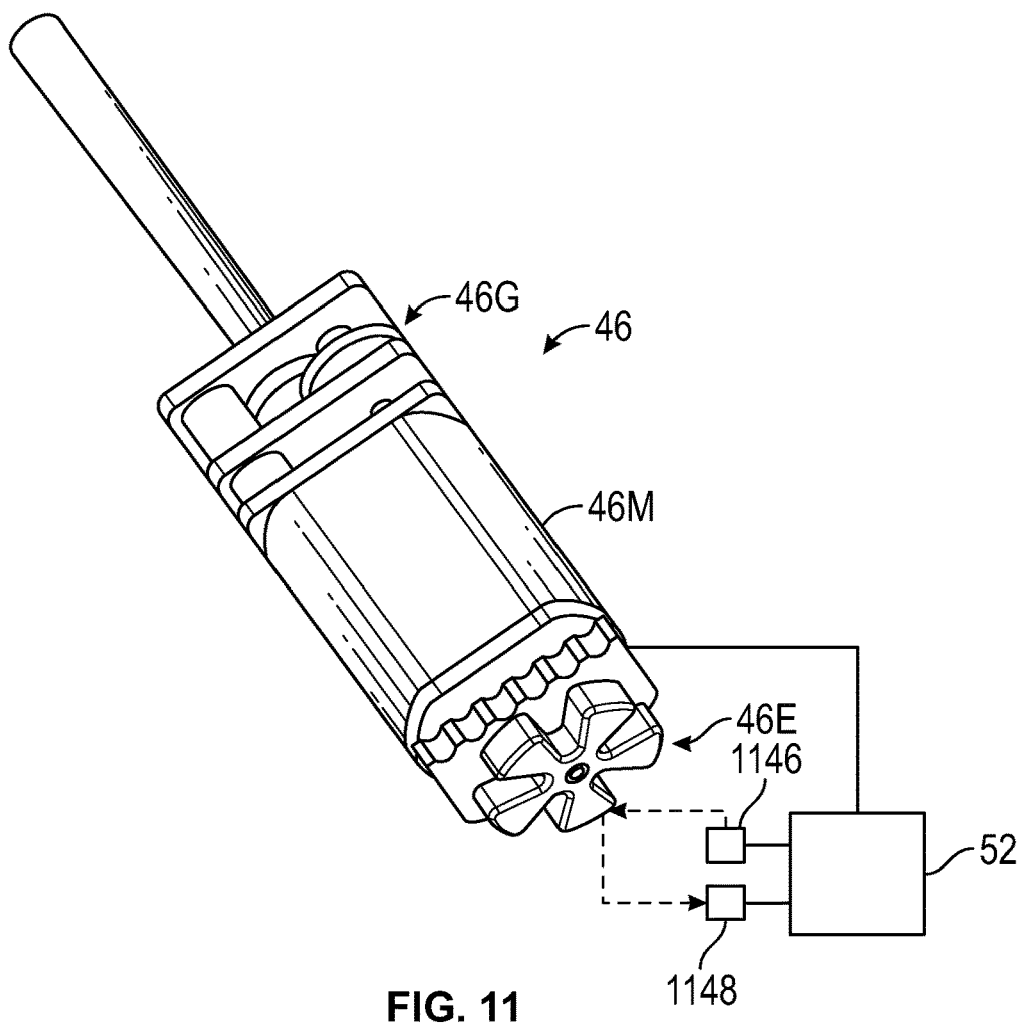
FIG. 11 illustrates a motor and encoder according to an embodiment of the present disclosure.

FIG. 11 is a perspective view of driver 46 shown in FIG. 1C. Driver 46 includes a servo motor 46M, and a gear box 46G and an encoder 46E mounted to opposite ends of motor 46M. As motor 46M rotates, encoder 46E, which is fixed relative to the rotating motor shaft, rotates with the motor. An optical monitor 1146, such as an infrared laser or the like is beamed against the encoder 46E, such as the rotating blades of the encoder 46E cross the optical beam emitted by the optical monitor 1146 as the motor rotates. As the blades cross the beam, the beam is reflected back to a sensor 1148. By counting the reflections, the sensor 1148 and controller 52 can calculate the position of the motor 46M from a start position, and the position of the compression member 38 that it is driving, relative to a reference or starting position of the compression member. A similar arrangement is provided for the driver 44 of compression member 36.

Figure 12:
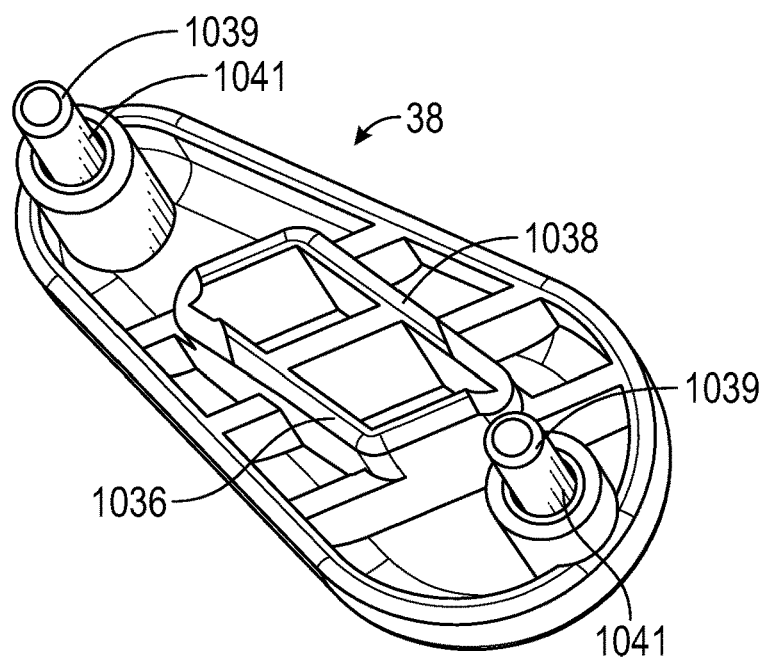
FIG. 12 is a view of a compression member according to an embodiment of the present disclosure.

The drive train 46T of the driver 46 includes a shaft 1042 that is received in journal bearing 1044 mounted to the frame 1030 of the main body 30. Driving rod 1047 is offset from shaft 1042 by configuration in crankshaft 1049 that is rotated (oscillated) by servo motor 46 to drive the compression member 38 toward and away from the conduit portion 32L. The driving rod 1047 engages with surfaces 1038 of compression member 38 (see FIG. 12) to drive the compression member 38 against the conduit portion 32L and, upon reverse oscillation of the motor 46, pulls away from the surfaces 1038 to allow the conduit portion 32L to resiliently return towards its unbiased configuration. The opposite surface (back side surface, not visible in FIG. 6) forms the anvil 2232 against which the large tubing section 32L is compressed. Pins 1039 mounted in housing 30 are received in closed-ended (blind) holes 1041 in the compression member 38 to maintain the compression member 38 in alignment with the region 42 and the driving rod 1047 as it travels toward and away from the conduit region 42L. Compression members 36, 38 are preferably made of ABS plastic, glass-filled ABS plastic, polycarbonate, or other rigid plastic.

Figure 13A:
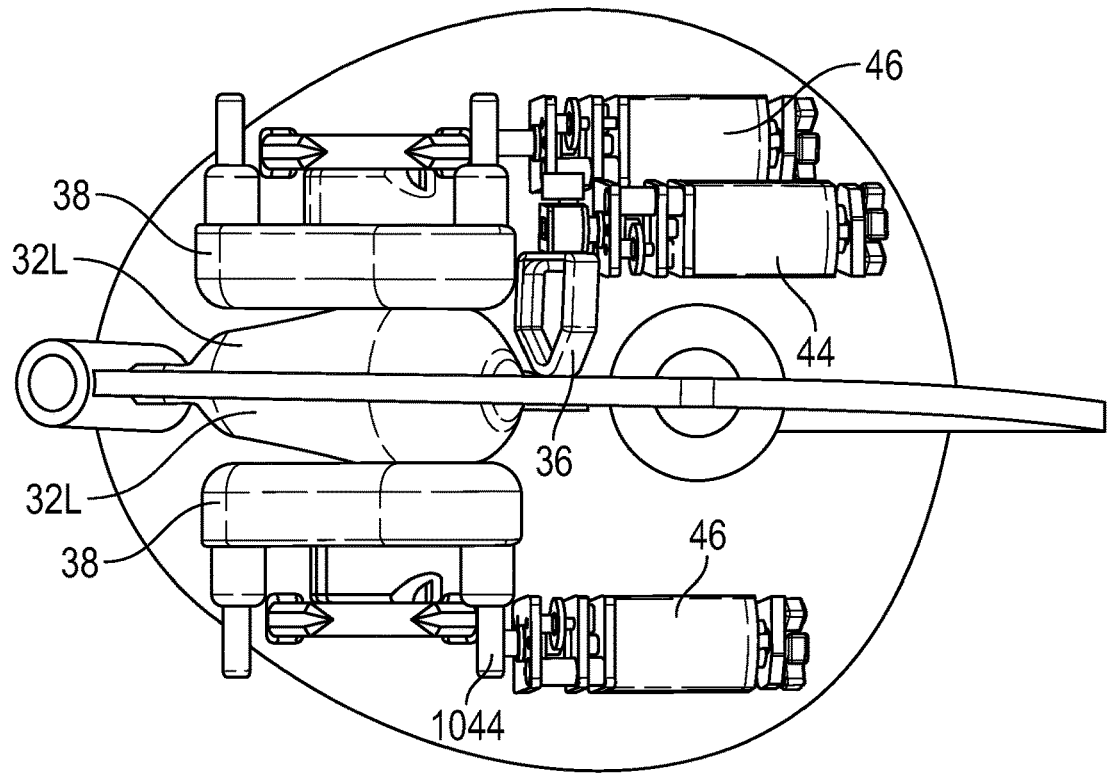
FIG. 13A illustrates the use of two compression members for compressing a pumping chamber, according to an embodiment of the present disclosure.
Figure 13B:
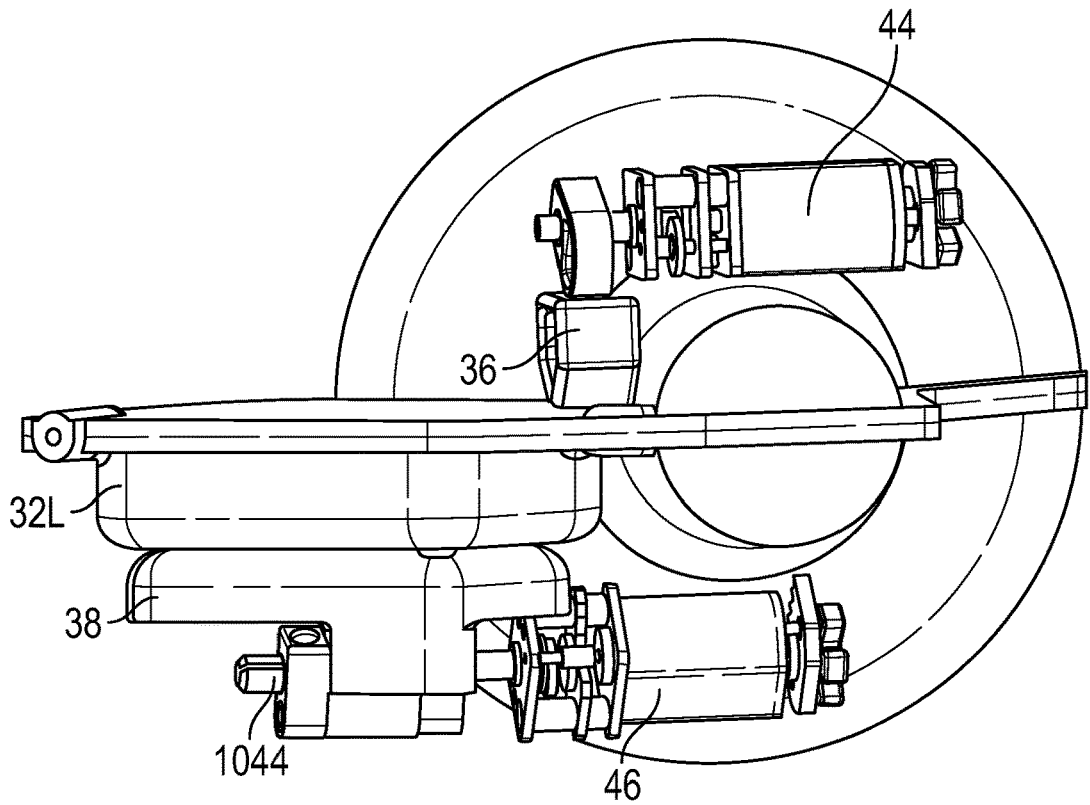
FIG. 13B illustrates the use of one compression member for compressing a pumping chamber, according to an embodiment of the present disclosure.
Figure 13E:
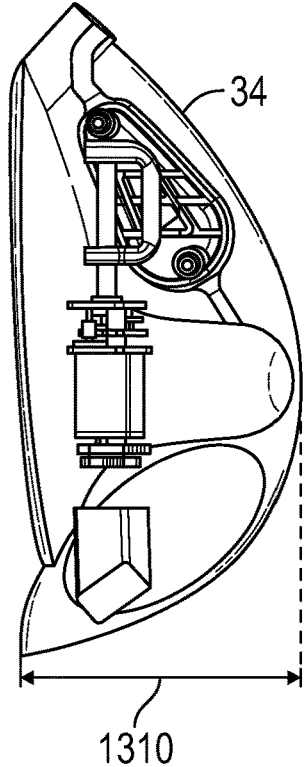
FIG. 13E illustrates a drive train for driving two compression members with one motor, according to an embodiment of the present disclosure.
Figure 13E:
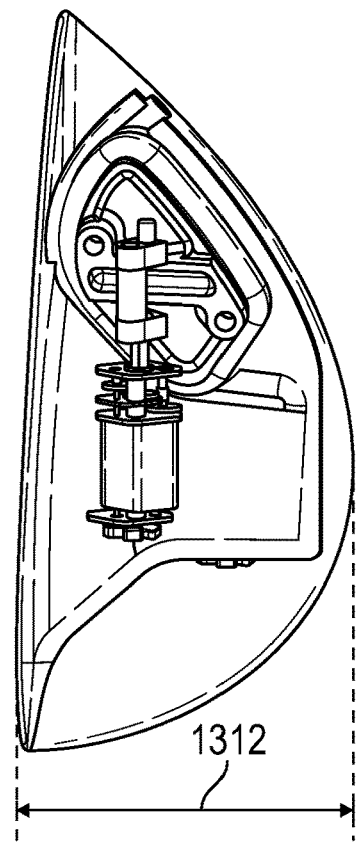
Figure 13E:
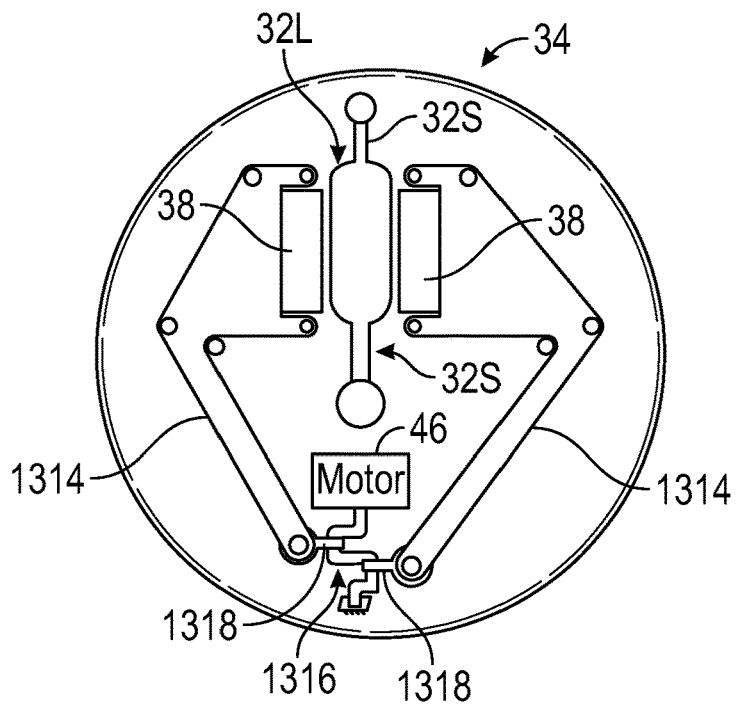

In order to reduce the overall length of the housing/main body 34, and thus the amount of distance by which the system 100 protrudes from the breast of the user, the compression chamber 32L can be made half as long (or otherwise shorter or smaller overall volume) and a second chamber 32L (which may be a duplicate, mirror image of the first, or other size) may be mounted on the opposite side of the housing as illustrated in FIG. 13A. A second compression driver 38 is configured to compress the second compression chamber 32L in the same manner as described previously. As a result, the overall length 1310 of the housing 34 (see FIG. 13C) is significantly shorter than the length 1312 of the housing 34 (see FIG. 13D) in a system employing only one compression chamber 32L, as shown in FIGS. 13B and 13D. Dual chamber embodiments can be driven by two motors 46, as illustrated in FIG. 13A, or alternatively, a drive linkage, such as a cable 1314, or a mechanical linkage providing scissoring action can be connected to a single motor 46 to drive both compression members 38. FIG. 13E shows an embodiment in which a single motor 46 is configured to drive both compression members 38 against and away from conduit portion (pump chamber) 32L. A drive train connecting the motor 46 to the compression members 38 includes a camshaft 1316, cables 1314 and linkages 1318 connecting the camshaft 1316 to the cables 1314. An advantage of this arrangement employing only one motor 46 and cables 1314 is that it creates flexibility between the pump chamber 32L and the motor 46. Thus the motor 46 can be placed anywhere in the housing 34 and the power can be routed as needed around any other structures to the location of the compression members 38 and pump chamber 32L. Alternatively, instead of cables, a pneumatic or hydraulic system could be used to add flexibility between the motor and pump chamber.

Although illustrated as being mounted on the right side of the housing 34, the driver 44 and compression member 36 could alternatively be mounted on the left side of the housing (same side as the driver 46 and compression member 38 in FIG. 1C). Because the forces required for closing the conduit section 32S with compression member 36 are less than the forces required for compressing conduit section 32L by compression member 38, a bearing is not required for mounting the free end of shaft 1052. A single cam 1054 is mounted on the shaft 1052 and is oscillated to drive against compression member 1054 to close off conduit section 32S (region 40) and, with reverse rotation, to pull away from the compression member 36 to allow conduit section 32S to reopen.

Figure 14A:
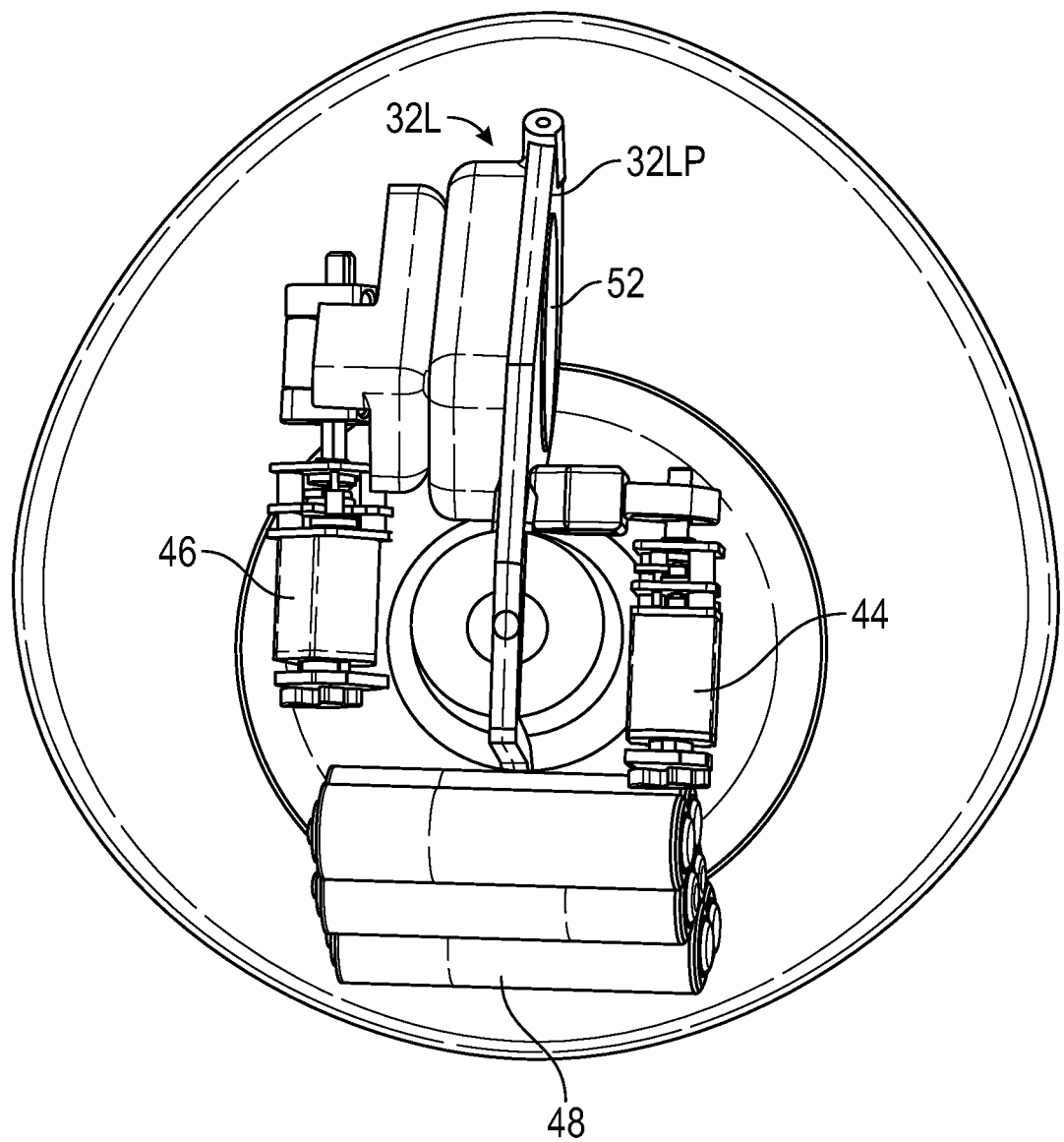
FIG. 14A illustrates a partial view of a pumping system according to an embodiment of the present disclosure.
Figure 14B:
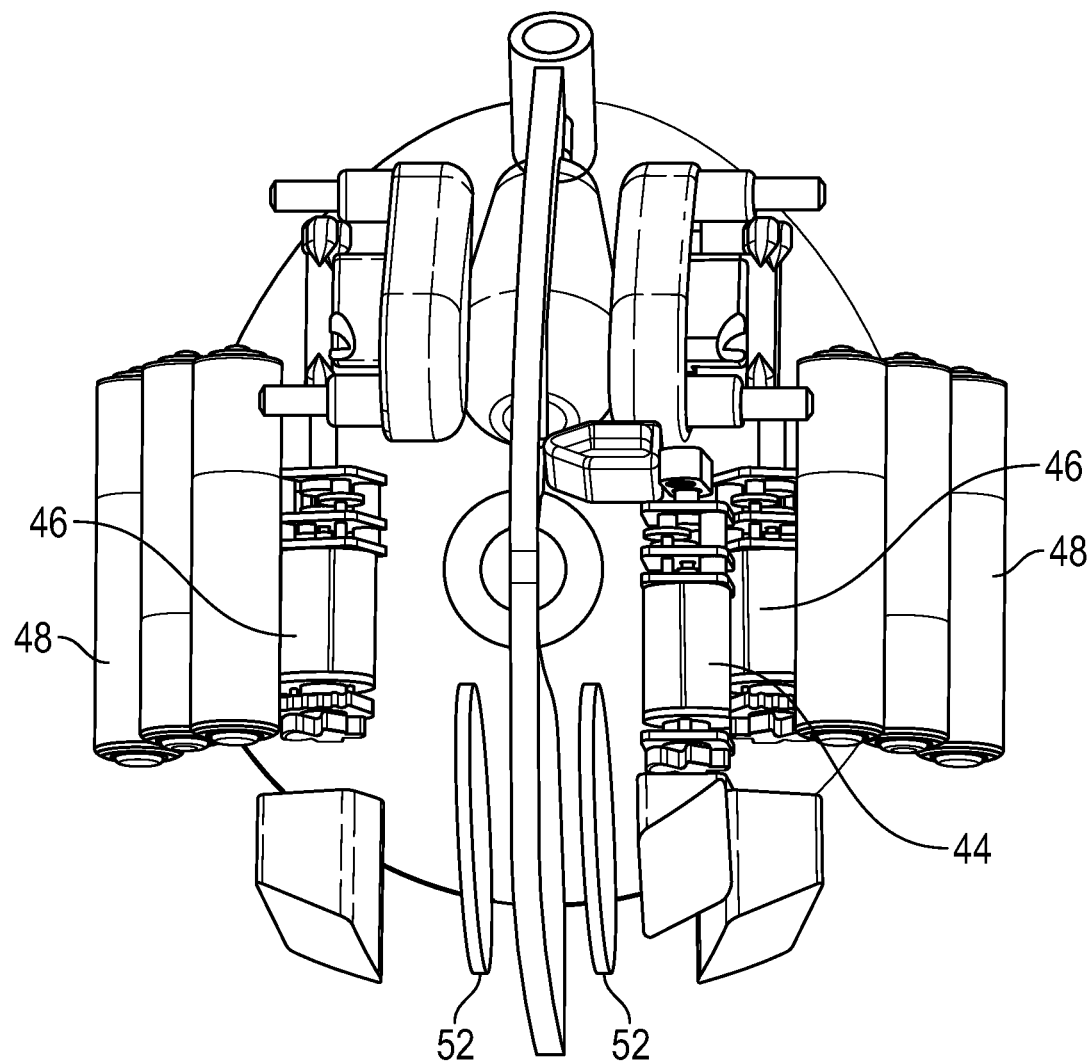
FIG. 14B illustrates a partial view of a pumping system according to another embodiment of the present disclosure.

FIG. 14A illustrates an embodiment of the present disclosure showing the control board (controller) 52 mounted on the external surface of the backing plate 32LP of conduit portion 32L. Although a single control board is shown, it is noted that controller 52 may include two or more controller boards, in this or any of the other embodiments described herein. One or more batteries (off-the shelf or custom) 48 are mounted on the lower portion of the main body 34, such as below motor 44 in FIG. 14A. FIG. 14B illustrates an embodiment of the present disclosure showing controller 52 having two control boards, mounted toward the bottom of the main body. In this embodiment, batteries 48 are mounted to the sides of motors 44 and 46.

Figure 15A:
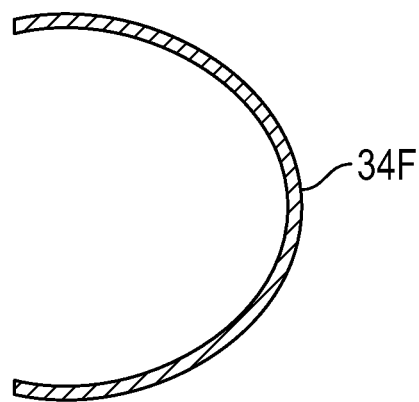
FIGS. 15A-15C illustrate longitudinal sectional views of various sizes of external shells that can be attached to a main body of a system according to embodiment of the present disclosure.
Figure 15B:
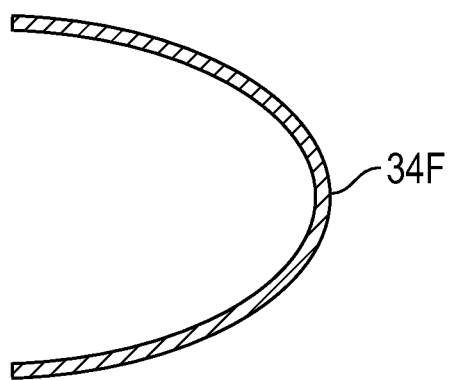
Figure 15C:
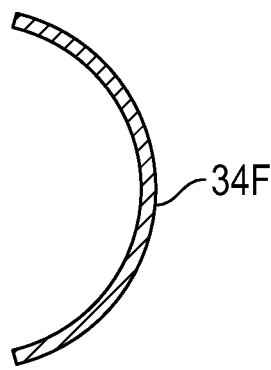

FIGS. 15A-15C illustrate longitudinal sectional views of various sizes of external shells 34F that can be attached to the assembly shown in FIG. 1B to provide an enclosed main body 34 and pumping section 30 like shown in FIG. 1A. Shells 34F can be made in various sizes and shapes that can be selected to best match the size and shape of the breast 2 of the individual user. For example, a user with a bra size of 36C may select a shell size like that shown in FIG. 15A, while a user with bra size 36D may select the shell of FIG. 15B and a user with bra size 34B may select the shell 34F illustrated in FIG. 15C. The present disclosure is not limited to those shapes and sizes shown in FIGS. 15A-15C, as many other sizes and shapes of shells 34F may be provided. Further, an optimized shape and size of shell 34F may be installed on the system 100 that has been optimized to fit the largest population of the user population, with or without the capability to change out the shell 34F for a more customized size and shape.

Figure 16A:
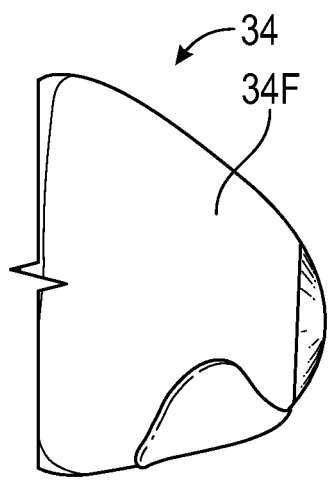
FIG. 16A illustrates a model of a main body of a system according to an embodiment of the present disclosure.
Figure 16B:
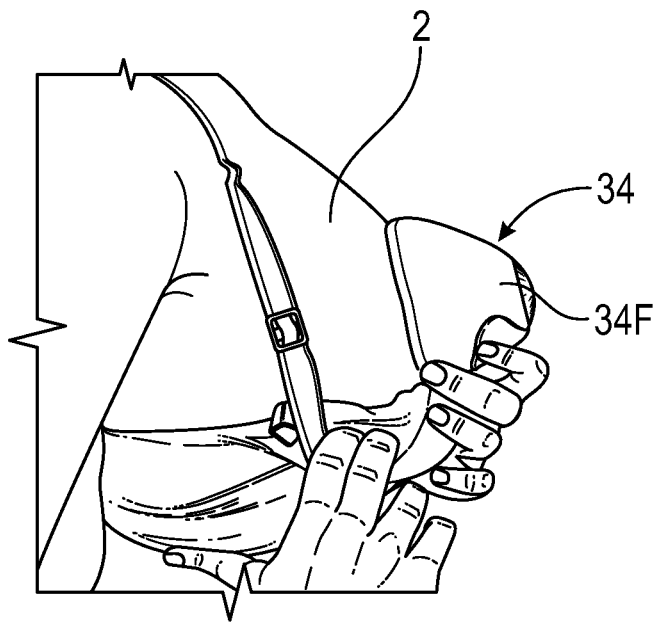
FIG. 16B shows placement of the model on the breast of a user, according to an embodiment of the present disclosure.
Figure 16C:
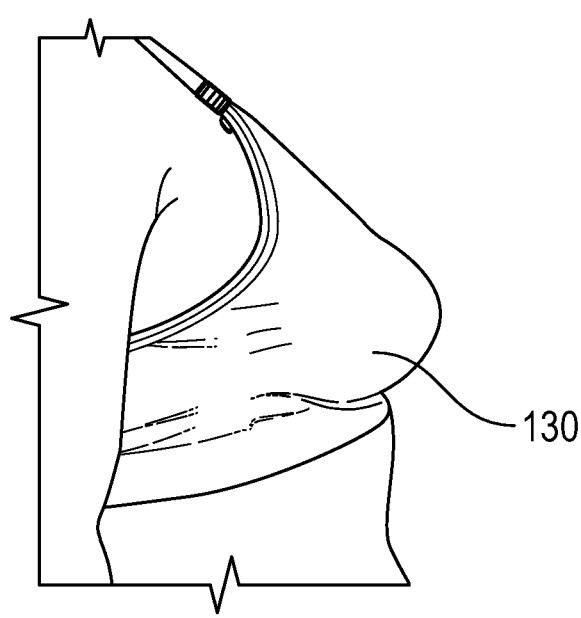
FIG. 16C shows the appearance of the model and breast when supported by a bra, according to an embodiment of the present disclosure.
Figure 16D:
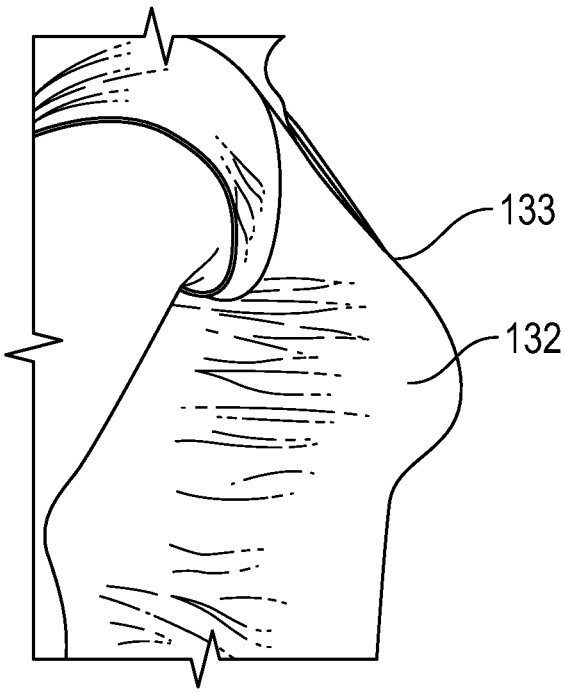
FIG. 16D shows the breast with the model installed, supported by bra, with a t-shirt being worn, according to an embodiment of the present disclosure.

FIG. 16A illustrates a model of the main body 34 of the system 100 with the proximal surface 34F having been contoured and sized to provide a natural appearance of the breast 2 when mounted on the breast 2, supported by a bra 130 and covered by clothing 132. FIG. 16B shows placement of the device/main body 34 on the breast 2 of the user. FIG. 16C shows the appearance of the device 34 and breast 2 when supported by bra 130. It can be observed that no unnatural looking bulges, bumps or discontinuities in the curvature of the breast are apparent. FIG. 16D shows the breast 2 with the device 34 installed, supported by bra 130, with a t-shirt being worn. The clothing (t-shirt) 132 follows a continuous, natural looking line of curvature 133 of the breast 2.

Figures 17A, 17B:
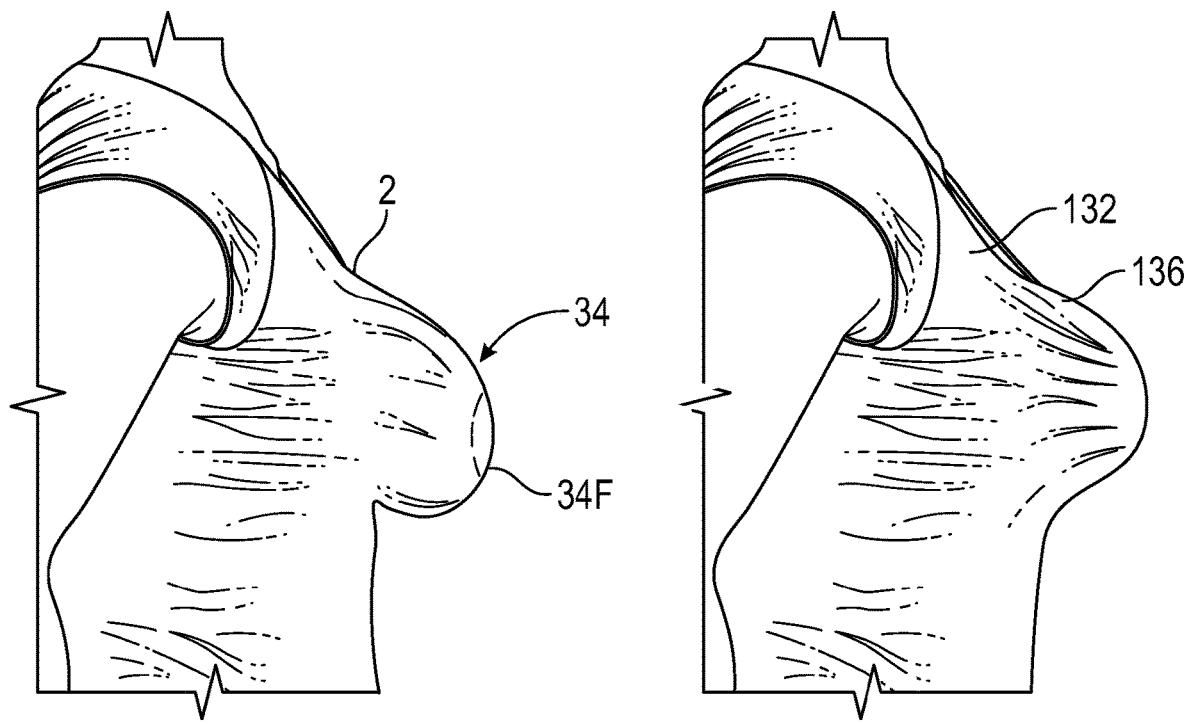
FIG. 17A illustrates an example in which form factor of the main body does not follow the contours of the breast.
FIG. 17B illustrates that even after donning a supporting bra and outer garment, the main body mounted to the breast is still noticeable as an unnatural contour.

For some users, the form factor of the main body 34 as supplied may not result in the natural, uninterrupted appearance of that shown in FIG. 16D. FIG. 17A illustrates one such instance in which the form factor of the main body 34 and/or proximal surface 34F does not follow the contours of the breast 2 as naturally as in the example described in regard to FIGS. 16A-16D above. FIG. 17B illustrates that even after donning a supporting bra and outer garment (e.g., t-shirt, blouse or other shirt or sweater type apparel), the existence of the main body 34 mounted to the breast is still noticeable as an unnatural contour resulting from the main body 34. In the example shown in 17B, a discontinuity, "notch" or "ledge" formation 136 is visible. The bra 130 worn by the user defines the available shape and geometry of the device (e.g., main body 34, milk collection container 60, etc.) as attached to the breast 2, even more than the breast does. In addition to, or alternative to changing out the shell 34F for a more customized size and or shape, a contouring flange 1810 may be provided to fill in the discontinuous region 136 to restore the natural contour lines and appearance of the breast 2.

Figures 18A, 18B:
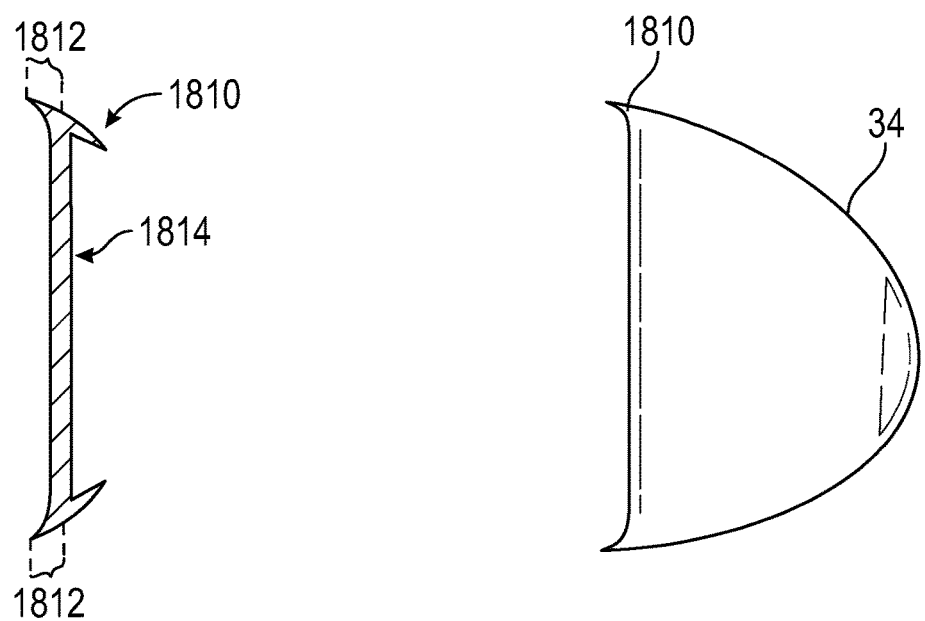
FIG. 18A is a cross-sectional view of a contouring flange according to an embodiment of the present disclosure.
FIG. 18B illustrates the contouring flange of FIG. 18A attached to a main body, according to an embodiment of the present disclosure.
Figure 18C:
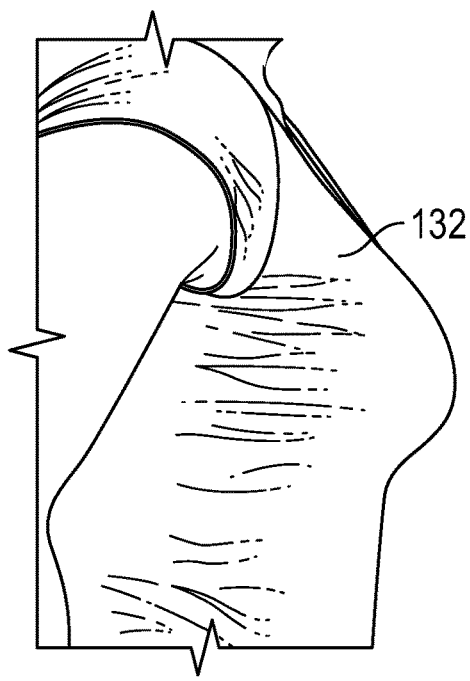
FIG. 18C illustrates the user shown in FIG. 17B after adding the contouring flange of FIG. 18A to the main body before fitting it to the breast, according to an embodiment of the present disclosure.

FIG. 18A is a cross-sectional view of a contouring flange 1810 according to an embodiment of the present disclosure. One or more flange portions 1812 extend from the main body 1814 of the contouring flange 1810 to extend distally from the main body 34 of the device when the contouring flange 1810 is attached to the main body 34, as illustrated in FIG. 18B. In this embodiment, the contouring flange 1810 is made to snap fit over the distal perimeter of the main body 34, but alternative means of joining a contouring flange 1810 with the main body 34 could be used, such as pressure adhesives, tape, or other equivalent that can releasably attach the contouring flange 1810 to the main body 34. The contouring flange portions 1812 do not necessarily need to form an airtight seal with the contouring flange 1810 if they are formed as one or more separate pieces, in which case the contouring flange breast component 1810 would form an airtight seal with the main body 34. Alternatively, the breast component of the contouring flange 1810 and contouring flange portions 1812 can be formed integrally and form an airtight seal with the main body 34 at the juncture of the components 1810, 34. FIG. 18C illustrates the user shown in FIG. 17B after adding the contouring flange 1810 to the main body 34 before fitting it to the breast 2. It can be observed that the natural contour lines of the user's breast have been restored as the t-shirt 132 worn by the user follows the natural contour lines of the breast. The flanges 182 taper proximally to form a smooth contour with the main body 34 and also taper distally to form a smoother transition with the breast 2 when the system 100 (main body 34 plus milk collection container 60, or alternatively, main body 34 without the collection container 60, in embodiments where the milk collection container is not mounted on the main body 34) is mounted on the breast 2, thereby making the system 100 less visible or noticeable when worn by a user. The flange 1812 is preferably, but not necessarily integrally formed with the main body 1814. The contouring flange 1810 is typically made of a compliant material, such as silicone, or any of the other alternative compliant materials listed above as used for making the conduit. Alternatively, the contouring flange can be made of a different material than those used for making the conduit, such as a more breathable material, like fabric or wicking material to help with heat management.

The flanges 1812 of the contouring flange 1810 of FIG. 18A extend at least from top and bottom portions of the main body 34 when attached thereto. The flanges may extend about arcs of the top and bottom portions of the perimeter of the main body in amounts within the range from about forty five degrees to one hundred eighty degrees (in embodiments where flange 1812 completely encircles the perimeter), typically within a range of about sixty to one hundred twenty degrees.

Figure 18D:
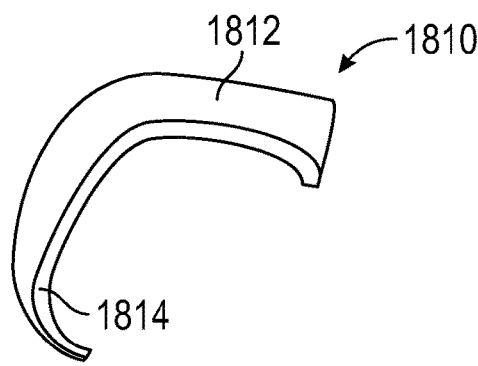
FIG. 18D illustrates a contouring flange according to another embodiment of the present disclosure.

Further alternatively, the flange 1812 may extend only from the top portion of the main body 34, as this is typically where the non-uniformity of the appearance of the breast 2 is more evident. In these embodiments, the main body 1814 may encircle the distal perimeter of the main body 34, or alternatively, may only extend around and attach to a top portion of the perimeter. FIG. 18D illustrates a contouring flange 1810 in which the main body only extends around the top portion of the distal perimeter of the main body 34 and flange 1812 extends only over a top portion of the breast 2. All embodiments of the contouring flange 1810 may be made in a series of sizes having different lengths of flange portions 1812 for further flexibility in matching the right amount of contour correction needed.

Figure 19A:
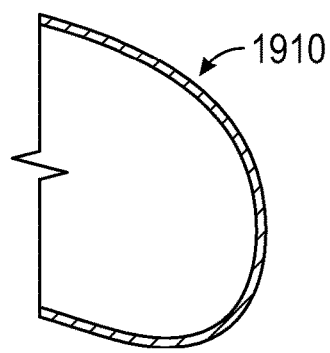
FIG. 19A illustrates a cross-sectional view of a contouring shell according to an embodiment of the present disclosure.

In addition to or alternative to the various fitting and contour correction solutions discussed above, a contouring shell 1910 may be provided to make the breast contour lines of the user appear more natural when the system 100 is attached to the breast 2 and the user is wearing clothing. FIG. 19A illustrates a cross-sectional view of a contouring shell 1910 according to an embodiment of the present disclosure. Contouring shell 1910 is made of a thin-walled, supportive material that defines an outer shape by the outer contour 1912 of the shell 1910 that is shaped with the natural contour lines of a breast 2. Shell 1910 may be produced in a variety of sizes and shapes to provide more flexibility in choosing the right shape and size for each particular user. Additionally, shell 1910 can be custom-molded to match the actual shape and contours of the breast of an individual user. The material from which shell is made may be any of those used for supporting bras 130, "push-up" bras, or the like.

Figure 19B:
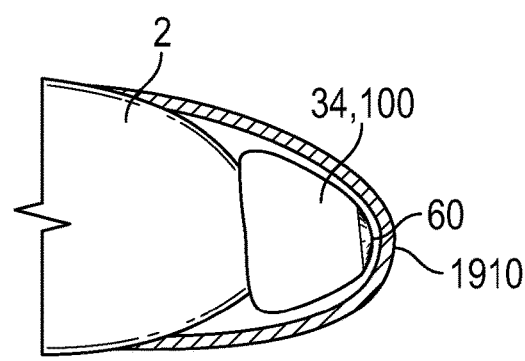
FIG. 19B illustrates use of a contouring shell by a user employing a system according to an embodiment of the present disclosure.

FIG. 19B illustrates use of a contouring shell 1910 (cross-sectional view of 1910) by a user employing a system 100 according to an embodiment of the present disclosure. The system 100 is completely contained within the shell 1910 and the shell 1910 provides the shape and contours of the natural breast 2 so that the user's shape appears natural when viewing the clothes worn by the user. Optionally, the user may place a second shell 1910 over the other breast 2, whether or not a second device 100 is placed over the other breast 2, to provide even more symmetry to the appearance of the breasts 2.

FIG. 19C shows a variant of contouring shell 1910 which is internally contoured to support the main body 34 and milk collection container 60 (when present). Contouring shell 1910 has a distal opening dimensioned and tapered to contact the breast 2 so that the outer surface of the shell follows substantially natural lines of contour of the breast 2 when worn. The internal surfaces 1912 are contoured at distal portions thereof to follow the contours of the breast 2 and then open up to a bowl 1914 that closely follows the contours of the main body 34. Thus, the bowl 1914 has a smaller radius of curvature that the radius of curvature of the portions of the inner surfaces 1912 distal to the bowl 1914 in the cross-sectional view of FIG. 19C. The contouring shell 1910, which may optionally be made of fabric, which may assist in cooling, sweat management (wicking), comfort, and provide a lighter weight solution, as compared to materials of the type discussed for making the conduit 32 and skin contact member 10. Examples of fabric that may be used include, but are not limited to: silk, wicking polyester blends, etc. Another advantage to using fabric is that it is easy to wash. In any material embodiment, the contouring shell looks natural before any milk has been pumped into the container 60, all the way up until the container 60 is full of milk and after the container 60 is full of milk. Contouring shell 60 will accommodate any changes in breast shape to keep a natural contour. Some embodiments of the shell 60 will be adjustable, as being stretchable (expandable and contractible) and/or having the ability to change angle (like rolling up a tube of paper into a cone shape, whereby many different angles/cones can be made according to the way the rollup occurs). In embodiments that can change angle, a releasable fastener 1918, such as hook and loop type fastener, snaps, adhesive, or other type fastener that can be readily attached detached, is provided so as to allow the user to fix the shell in a desired shape/angle. Further alternatively, or additionally, the contouring shell may be telescoping 1920, accordioned, or otherwise have the ability to slide to accommodate changes in breast 2 shape and/or container 60 volume as milk expressed, see FIG. 19F.

FIG. 19D is a cross-sectional view of a contouring shell 1910 according to another embodiment of the present disclosure, shown mounted on the breast of a user 2. In this embodiment, shell 1910 has a central opening 1916 at a proximal end thereof, through which a proximal portion of the main body 34 protrudes when the shell 1910 is installed thereon. The proximal end portion of the shell 1910 surrounding the opening 1916 forms a friction fit with the main body 34.

Any of the embodiments of contouring shell can be made very thin and need only be strong enough to support the drapage of clothing thereover. Examples of materials that may be used include, but are not limited to: plastic films, open or closed cell foams; lace material, or other polymers, including natural fibers.

FIG. 20 illustrates an embodiment of system 100 wherein two devices are used together, one on each breast 2 of the user. The controllers 52 of the devices can be wired together, or configured to communicate wirelessly (e.g., via radio communication) so that the controller 52 on one side can adapt functionality based in part on the current functioning of the device controlled by the other controller 52. For example, the controller 52 on the left side may communicate to the controller on the right side that the left side pump is in a milk extraction phase, at which time the controller on the right side pauses pumping until receiving a communication from the left controller 52 that the left side pump has paused, so that milk extraction occurs sequentially. Alternatively, the communication may be to coordinate simultaneous operation of the system pumps on both breasts. Simultaneous operation may be with the pumps on both sides pumping in phase, or out of phase by various amounts, wherein the controllers 52 coordinate the timing of the pump cycles on both sides. Given feedback from the pressure sensor 54 to the controller 54 of each respective device, the controllers can calculate a running total volume estimate of milk extracted from each breast 2. The controllers 52 communicate with one another, so that an overall total of milk extracted from both breasts can be calculated at any time. If the pumping mode being run has a total milk extraction volume goal for example, and one of the controllers determines that, when the current milk extraction total volume has reached a certain percentage of the total goal, but one of the breasts 2 has had 75% of the overall current total extracted, then the controllers 52 might cooperate to increase milk extraction from the second breast, while slowing down the pumping of the first breast, or pausing, for example. Each controller 52 can track pressure and milk flow rate. Where it is desirable to express substantially equal volumes of milk from each breast 2, the controllers 52 can coordinate to make sure that each breast 2 expresses substantially equivalent volumes of milk, before shutting down the system. Substantially equivalent volumes may be pre-designated in the software operated by the controllers to be within a range of 45%-55% of total milk volume expressed, 48% to 52% of total milk volume expressed, 50% of total milk volume expressed, or some other predetermined percentage or range of percentages. Some breasts 2 naturally produce different volumes of milk. The system may track production and determine expected values, as the volumes between breasts may not be the same. In this case, the system can execute similar logic to reach maximum or optimized expected production volumes for each breast, even when the expected volume of one breast is different than the expected volume for the other breast.

The controllers 52 may control the respective pumping sections 30 to "take turns" slowing or pausing on pumping section 30, while controlling the other pumping section to continue pumping, and vice versa. Further, one pumping section 30 may be a "slave" to the logic of the controller 52 of the other pumping section 30, allowing both pumping sections to be controlled by one controller 52 located in one of the devices. In such an embodiment, the "slave" pumping section 30 in the slave device receives control commands from the controller 52 located in the other device (master device) in the same manner that the controller 52 provides control commands to the pumping section in the master device. Likewise, sensor 54 in the slave device provides feedback to the controller 52 in the master device in the same manner that the sensor 54 in the master device provides feedback to the controller 52 in the master device.

Figure 21:
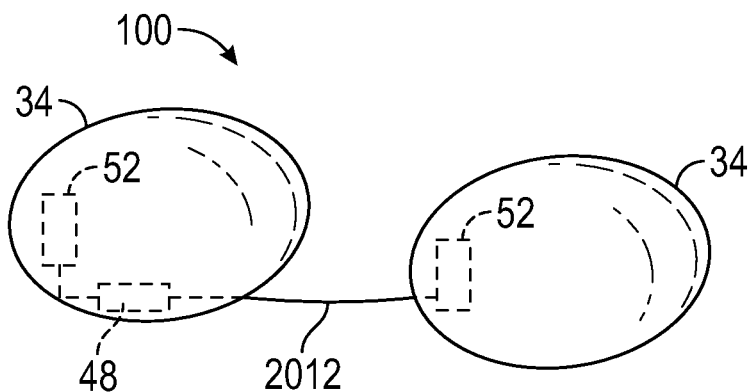
FIG. 21 illustrates a system wherein two devices are used together, according to another embodiment of the present disclosure.

FIG. 21 illustrates an embodiment of system 100 wherein two devices are used together, one on each breast 2 of the user, and wherein only one of the devices includes a battery 48, which is electrically connected to both devices to power both devices. The battery is internally wired to the components of the device on the left side and a wire or cable 2012 connects the battery 48 to the components of the device on the right side.

Figure 22:
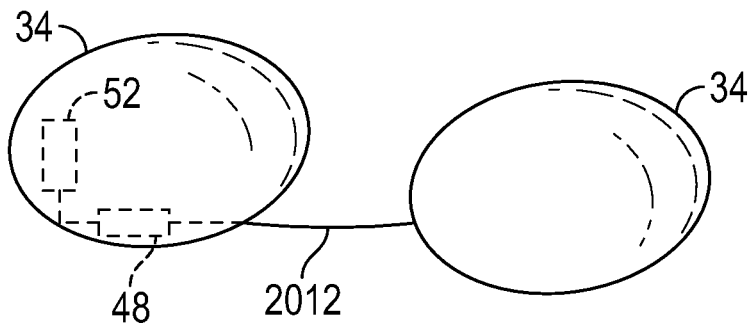
FIG. 22 illustrates a system wherein two devices are used together, according to another embodiment of the present disclosure.

Further alternatively, only one device may be provided with controller 52 and battery 48 to control both devices, as illustrated in FIG. 22. Although all of these examples show the master or controlling device to be on the left side, with the slave device on the right side, it would be readily apparent that the arrangements could be reversed, such that the master device appeared on the right side and the slave device on the left. Further alternative to FIG. 22, the battery 48 could be provided in the right side device and the controller 52 could be provided in the left side device or the battery 48 could be provided in the left side device and the controller 52 could be provided in the right side device.

Figure 23:
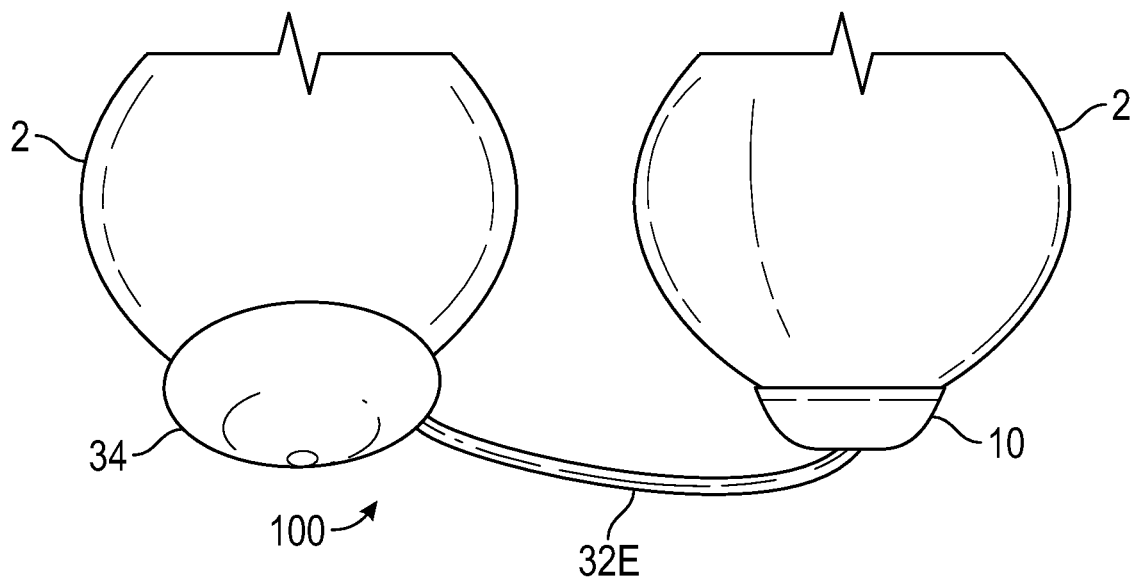
FIG. 23 illustrates a system in which a pump device is attached to one of the user's breasts and a skin contact member is attached to the other breast, according to an embodiment of the present disclosure.
Figure 24:
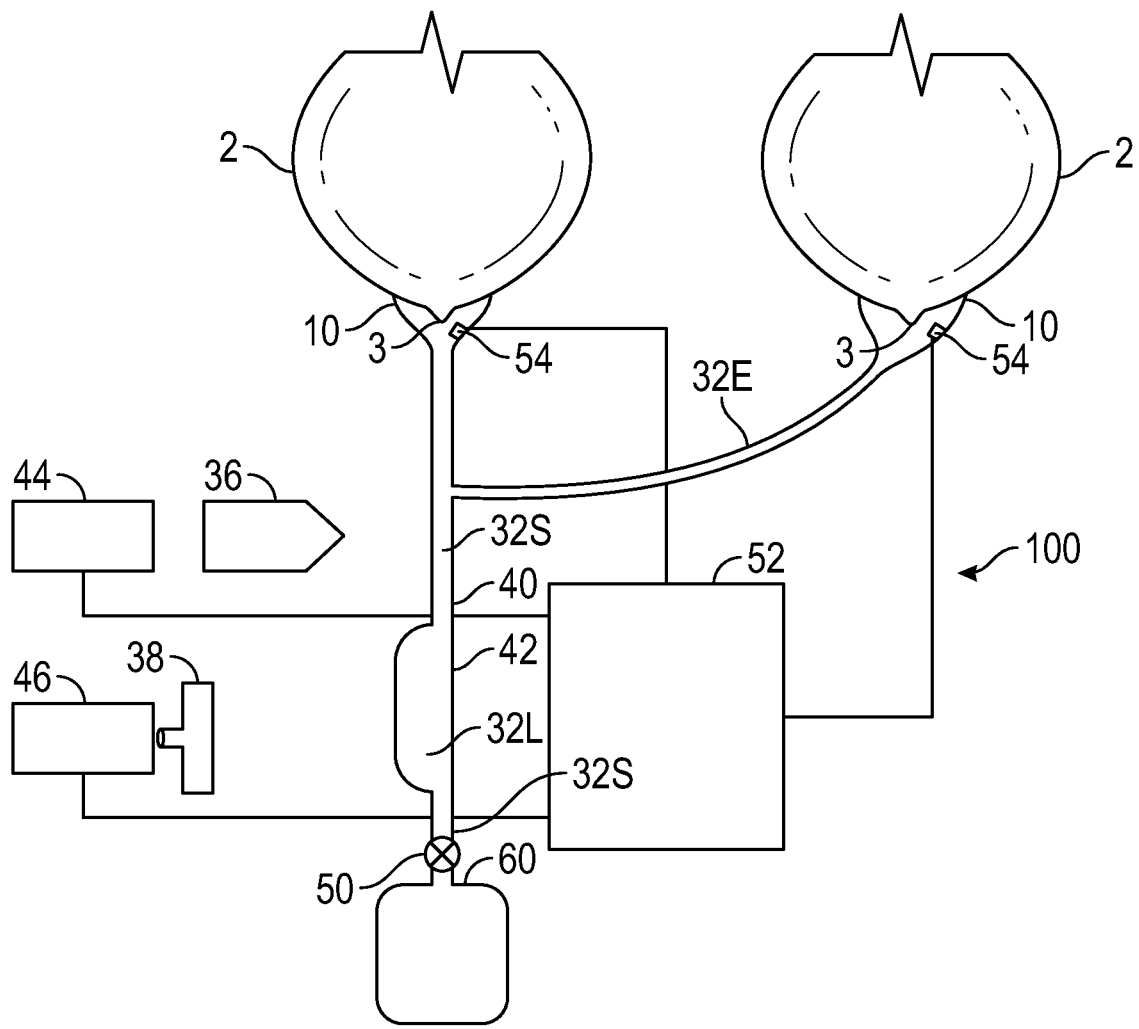
FIG. 24 schematically illustrates the conduit connections of the embodiment of FIG. 23 in more detail.

FIG. 23 illustrates a system 100 according to an embodiment of the present disclosure, in which a pump device is attached to one of the user's breasts 2 (user's right breast, left side of FIG. 23, but could be the opposite) and a skin contact member 10 is attached to the other breast 2. A conduit 32E which is preferably less compliant than regions 40, 42 connects the skin contact member 10 attached to the other breast 2 to the conduit 32 of the device. FIG. 24 schematically illustrates the conduit connections in more detail. The conduit 32E connects the stand-alone skin contact member 10 to the conduit 32 of the device, so that the compression members 36, 38 and drivers 44, 46 generate the pumping forces needed to extract milk from both breasts 2 simultaneously and pump the milk into a milk collection container in fluid communication with conduit 32S and one-way valve 50. Sensors 54 provided to both skin contact members 10, segments 16, or other location in the vicinity of the breasts 2, provide feedback to the controller 52. Based on pressure feedback readings from the sensors 54, and positions of the motors 46, 48 provided by feedback from encoders mounted on the motors 44, 46, controller 52 can calculate estimates of milk volume expressed from each breast 2.

Figure 25:
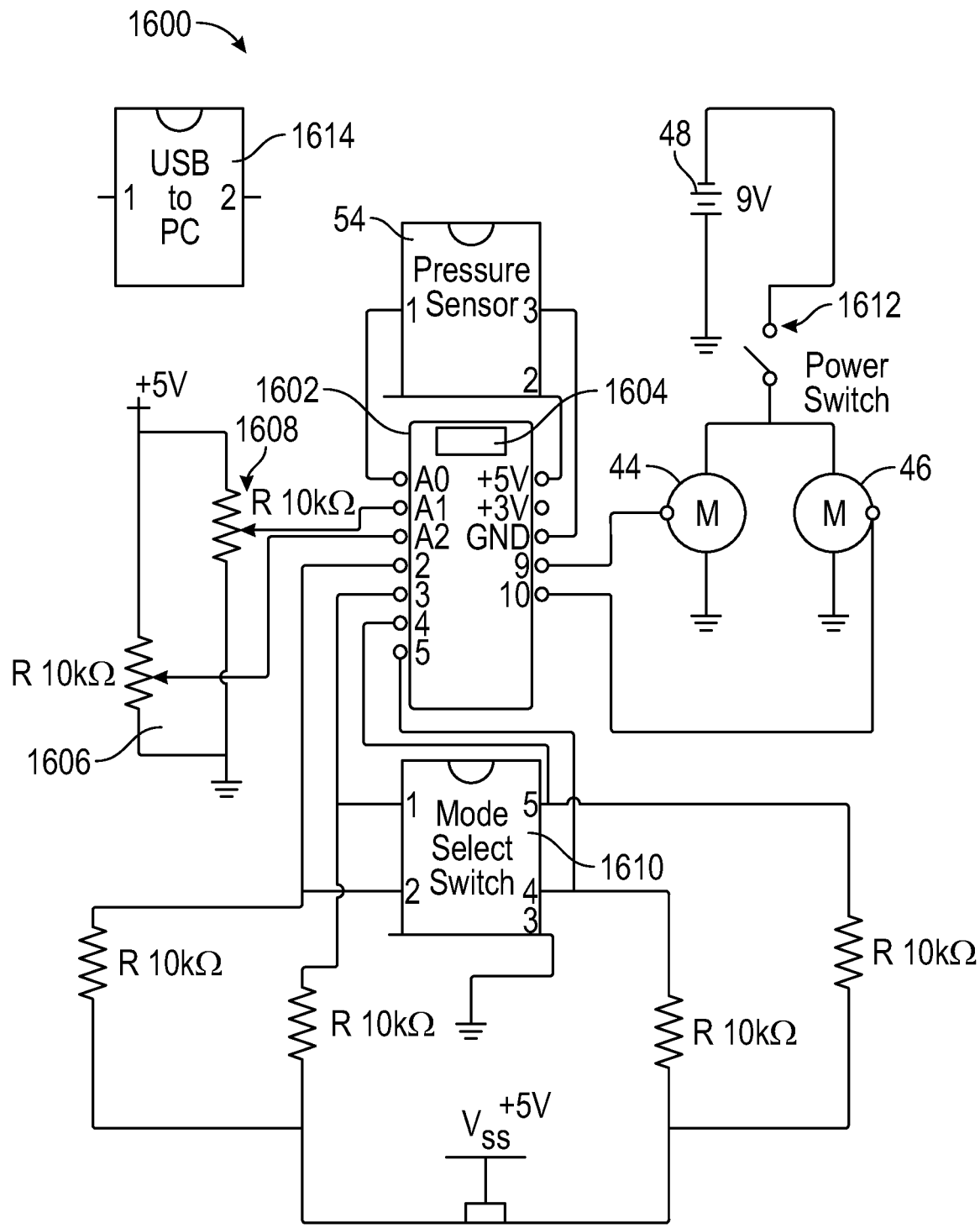
FIG. 25 shows a schematic circuit diagram of componentry used to control a system according to an embodiment of the present disclosure.
Figure 26:
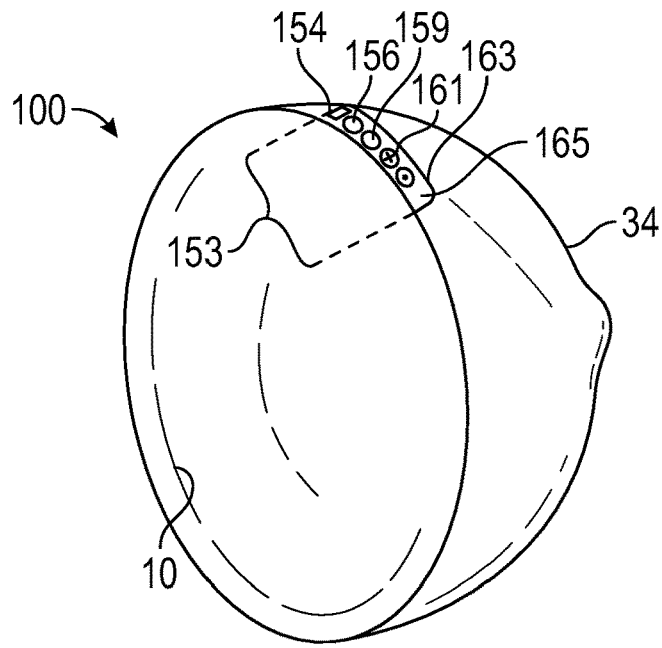
FIG. 26 is a perspective view of a device of the system according to an embodiment of the present disclosure.

FIG. 25 shows a schematic circuit diagram of componentry used to control system 100 according to an embodiment of the present disclosure. Controller 52 includes a microcontroller board 1602 (e.g., Arduino Mega 2560, or other microcontroller board of comparable functionality). A microcontroller processor 1604 is provided on board 1602 to process the control functions for reading pressure (and/or any other function being sensed, such as flow, or other function) and controlling the functions of the motors 44, 46, as well as monitoring speed, direction and positions of the motors 44, 46 and compression members 36, 38. A variable resistor/potentiometer 1606 (or digital equivalent) is provided for user input to adjust the maximum vacuum achieved during a cycle of a pumping profile. The user can adjust the potentiometer 1606, by selecting pumping force with the mode selector 156 and then increasing or decreasing pumping force by pressing either the "minus" button 161 or the "plus" button 162, respectively (see FIG. 26), until the desired force is attained. Optionally, the pumping force value could be displayed on the control panel 165 and/or could be transmitted by wire or wirelessly to be displayed on the display of an external computer 60 such as a smart phone, tablet, or other external computer. A second variable resistor/potentiometer 1608 is provided for user input to control the speed of the pumping, i.e., to adjust the period of the pumping cycle. The user adjusts potentiometer 1608 using mode selector 160 to go to speed mode and then increases or decreases the speed using the buttons 161 or 163. The mode selector button 156 also enables the user to select different modes/profiles of pumping performance by the system 100. Different profiles/modes can be selected by the user by operating the mode selector 156 to select one of the modes provided in the system and then pressing the "enter" or "select" button 159 to select the mode desired. The power switch 1612 is turned on and off by operation of power switch 154 by the user to connect or disconnect the battery 48 to or from the circuits. All of the above operations that can be performed by control buttons 154, 156, 159, 161, 162 and display 165 can alternatively or additionally be performed remotely, from an external computer such as a smartphone, tablet computer or other external computer communicating with the system 100 either by wire or wirelessly.

The system 100 provides integrated sensing via sensor 54 and processing of sensed signals by controller 52. This closed control loop enables a pump that is responsive to the user's breast milk flow. Although the system 100 can target latch (minimum) and maximum suction pressure levels, either through levels predefined in a selected pumping mode, or further modified by user selection in a manner described above, the rate of "slippage" from those pressure levels once hit correlates directly to the rate of milk expression. Since the volumes of the cavities defined by the conduit 32 and skin contact member 10/segment 16 are approximately known, the volume of milk being expressed can be calculated directly from the pressure drop measured by the system via pressure sensor 52. This data may be usable to dynamically vary targeted pressure levels for latch and maximum on a cycle-by-cycle basis, vary the suction cycle frequency and vary the rate of change of pressure between cycles. This dynamic ability to real-time adjust the pumping program is unique and heretofore unknown. Because of the dynamic adjustability, a defined "let down" mode or cycle becomes unnecessary, as the pump dynamically adjusts the cycles as the milk begins to flow. Further, by providing real time pressure feedback to the controller 52, the controller 52 can calculate rates of milk flow as noted above. If the calculated flow rate falls below a predetermined flow rate (after initial let down and after the predetermined flow rate or a second predetermined flow rate has been exceeded), then, in one example, the controller 52 can pause the pumping cycle to allow further internal flow and buildup of milk in the breast 2 for a predetermined pause time, and then resume the pumping cycle. This "refill" or "refractory" period provided by the pause may ultimately lead to greater and/or faster milk yields than by pumping continuously and not letting the breast 2 rest to refill/recover during pause times without pumping. The pumping cycle can be continued if the milk flow rate returns above the predetermined flow rate, with a pause again being initiated upon falling below the predetermined flow rate again. Further, the controller 52 may be programmed such that the falling below of the predetermined flow rate needs to be met for a predetermined consecutive number of pump cycles before the pause is commenced, or the predetermined flow rate may be an average predetermined flow rate averaged over a predetermined number of pump cycles.

Different types of pumping modes that may be stored by the controller include those examples disclosed in Application Ser. No. 62/050,810, but like that application, the present disclosure is not limited to those modes. Additional modes are described below, but the present disclosure is not limited to only those modes described, as a virtually unlimited number of different pumping modes could be programmed, although of course, only a finite number of such modes will typically be stored by the system 100. A "sleep" mode or "nighttime" mode could be provided which, when selected, allows the user to select a time in the near future when the system 100 will power up and begin a pumping session. This allows the user to attach the system and go to bed, as the system will begin the pumping session at the selected time, whether the user is asleep or awake. Typically, but not necessarily, the sleep mode may have a lower maximum suction that other selectable daytime modes, and may have a shorter session time, pumping only for a shortened time period sufficient to relieve pressure buildup in the breasts 2 which might otherwise cause discomfort and even disruption of sleep. The pumping profile of the sleep mode can be gentler than daytime modes, for example having lower maximum suction pressure and/or shorter hold periods at maximum suction pressure during the pumping cycles, with the goal being not to wake the sleeping user while the user is laying on her side or back.

Figure 43:
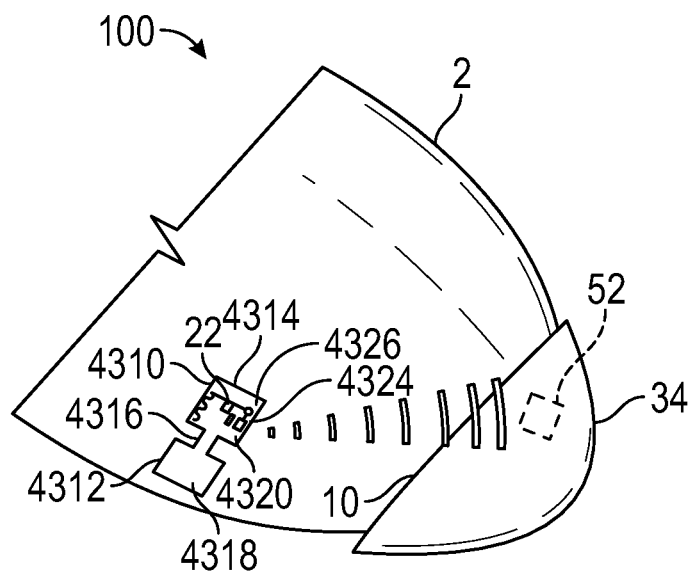
FIG. 43 illustrates a system including a sensor adhered to the breast of a user, according to an embodiment of the present disclosure.

Alternatively, or additionally, when in "sleep" or "nighttime" mode, the system 100 may also be able to sense when one or both breasts 2 are "full" by receiving inputs from a sensor 4310 attached to the breast 2 (see FIG. 43) of a type described in U.S. Application Ser. No. 62/050,902, filed Sep. 16, 2014, which is hereby incorporated herein, in its entirety, by reference thereto. On embodiment of sensor 4310 (other embodiments as disclosed in Application Ser. No. 62/050, 902 may be used) as shown in FIG. 43 is configured to be adhered to the skin of the breast 2 and is adhered to the breast 2 as shown in FIG. 43, to detect expansion and contraction of the skin. Device 4310 includes a distal mount portion 4312, a proximal mount portion 4314 and a flexible intermediate portion 4316 that bridges the proximal 4314 and distal 4312 mount portions. The proximal mount portion 4314 has components mounted to it that measure changes in the skin that the device 4310 is adhered to. The back surfaces of the distal and proximal mount portions 4314, 4312 have an adhesive 4318 applied thereto so that the device 4310 can be adhered to the skin, while the intermediate (bridge) portion 4316 does not have any adhesive applied thereto, so that it can more freely expand and contract. There are various ways that the device 4310 can be configured. In one preferred embodiment, an elastically expandable material (silicone, or any number of elastomers) can be used for all portions 4312, 4314 and 4316, in order to render manufacturing easier and relatively less costly. Attached to or embedded within the portions 4312 and 4314 can be a reinforcing structure (e.g., a weave or non-expandable plastic or fabric), which renders the portions 4312, 4314 resistant to deformation. Additionally or alternatively to providing a reinforcing structure, the adhesive by which the portions 4312, 4314 are attached to the skin may provide or supplement the function of providing resistance to deformation. Alternatively to making all portions 4312, 4314, 4316 of the same material, composite materials can be chosen so that the composite material provided for portions 4312, 4314 could include non-elastomeric material encased by or otherwise attached to elastomeric material, which may be the same as, or different from the elastic material used to form portion 4316. Elastomeric materials may include, but are not limited to, one or more of silicones, polyurethanes, polyether block amides (PEBAX), polyethylene terephthalates (PET), polyethylenes, high density polyethylenes (HDPE), low density polyethylenes (LDPE), polyamides and/or other biocompatible thermoplastic elastomers. Materials that can be woven as reinforcing fabrics include, but are not limited to, one or more of: polytetrafluoroethylenes (PTFE), polyesters, polypropylenes, polyethylenes, para-aramid synthetic fibers and/or other biocompatible polymers used for making woven fabric. Non-expandable, or non-elastomeric materials that may be used include, but are not limited to, at least one of: acrylonitrile butadiene styrene (ABS) plastics, polyester fiberglasses, high density polyethylenes (HDPE), high impact polystyrenes (HIPS), nylon, polybutylene terephtalates (PBT), polyethylene terephthalates (PET), polycarbonates and/or other biocompatible, thermosetting polymers or none-expandable, non-elastomeric materials. Woven fabrics used may have either elastomeric or rigid properties depending on how they are configured and could therefore be used in portions 4312, 4314 or portion 4316, depending upon configuration for elastomeric properties or rigidity properties. Adhesives that may be used to adhere the portions 4312, 4314 to the skin include, but are not limited to, at least one of: pressure sensitive adhesives of the type used in ostomy applications, containing various rubber-like organic molecules such as polybutadiene and polyisobutylene, polyacrylate pressure sensitive adhesives, silicone adhesives, soft skin adhesives (Dow Corning®), skin friendly adhesives (Scapa Healthcare, Windsor, Conn.), removable adhesives (an adhesive designed to stick to a substrate without edge lifting that can be removed without damage to either the label or the substrate, such as available from Avery Dennison), and/or any other adhesive successfully used for temporary adherence to the skin.

Figure 44:
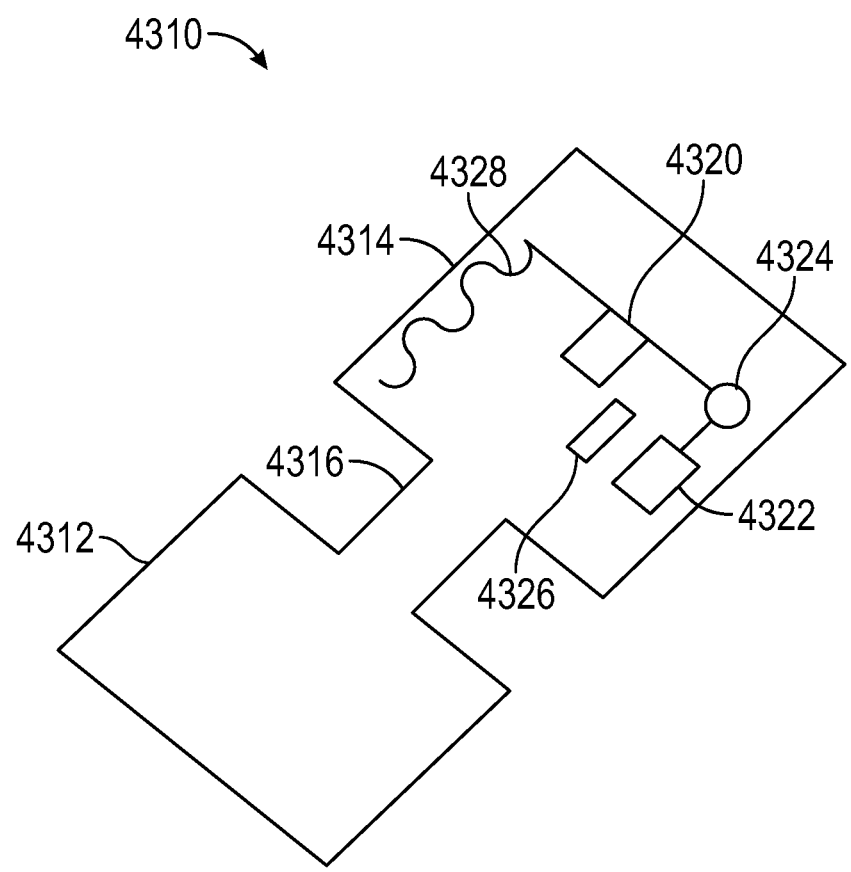
FIG. 44 is a detailed view of the sensor of FIG. 44.

The distal and proximal mount portions 4312, 4314 are adhered to the skin at locations that initially place the bridge portion 4316 in an unbiased stated (neither stretched nor compressed). A sensor 4320 (see FIG. 44), such as an electric resistor, strain gauge, magnet or the like is provided on proximal mount 4314 and is configured so that compression and expansion of the bridge portion 4316 applies strain/forces to the sensor 4320, which measures the amount of expansion or compression according to methods well understood in the strain measurement arts. In the embodiment shown in FIGS. 43-44, a circuit 4322 is provided on proximal mount that is powered by battery 4324 and can be configured to process the output of the sensor 4320, and optionally, store the processed signals in optional memory 4326. Additionally, an antenna 4328 is electrically connected to the circuit 22, which can be used to transmit the data stored in memory 26 (or directly transmit, if memory 26 is not provided) to controller 52, which uses the stretch/contraction data to calculate an estimate of the volume of the breast 2 to which the device 4310 is adhered. Controller 52 can be programmed, when in sleep mode, to initiate pumping when the estimated breast calculated is greater than or equal to a predetermined breast volume that is considered to be "full", or sufficiently full that breast pumping is needed to relieve discomfort that would otherwise increase in the breast 2 of the sleeping user.

Figure 27:
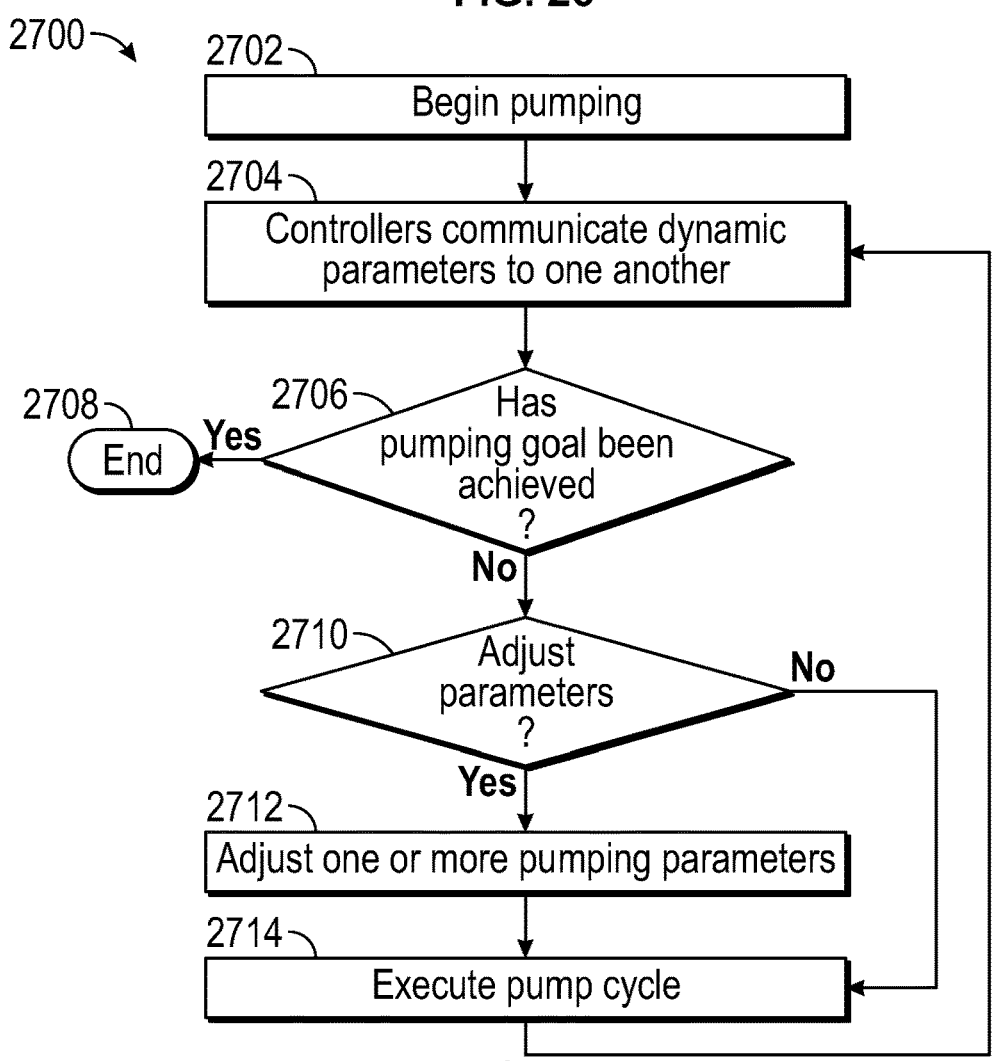
FIG. 27 illustrates events that may be carried out in a coordinated operation of breast pumps on both breasts using a system according to an embodiment of the present disclosure.

FIG. 27 illustrates events 2700 that may be carried out in a coordinated operation of breast pumps on both breasts 2 using a system 100 according to an embodiment of the present disclosure. After attachment of the system 100 to both breasts 2 such that a main body 34 pump is attached to a first breast and a second main body pump 34 is attached to a second breast and a pumping mode has been selected for both pumps (typically the same mode for each) the pumping session begins at event 2702 with pumping cycles being applied to both breasts. At event 2704, the controllers 2704 communicate dynamic parameters specific to the particular breast pump being controlled to each other. Dynamic parameters may include any combination of the following, but are not limited to: maximum suction pressure, latch (minimum) suction pressure, cumulative volume of milk, volume of milk expressed in most recent cycle, milk flow rate, etc.

At event 2706, each processor 52 determines whether a pumping goal for the current pumping session has been achieved. There may be multiple pumping goals, in which case all pumping goals must be achieved before ending processing at event 2708. In the simplest example, if there is only one pumping goal, the pumping goal may be any of, but not limited to: elapsed time, cumulative milk volume or minimum flow rate after first exceeding a predetermined flow rate. If the goal(s) has not yet been achieved at event 2706, then at event 2710, the controllers determine whether adjustment of one or more pumping parameters is needed to be applied to the pumping mechanisms 30 that it controls, based on the current dynamic parameters of both its pumping session, as well as the current dynamic parameters of the pumping device operating on the other breast. One or more parameters may need to be controlled, for example, if one breast has expressed more than a predetermined percentage of the current cumulative total of milk expressed, in which case, the pump for the higher producing breast may be modified to slow the pump cycle, lower the maximum suction pressure level, increase one or more pause times in the cycle, and/or make some other parameter modification. Alternatively, or in addition thereto, the controller for the pump on the lower producing breast may speed up the pump cycle, raise the maximum suction pressure level, decrease or increase one or more pause times in the cycle, and/or make some other parameter modification. If no adjustments are needed, or after one or more adjustments are made at event 2712, the next pump cycle is executed on each pump. The processing returns to event 2704 where the communication between controllers 52 is again carried out.

Figure 28:
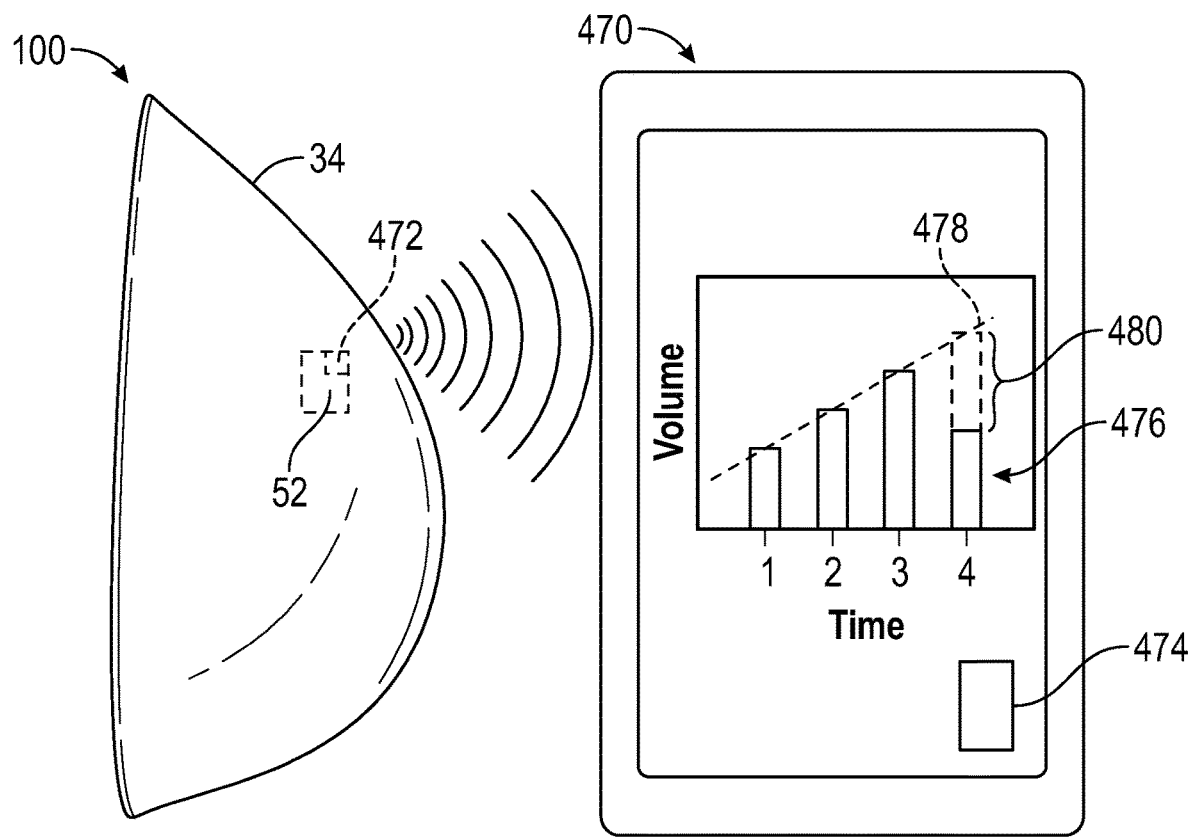
FIG. 28 is a schematic representation of transfer of data wirelessly from a controller to a smartphone, according to an embodiment of the present disclosure.

The breast pump systems 100 according to the present disclosure may be designed with the capability of communicating to an external computer which may be, but is not limited to: a smartphone, a tablet computer, a laptop computer, a notebook computer or a server. FIG. 28 is a schematic representation (not to scale) of transfer of data wirelessly from controller 52 to smartphone 470. Controller 52 may include a wireless transmitter 472 that can be actuated by the user via controls 156, 158, 161, 163 to send data to the external device 470 at will, as long as the external device 470 is in range of the transmitter 472. Alternatively, or additionally, a hard wire connection may be provided to send the data over the hard wire to the external device 470. Further alternatively, controller 52 can be provided with a BLUETOOTH® transmitter, so that data is automatically transmitted to the external device 470 whenever the external device 470 in range of the BLUETOOTH® transmitter. Further, the controller 52 may be configured to automatically transmit signals to the external computer 470 whenever the external computer is in sending range of the controller 52 and the controller has any date that needs to be sent, but has not yet been sent. Likewise, automatic receiving of signals could be configured similarly. Further, the external computer 470 may be provided with an app 474 that is configured to allow the operator of the external computer 470 contact the controller and establish communications from that end. Still further, controller 52 can be configured to automatically upload data to a server in the cloud and/or upload data to the cloud when instructed to do so by the user using controls 252. The uploaded data can then be used or shared in group studies of the data. Further, the external device 470 may be capable of downloading other customized programs for use with the breast pump system, which could be updated by crowd sourcing results from other mothers, etc. The uploaded data could also be useful for insurance companies or other entities having permission under the Affordable Care Act (and/or the user's permission) to use the data.

Figure 29:
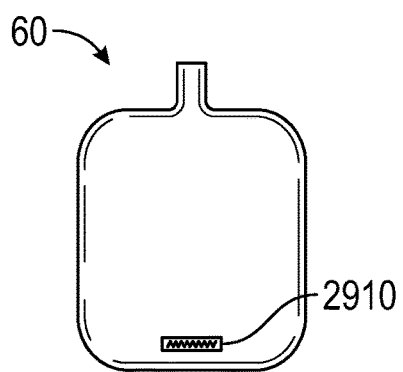
FIG. 29 illustrates a milk collection container with a barcode or QR code, according to an embodiment of the present disclosure.

The external device 470 can be provided with software (either in app 474, or in another program) to customize pump functions based on data received from the controller 52, to calculate volume of milk extracted, to track expression efficiency and monitor it over time (within a single extraction session, as well as over multiple extraction sessions), keep track of inventory of previous expression sessions, dates of the sessions, and the specific containers 60 used in each individual session. FIG. 29 illustrates a milk collection container 60 provided with a barcode or QR code 2910 that is scannable by the external computer 470. By scanning the barcode or QR code 2910 into the app 474, the app logs that number of the barcode or QR code in and tracks it relative to all other milk collection containers. If the scanning is done, preferably sequentially with respect to the bags, but in any other order that identifies and correlates specific milk containers 60 each to unique numbers or other identifiers (and preferably to date and time of extraction as well), the app 474 can track the ages of the milk collected and direct the user as to an order in which the containers 60 should be used for consumption by the baby. By indicating a particular bar code or QR code (or number associated therewith) to the user for the next milk collection bag that is suggested to be used for the next feeding, the user can go into the cooler and locate the specific milk collection container 60 to be used. This provides more order and efficiency to the manner in which the extracted milk is consumed and lowers wastage by ensuring that the milk containers 60 are used in the best order. This tracking can be useful for reminders to use the containers of milk 60 with a specified time, and can organize order in which the containers are to be used (e.g., first-in, first-out, or other scheme). Pump functions can be customized by varying suction levels, altering suction waveforms (amplitude and duration of application of suction), phases of extraction or feeding times, rest programming, heating temperatures and times, vibration frequency and duration, etc. Also the battery level can be monitored and a warning provided when the battery reaches a predetermined low level of charge. The external device may also use the display 478 to display one or more photos of the mother's baby during an extraction session to increase the emotional and physical reinforcement to simulate what is provided when the baby is actually feeding.

By receiving the pumping data from the controller, the app 474 can compile histograms 476 and display them on the display of the external computer 470. In the example shown in FIG. 28, a histogram 476 of milk extraction volume is shown that plots milk volume per time, where the time scale may be in days, weeks, sequential milk extraction sessions or other unit of time, in a time sequential order, so that trends in milk volume needs of the baby can be visualized. The trend line 478 in FIG. 28 establishes the milk volume deficit 480 that needs to be supplemented to the baby in month 4. Because of the capabilities of the system 100 and control feedback loop including the controller 52 and pressure sensor 54, the data that is transmitted can be done automatically, and the milk extraction volumes can be calculated, either by the controller 52 or by the processor running the app on the external computer 4790, so the user does not need to manually enter the milk extraction volume values, time or date values, or other pump cycle data into this tracking system, as it can all be taken care of automatically.

Figure 30:
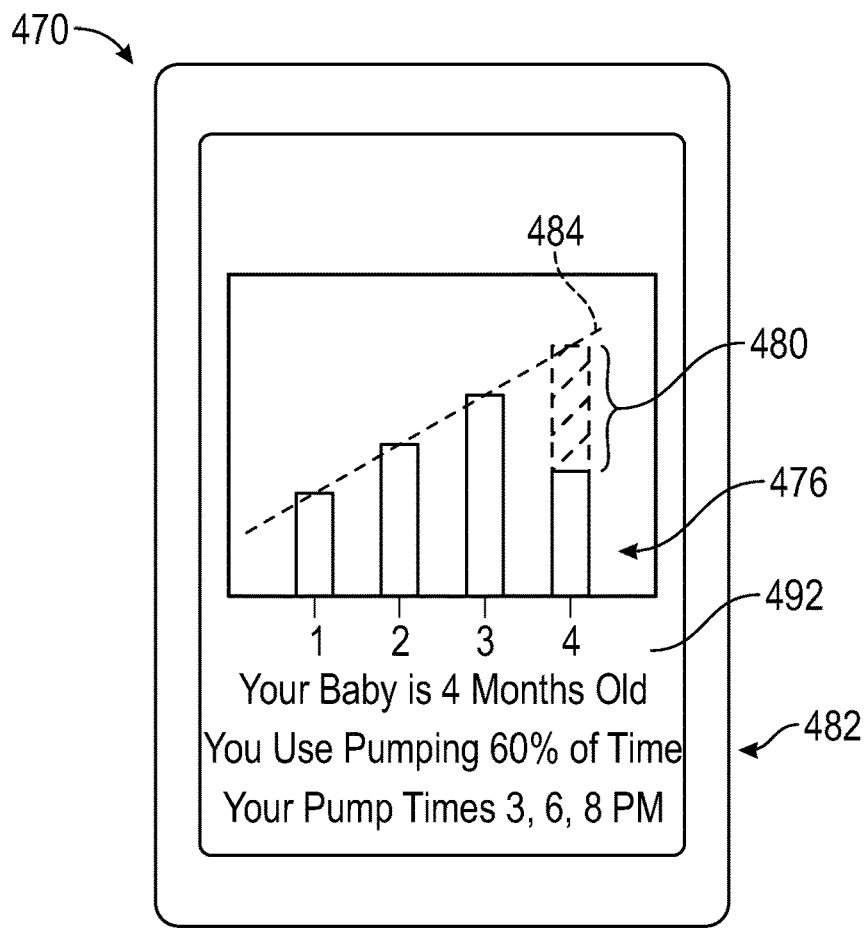
FIG. 30 illustrates a histogram displayed on an external computer, according to an embodiment of the present disclosure.

In addition to providing data graphically, such as in histogram 476 form, or providing tabular data, the app 774 can also display recommendations based upon data received. For example, the user can input the baby's date of birth so that the app can keep track of the baby's age. Based upon the baby's age and a national trend line 484 of babies' milk consumption needs, combined with a knowledge of what percentage of total breast extractions sessions are done by pump (which may be inputted by the user), the remaining being natural sessions with the baby feeding directly, and other food, if any, including formula, cow's milk, solid food etc., that is consumed by the baby (as also inputted by the user) the app can plot the breast extraction volumes, as scaled by the percentage done by pump extraction, against the national trend line 484 of total milk volume needs per the age of the baby, and determine if the mother is pumping sufficient volumes of milk. In the example of FIG. 30, there is a deficit 480 at month 4. The app in response to this deficit, can recommend changes to the pumping routine, such as additional or different times for pumping, longer pumping sessions and/or different pumping modes to try. If it is known that the baby is supplementing with formula or starting solid food, the app can adjust accordingly the expected milk volume extraction levels, frequency of pumping expected, alert levels, etc.

Additionally, an interactive feature of the app may request input from the user when a downtrend is seen in milk extraction production, as to whether the mother is weaning. If the mother answers yes, the app can suggest a weaning pumping schedule, as a change to the current pumping routine that the mother is practicing.

Periodically the app 474 may prompt the user to provide information in the form of a questionnaire, which can be written or oral, in order to update the current status of the baby's feeding routines. Inputs for information such as whether the baby has begun supplementing with formula and how much, whether the baby has started on solid food and, if yes, how much, baby's weight, baby's length/height.

Through the buttons on the device or through a remote app in direct communication with the pump information regarding the age of the baby, the mom's goals (i.e. NICU feeding versus a 1 year old feeding) and other information could be used to vary how the pump responds to the pressure/volume feedback it receives. For a mom whose baby is in the NICU, expression will be small and may take more time—in this case a gentler cycle that continues for a much longer time with little expressed would be expected—whereas a mom with a 1 year old baby would have a much more dynamic cycle and as expression slows the pump would be programmed to shut down relatively soon after that is detected. The combination of "knowledge" of the situation the mom is in (baby age, etc., personal goals—working mom vs. nighttime loading), plus the information gained from the sensor give the pump the ability to truly be matched to its user and learn over time.

Figure 31:
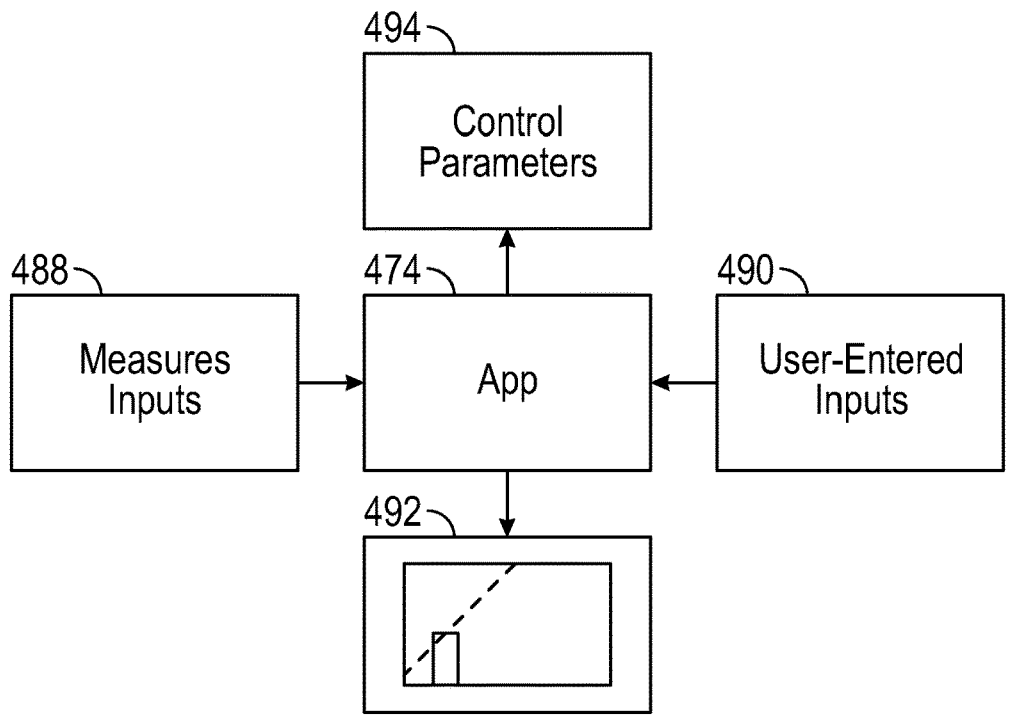
FIG. 31 schematically illustrates data inputs that are received by an app/software of an external computer, used to evaluate, track and manage breast milk expression using a system according to an embodiment of the present disclosure.

FIG. 31 schematically illustrates where data inputs are received by the app/software 474 used to evaluate, track and manage breast milk expression using system 100. Measured inputs 488 are inputted to app 474 by the one or more controllers 52 of the system 100, either by a wired connection or (preferably) wirelessly transmitted. Measured inputs may include, but are not limited to, at least one of: length of pumping session time, time of day at which pumping session was initiated, milk volume expressed during the pumping session, pumping session frequency (e.g., how many times per day is pumping done), pressure waveforms for the pumping cycles applied, maximum suction pressure applied, latch suction pressure applied, flow rate, etc. User-entered inputs 490 may include, but are not limited to, at least one of: baby's weight, baby's birthdate, percentage of baby feedings that result from the milk expressed by pumping (as opposed to natural, direct breastfeeding by the baby), pumping goals (e.g., build up, to increase volume per pumping session; maintenance, to keep volume per session relatively the same; weaning, to gradually decrease volume per session, baby in neonatal intensive care unit (NICU) and breast pumping is just being started by the new mother, etc.), mother's age, which "feeding" the pumping session is taking over, how many feedings per day (specified by breastfeeding or pumping session), time of day, whether a target volume of expressed milk per breast is desired, or a target timeframe for pumping, etc.

The inputs 488, 490 are processed by the algorithms of the app 474 and information is displayed on the display 492 of the external computer 470 for reading by the user. The user can confirm the conclusions reached by the app in terms of expected milk expression outputs, breast pumping frequencies, frequency of breast pumping sessions, expected lengths of breast pumping sessions, etc., by providing feedback to such through an input capability of the external computer 470. Alternatively, the user may want to modify one or more aspects of the conclusions displayed, and can do so by inputting desired changes through the input capabilities of the external computer 470. Upon receiving such changes, the algorithms of the app 474 re-compute conclusions based upon previous inputs that have not changed, and the new information inputted by the user. New results from the re-computations are displayed at 492 and the user can again review the results. This process can iterate until the user is satisfied with the results/suggestions display by the app 474. Changes may be made by the user in regard to any of the variables described above with regard to conclusions that have been outputted. Additionally, or alternatively, the user may need to update user-entered inputs, such as baby's weight and/or other food intake, for example.

Figure 32:
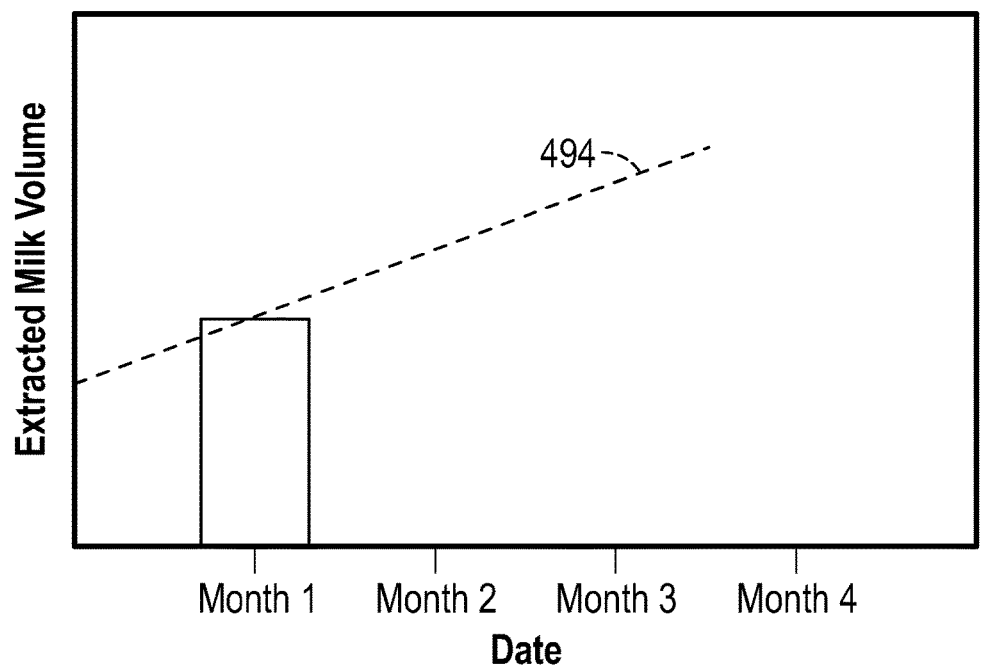
FIG. 32 illustrates a histogram displaying expected breast milk extraction volumes, according to an embodiment of the present disclosure.

Based upon the inputs received, one of the outputs that the app 474 can calculate and display is an expected breast volume extraction per breast pumping session, relative to the age and/or weight of the baby, relative to the age of the baby, as illustrate as 494 in FIG. 32. This expected volume may be based on previous breast extraction volumes from previous sessions, and/or national averages relative to age and/or weight. The expected volume curve may also be modified by goal inputs of the user. For example, if the user wants to increase production, the curve 494 may be somewhat steeper than it otherwise would be. Likewise, for a weaning goal, the curve 494 would have a downward slope at some time period and then continue moving downward.

The expected volume input can be sent to the controller(s) 52 either by wire or wirelessly. Given the responsive nature of the system 100, through the pressure readings feedback as described above, during a milk extraction session the system controller(s) 52 can keep track of the total volume of milk that has been expressed. As the total milk volume expressed reaches the desired volume indicated by curve 494, the controller 52 can automatically cease pumping action and end the pumping session. Likewise, if the expected total volume of expressed milk has not been achieved after the expected of a pumping session, the controller(s) can continue to pump until the expected total volume has been achieved, or for a predetermined time period e.g., one minute, two minutes, five minutes, ten minutes, or some other predetermined time period, which may be set by the app 474, or specified by the user input to the app 474) after the expected end time of the current pumping session.

In addition to expected expressed milk volume data, the external computer 470 can execute the app 474 to send information to the controller(s) 52 to instruct specific pumping modes to use at specific times (or other thresholds, such as when a predetermined volume has been achieved, etc.) during a pumping session. The modes that are instructed for execution may also be influenced by the user's inputted goals. As one example, if the user is a new mother whose baby is in the NICU, and the mother is just beginning to try and express milk using the system 100, app 474 may instruct the controller(s) 52 to execute a more gentle pumping cycle than that used for maintenance or building goals. Additionally, in this mode, the controller(s) will not shut down the pumping operation as readily, as it will be expected that less milk will be extracted by the new mother and that it may take a longer time, with less flow. Accordingly, the more gentle cycle may be continued for a longer period before shutdown, and the milk flow threshold for shutdown will be much lower.

The software for executing the pumping modes can be uploaded from the app 474 along with the instructions resulting from processing the user-entered inputs and measured inputs. Preferably, however, the pumping modes are already contained in firmware on the controller(2) 52 so the external computer 470 (via app 474) only needs to input specific data that effects running of the particular modes, such a mode selection, mode selection times or other parameters for switching modes, expected milk expression volume, etc. It is also noted here that mode selection by the controller(s) 52, as executed according to instructions received by the app 474, can be overridden by the user at any time using the controls 153 (see FIG. 26), and any other changes, such as pump frequency, maximum suction pressure; latch suction pressure, etc., can also be manually overridden by the user with controls 153.

In addition to sending data to the controller(s) for use in operations during pumping sessions, and displaying data for use and interaction by the user, data may be sent from app 474, restricted sets of data can be sent to the user's health care provider and/or health insurance carrier (e.g., by transmission over the Internet, or other transmission means). The data that is sendable to the healthcare provider may be the same or different from the data that is sent to the health insurance carrier, as the data sent to the health insurance carrier may be more restrictive than what is sent to the healthcare provided. The data that is sendable to the healthcare provider may be restricted, such that certain data that is identified as private is not sent, or all data that is available to the user may be sent to the healthcare provider. Information that is sendable to the health insurance provider will generally include at least data about how often the system 100 is used by the user, as the health insurance provider may require a minimum amount of use in order for the costs of the system 100 to be covered (or partially covered) by health insurance reimbursement. All or a portion of the data provided by app 474 can also be exported by a social media format for use in various other community help purposes.

Figure 33:
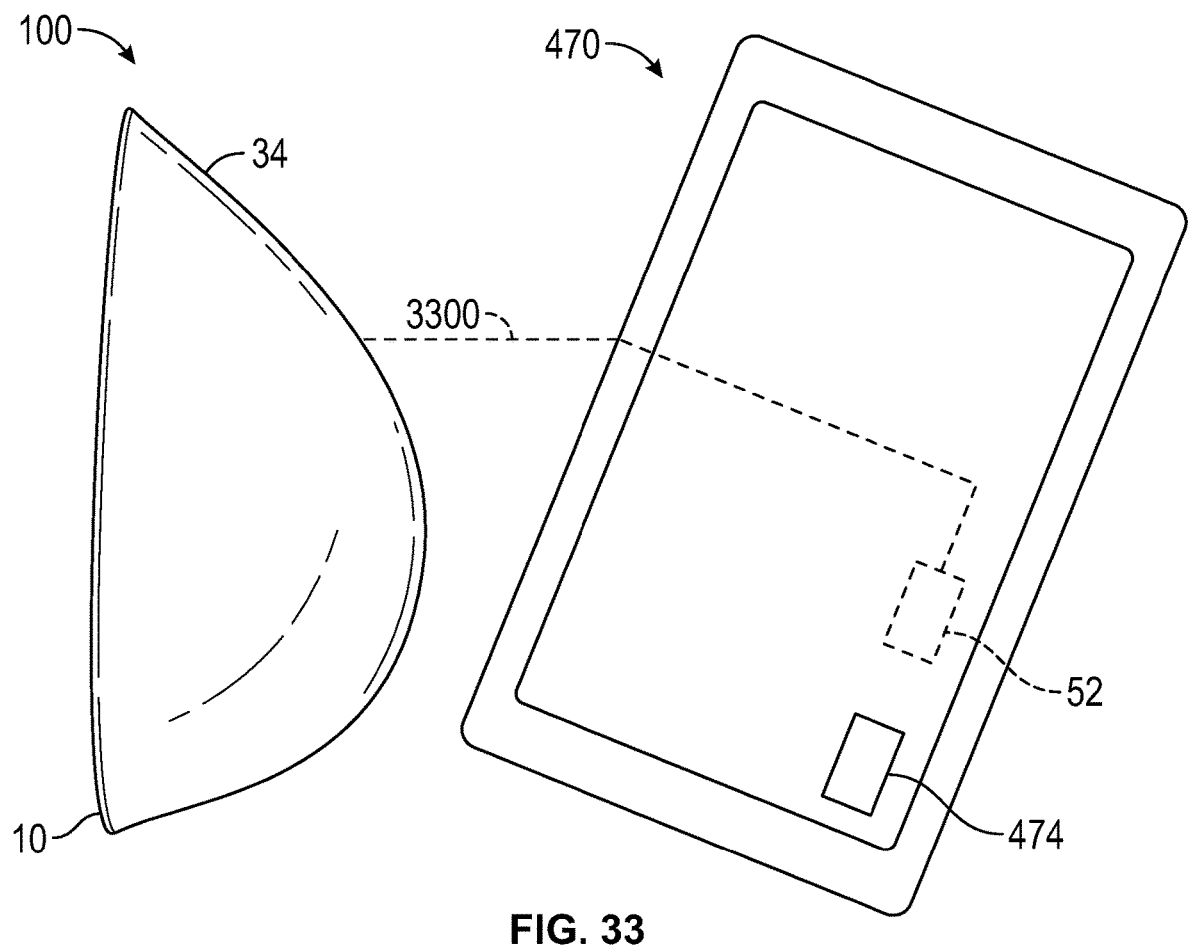
FIG. 33 illustrates a breast pump system according to an embodiment of the present disclosure, in which the controller is provided in an external computer, according to an embodiment of the present disclosure.

FIG. 33 illustrates a breast pump system according to an embodiment of the present disclosure, in which controller 52 is provided in the external computer 470. In this embodiment, all of the control functions of controller 52, as described above, are carried out in the external computer 470, rather than in the main body 34. The real-time control and feedback is the same as in embodiments where controller 52 is located in the main body 34 of the device, but the control signals are outputted, and feedback is received by the controller at the location of the external computer, where the signals are transmitted either wirelessly (by Bluetooth, or other radio transmission or wireless transmission protocol) or, optionally, by a wire or cable connection 3300. Further optionally, in embodiments where the wired connection 3300 is provided, battery 48 can be eliminated from the main body 34 of the device, and power to operate all components of the device can be transmitted over the wire connection 3300 from external computer 470, which may be battery-powered, or connected to AC power.

An infant's supply needs as to the volume of milk that needs to be consumed per day grows as the baby grows and gets older. The breasts 2 of the mother respond to this growing need by increasing milk production as the needs increase. Currently known pumping systems do not actively take into account these growing needs, as they operate in the same manner regardless of the age and size of the baby being fed. The present disclosure offers at least one "build" mode that can be selected by a user to stimulate increasing production by the breasts 2. As the system 100 is responsive to the expression of milk during a pumping session, while pumping in a build mode, the system 100 may sense that the milk volume flow (and/or total volume expressed at a particular time) is on track for the average production to date by the mother, but, in order to stimulate increase in production, the system 100 can increase, in real-time, the time period over which the pump holds maximum suction pressure per cycle, or the maximum suction pressure level achieved, or both, or provide other modifications to the current pumping cycle to try and achieve an even greater expression of milk. This simulates a breastfeeding baby that works harder (harder and/or longer sucks) to try and draw more milk from the mother's breast 2, or a baby that just consumes more milk from the breast 2 for a longer period of time, because of its increasing needs due to growth. As the feedback can be provided continuously or from cycle-to-cycle, the controller 52 can assess in real time which changes are being effective, if any, in increasing the amount of milk extracted, and make further modifications, or maintain successful modifications, going forward with pumping cycles.

When executing a maintenance mode, the controller 52 executes the mode as instructed by the app 474 (or user, via manual mode selection on the device) with parameters of suction and suction holding times being maintained if sufficient milk flow feedback is received, and with the pumping session ended when the expected milk expression volume has been achieved. Similarly, in weaning mode, the controller 52 executes the mode as instructed by the app 474 (or user, via manual mode selection on the device) with parameters of suction and/or suction holding times being generally less than in maintenance mode, which helps to signal the breast 2 and the mother's brain to begin reducing milk production. A maximum pump mode may be provided that is designed to extract the most volume of milk possible within a predetermined time period, for example, when the mother has only a limited amount of time to pump. In this mode, the maximum suction, latch suction, and suction hold periods are designed to maximize the milk extraction within a predefined time period, which can be inputted by the user through user inputs 490 or through controls 153. This mode may not be optimal for overall total volume of milk extracted when a more extensive time period is available, but it is optimized for the time period selected. In any of these modes, the system 100 can alter suction levels (maximum and or latch), hold times, pause times, cycle frequency, etc., based on feedback received by the controller 52.

Figure 34:
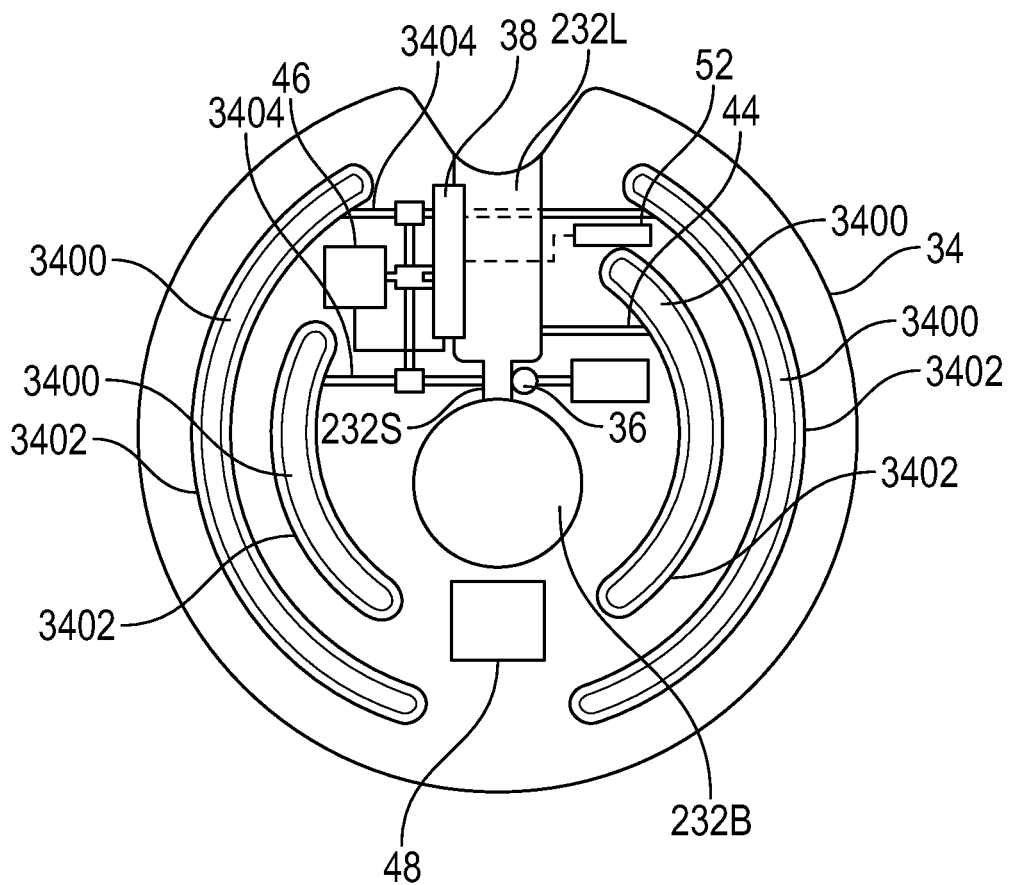
FIG. 34 illustrates a system that includes vibration members, according to an embodiment of the present disclosure.

FIG. 34 is a schematic illustration of a distal end view of a pumping device, with the subassembly 35 having been removed so as to show the channel portions 232L, 232S and 232B that the conduit portions 32L and 32S and the segment 16 fit into when subassembly 35 is assembled into the main body 34, according to an embodiment of the present disclosure. In this embodiment, vibration members 3400 are provided in channels 3402 and configured for rapid back and forth movement (in and out of the page, as shown in FIG. 34) driven by drive trains 3404 connecting the vibration members 3400 to motor 46, so that when motor 46 is operated to drive the compression member 38 back and forth, it also drives the vibration members 3400 in and out. When the system 100 is installed on the breast 2 for operation in a milk extraction session, operation of motor 46, not only drives compression member 38, but also drives vibration members 3400 to oscillate into and away from the breast 2. This vibratory contact can further facilitate milk extraction (including stimulation of the nipple 3 and areola regions of the breast 2), and can also stimulate the breast 2 and mother's brain to condition them to produce greater total milk extraction volumes for future pumping sessions. Alternatively, or additionally, the system 100 may be configured to apply heat to the breast 2 to facilitate maximization of milk volume expressed and/or to add comfort to the user.

Figure 35:
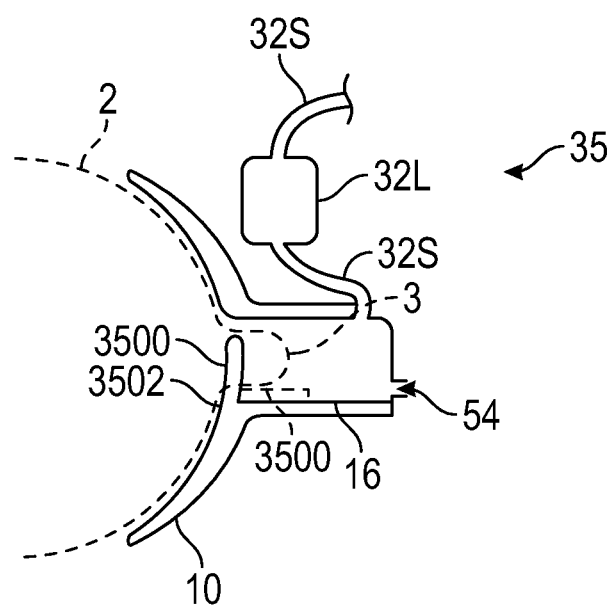
FIG. 35 illustrates a subassembly according to another embodiment of the present disclosure.

FIG. 35 illustrates subassembly 35 according to another embodiment of the present disclosure. In this embodiment, the entrance opening to segment 16 is at least partially blocked (greater than 50% of the opening, more preferably in the range of 60 to 100%, even more preferably in the range of 75% to 100%) by gate 3500. Gate 3500 includes a living hinge 3502 configured such that, when the system is installed on the breast 2, as breast 2 contacts the skin contact member 10, nipple 3 protrudes past the gate 3500, thereby bending gate 3500 down against the lower wall of the segment 16 as illustrated in phantom in FIG. 35. Upon finishing the pumping session, as the system is removed the breast 2, the gate 3500 returns to its initial, closed orientation shown in solid lines. Thus, if there is milk remaining in segment 16 upon detachment of the system 100 from the breast 2, most if not all of this milk will be prevented from spilling out of the segment 16 by gate 3500.

Figure 36:
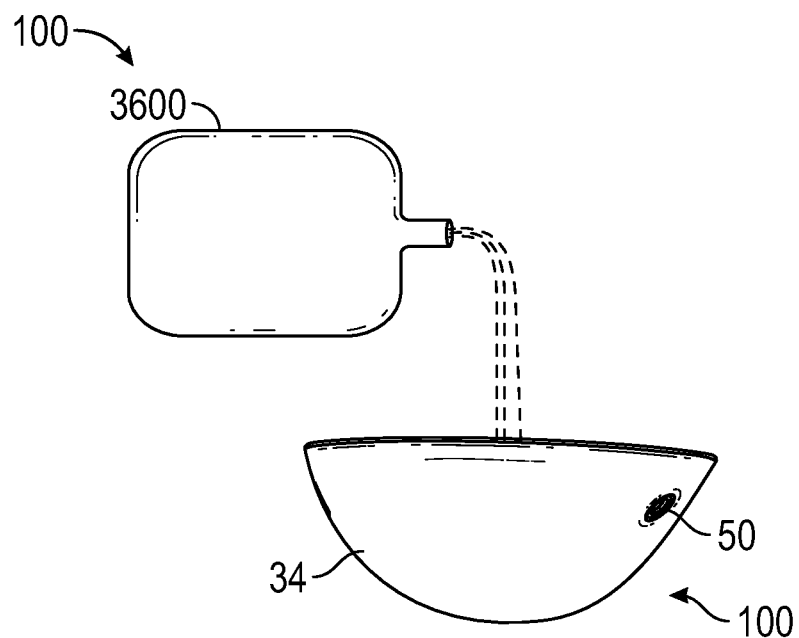
FIG. 36 illustrates cleaning fluid being administered to the interior surfaces of a skin contact member and conduit, according to an embodiment of the present disclosure.

FIG. 36 illustrates a method of cleaning the subassembly 35 without removing it from the system. In this embodiment, cleaning fluid, such as soapy water or other specially formulated cleaning fluid can be dumped from a container 3600 (or other source of cleaning fluid/soapy water) into the segment 16 and the pumping section 30 can be actuated to pump the cleaning fluid through the conduit 32 and out of one-way valve 50. After running the cleaning fluid/soapy water through the system 100, pure water, saline, or other rinsing agent can be pumped through the conduit 32 in the same manner. This cleaning action can be performed using any pumping mode, as desired. Alternatively, a mode designed specifically cleaning may be available for selection by the user.

Figure 37:
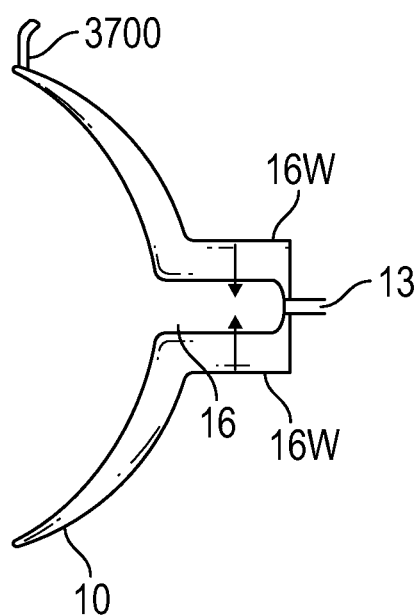
FIG. 37 is a partial view of a subassembly according to another embodiment of the present disclosure.

FIG. 37 is a partial view of subassembly 35 according to another embodiment of the present disclosure. In this embodiment, the side walls 16W are collapsible under some predefined suction pressure greater than maximum suction operating pressures to be used during pumping. For example, walls 16W may be configured to collapse at suction pressures in the range of −240 mm Hg to −250 mm Hg, or −220 mmHg to −240 mmHg, or some other predetermined suction pressure greater than maximum operating suction pressure. In this way, the walls 16W do not collapse during the pumping session. However, when milk pumping is determined to have been completed, just prior to shutting down the pumping section 30, the controller 52 operates the pumping section 30 to gradually increase maximum suction pressures, to collapse the walls 16w down to the nipple 3, thereby sucking substantially all remaining milk out of the segment 16. Alternatively, the collapsible region of the walls 16W can be made to collapse proximally of the nipple 3, but not against the nipple 3. Next the compression member 36 maintains the tubing section 32S closed and the pumping section (motors 44, 46) is shut down and the system 100 can be removed from the breast with little risk of milk spillage, since there will be substantially no milk left distally of the compression member 36. Upon breaking the suction seal between the system 100 and the breast 2, the walls 16W resiliently return to their original, non-collapsed configurations shown in FIG. 37. Optionally, a tab 3700 or other member can be provided on the skin contact member 10, which can be manually pulled to facilitate a small break in the suction seal to make it easier to remove the system 100 from the breast 2.

Figure 38:
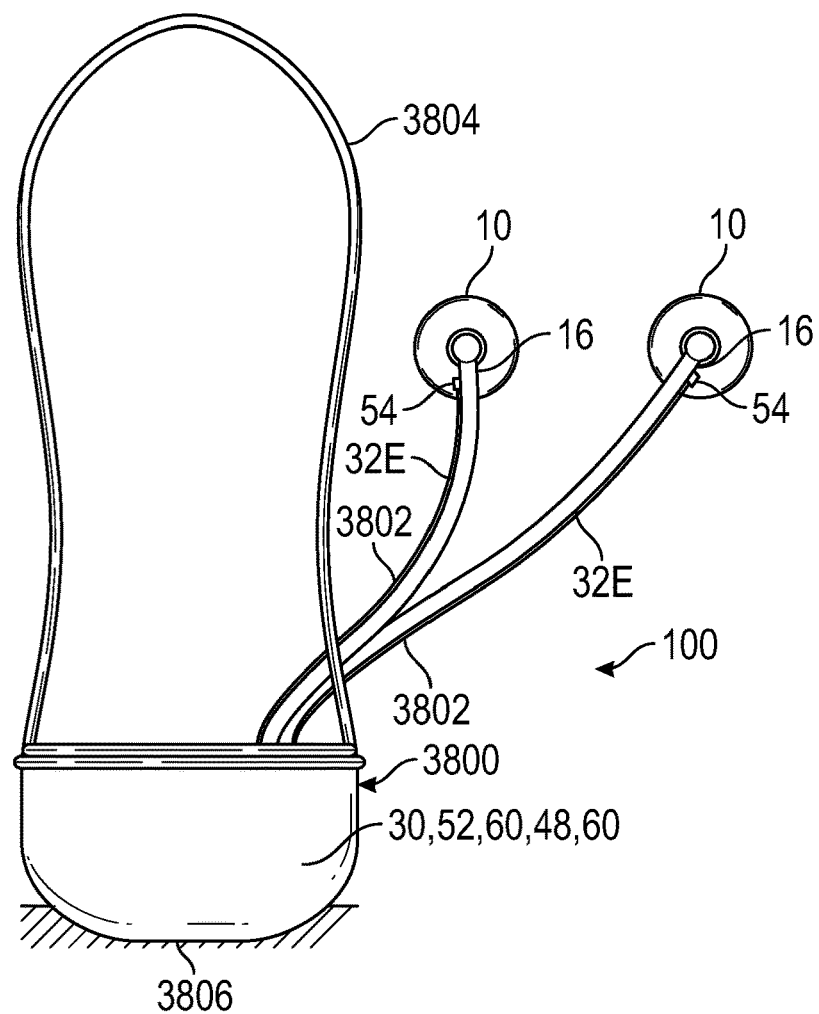
FIG. 38 illustrates a breast pump system according to another embodiment of the present disclosure.

FIG. 38 illustrates a breast pump system 100 according to another embodiment of the present disclosure. In this embodiment, rather than being included in a device that mounts to the breast 2, the pumping section 30, conduits 32S, 32L, battery 48, controller 52, one way valve 50 and milk collection container 60 are all contained within a purse, satchel or other bag or container 3800 designed and dimensioned to support these components. Container 3800 can be supported by the user with a shoulder strap 3804 configured and dimensioned to be worn over the shoulder of the user, or, can alternatively be supported on an external surface 3806 such as a table, chair, desk, bed, or the like. In the embodiment shown, the skin contact members 10 are attached to the breasts 2 in the same manner as previously described embodiments, and are connected to the pumping section via conduits 32E that are less compliant than the conduit sections 32S, 32L, and are preferably made as rigid as is practical. Pressure sensor 54 is provided in or near segment 16 located at the proximal end portion of skin contact member 10. Alternatively, pressure sensors could be located on the conduit 32 in the container 3800, such as adjacent segment 40/32S. The conduits 32E can be connected to a single pumping section 30 via conduit portions 32S and 32L, or may be each connected to its own dedicated pumping section 30 and conduit portions 32S and 32L, for more individualized control over the pumping operations on each breast 2.

Figure 39:
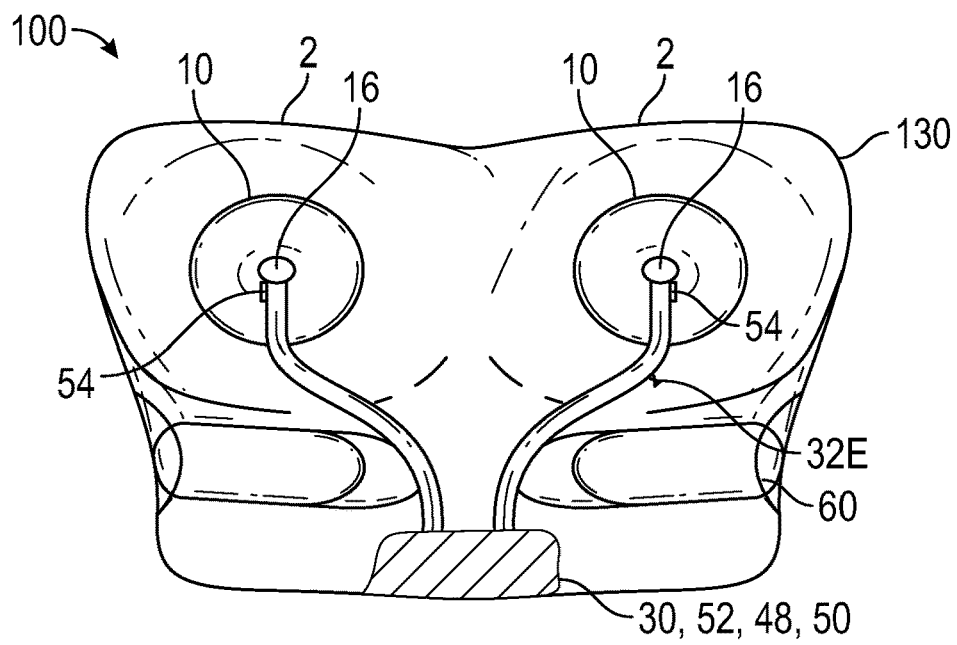
FIG. 39 illustrates a breast pump system according to another embodiment of the present disclosure.

FIG. 39 illustrates a breast pump system 100 according to another embodiment of the present disclosure. In this embodiment, like in the embodiment of FIG. 38, rather than being included in a device that mounts to the breast 2, the pumping section 30, conduits 32S, 32L, battery 48, controller 52, one way valve 50 and milk collection container 60 are all mounted on a lower section of bra 130, below the breasts 2. In the embodiment shown, the skin contact members 10 are attached to the breasts 2 in the same manner as previously described embodiments, and are connected to the pumping section via conduits 32E that are less compliant than the conduit sections 32S, 32L, and are preferably made as rigid as is practical. Pressure sensor 54 is provided in or near segment 16 located at the proximal end portion of skin contact member 10. Alternatively, pressure sensors could be located on the conduit 32 in pumping section 30, such as adjacent segment 40/32S. The conduits 32E can be connected to a single pumping section 30 via conduit portions 32S and 32L, or may be each connected to its own dedicated pumping section 30 and conduit portions 32S and 32L, for more individualized control over the pumping operations on each breast 2.

Figure 40:
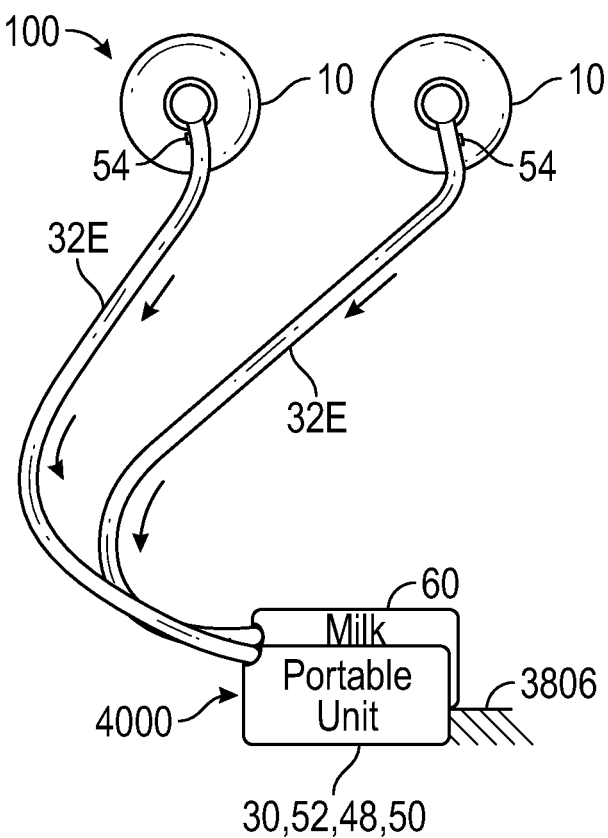
FIG. 40 illustrates a breast pump system according to another embodiment of the present disclosure.

FIG. 40 illustrates a breast pump system 100 according to another embodiment of the present disclosure. In this embodiment, rather than being included in a device that mounts to the breast 2, the pumping section 30, conduits 32S, 32L, battery 48, controller 52 and one way valve 50 are all contained within a portable unit 4000 alongside a milk collection container 60. Portable unit 4000 can be readily hand carried by the user or placed in a purse, bag or other container 3800 or, can be supported on an external surface 3806 such as a table, chair, desk, bed, or the like. In the embodiment shown, the skin contact members 10 are attached to the breasts 2 in the same manner as previously described embodiments, and are connected to the pumping section via conduits 32E that are less compliant than the conduit sections 32S, 32L, and are preferably made as rigid as is practical. Pressure sensor 54 is provided in or near segment 16 located at the proximal end portion of skin contact member 10. Alternatively, pressure sensors could be located on the conduit 32 in the portable unit 4000, such as adjacent segment 40/32S. The conduits 32E can be connected to a singled pumping section 30 via conduit portions 32S and 32L, or may be each connected to its own dedicated pumping section 30 and conduit portions 32S and 32L, for more individualized control over the pumping operations on each breast 2.

Figure 41:
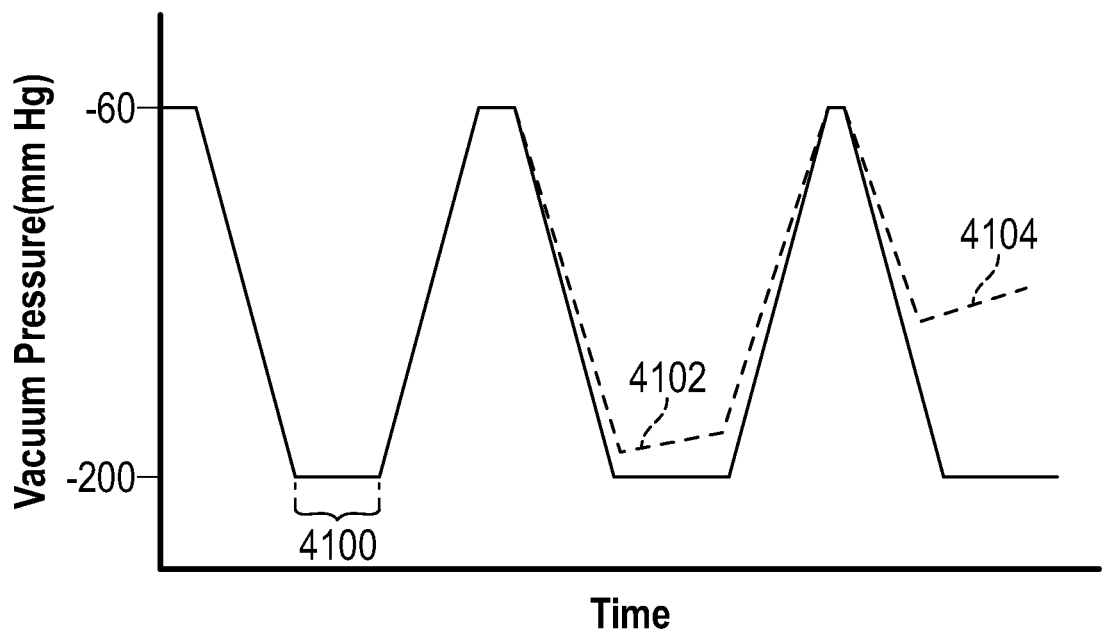
FIG. 41 illustrates one example of a pressure waveform used in one pumping mode of a system according to an embodiment of the present disclosure.

The responsive nature of the present systems 100 enables the systems to maintain a desired pressure waveform over repeated pumping cycles even as the milk volume within the conduit 32 varies. FIG. 41 illustrates one example of a pressure waveform 4100 used in one pumping mode of the system according to an embodiment of the present disclosure. In this embodiment, the pressure waveform moves from a latch suction pressure of −60 mm Hg to a maximum suction pressure of −200 mm Hg, over a hold period 4100 during which the maximum suction pressure is maintained, and back to the latch suction pressure of −60 mm Hg. As milk enters the system, the more that the conduit 32 fills up with milk, the more the suction will "bleed off" in the conduit. For example, the phantom lines 4102 and 4104 illustrate how the suction pressure becomes less than maximum suction pressure and continues to decrease (relatively higher pressure) as the milk continues to take up more and more volume of the conduit 32. The phantom lines are the result if the pumping mechanism is not responsive and just carries on with the same pumping parameters (stroke, force and timing) with each succeeding cycle. However, by receiving feedback from sensor 54, controller 52 can modify the pumping parameters in real time, so as to maintain each cycle of the pumping cycle as it should be, i.e., following the solid lines in the waveform in FIG. 41. This can be achieved, for example, by increasing the stroke of the compression member 38 until the maximum suction level is achieved, and then modifying the position of compression member 38 as needed during the hold period 4100 to maintain the maximum suction pressure over the course of the holding period. This same type of responsivity can be applied in real time, over the extent of the entire pumping cycle so as to maintain a desired pumping profile cycle after cycle.

As the system 100 is being operated, the user has the ability to manually change operating parameters such as maximum suction pressure, latch suction pressure, hold times, pause time, etc. Controller 52 may be programmed to monitor manual changes made by the user during use, and to save these changes in memory and apply the changes automatically the next time the user uses the same pumping mode that was modified previously. Over a series of uses of any given pumping mode, the controller 52 (and/or app 474) may compare pumping results (e.g., milk extraction volume) for the various changes in pumping parameters made by the user over multiple sessions, identify those changes that produced the greatest milk extraction results, save those changes that produce the best results, and apply those changes in the next pumping session using the same pumping mode. In this way the system "learns" more efficient pumping parameters for application to a specific individual user.

Other pumping modes may be programmed in an effort to simulate an actual baby breastfeeding from the breast 2. Examples of such modes include pumping modes that don't simply repeat the same suction pressures and hold periods cycle after cycle, but vary them in ways attempted to change in the way a baby changes suckling patterns during breastfeeding. Other modes that can be provided include a mode that simulates an active, aggressive feeder and a made that simulates a sleepy, slow feeder, where the active mode could achieve a higher maximum suction level and/or longer hold periods at maximum suction level compared to a standard pumping mode (e.g., maintenance mode) and the sleepy mode could be set for lower maximum suction level and or shorter hold periods at maximum suction level compared to a standard pumping mode such as maintenance mode. Other profiles could be provide as modes that the user could select from to attempt a breast pumping session that is most closely matched to a manner in which her baby breastfeeds, such as a frequent pauser mode, wherein pauses in the pumping action are more frequent and/or longer than those provided in a more standard mode.

Figure 42:
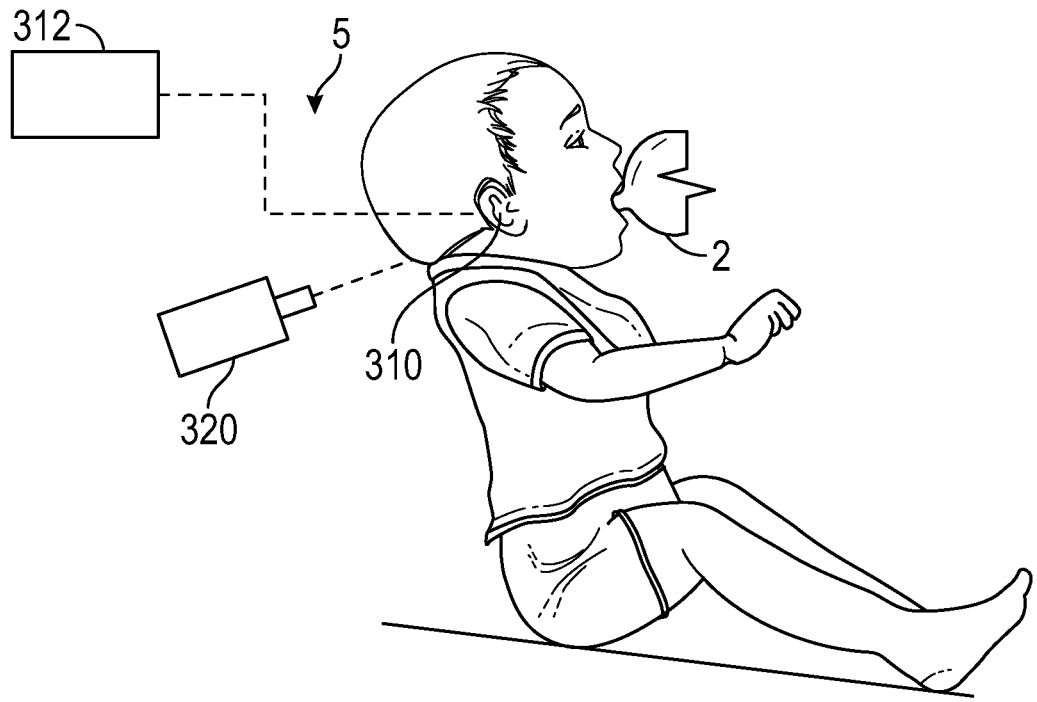
FIG. 42 illustrates a method of monitoring a baby's feeding style during breastfeeding, according to an embodiment of the present disclosure.

FIG. 42 illustrates a method of monitoring a baby's feeding style during breastfeeding, according to an embodiment of the present disclosure. In this embodiment, a microphone 310 is adhered to or placed against the throat of the baby 5 and swallow sounds are recorded. By recording and differentiating between the sounds that vary for a swallow full of milk and a swallow empty of milk, as well as swallows having intermediate amounts somewhere in between full and empty, and the time periods between swallows, this data can be inputted to app 474 (or controller 52) and used to derive a pumping mode that cycles according to the timing of swallows performed by the baby 5 during the actual breastfeeding. Sucking sounds may also be recorded to differentiate between hold periods at maximum suction and pause periods during which only latch suction is applied to the breast when operating the system in this baby mode. Additionally, a camera 320 can optionally be provided to view the throat as the baby 5 swallows, as an aid to counting the number of swallows during the feeding session. Otherwise the number of swallows can be audibly determined using the microphone 310 (and associated amplifier and recording equipment 312, types of which are known in the art).

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the present disclosure as described herein.

That which is claimed is:

1. An automated breast pump system for controlling a pumping cycle to pump milk from a breast of a user, the system comprising:
    a control system capable of sensing and controlling suction pressure waveforms to optimize filling milk ducts of a user during minimum suction and optimize extraction during increased suction greater than the minimum suction;
    a breast pump housing sized and shaped to fit within a bra;
    a breast adapter configured and dimensioned to form a seal with the breast;
    a storage container for storing the milk pumped from the breast;
    a compression member;
    a conduit configured within the breast pump housing and in fluid communication with, and interconnecting the breast adapter and the storage container, the conduit configured to provide an upward milk flow path within the breast pump housing from the breast adapter to the storage container when the automated breast pump system is in use and engaged with the breast, the conduit including features for attaching to the compression member; and
    at least one driver responsive to the control system;
    wherein the compression member is attached to the conduit and configured to compress the conduit to a compressed configuration where the compression member is attached to the conduit and to apply a pulling force to where the compression member is attached to the conduit to expand the conduit from the compressed configuration in response to the at least one driver; and
    wherein natural physiology of producing milk is facilitated and wherein each of at least a portion of the breast adapter, the compression member, the conduit and the at least one driver are contained within the breast pump housing, the conduit and compression member being arranged above the at least a portion of the breast adapter contained within the breast pump housing when the breast pump housing is placed for use within the bra.

2. The system of claim 1, further comprising a second automated breast pump system, wherein pumping of the milk from a first breast is coordinated with pumping of milk from a second breast.

3. The system of claim 1, further comprising undercuts or notches formed in the conduit to facilitate expansion of the conduit.

4. The system of claim 1, further comprising a controller configured to generate a histogram reflecting pumping action.

5. The system of claim 1, wherein suction applied to the breast for expression of the milk comprises a first suction level, and wherein, during expulsing, a second suction level is maintained against the breast, the second suction level being lower than the first suction level, wherein the second suction level is a latch suction which is maintained throughout a pumping session.

6. The system of claim 1, further comprising a battery and a controller monitoring the battery.

7. The system of claim 1, further comprising a sensor that senses flow rate.

8. The system of claim 1, further comprising a display configured to display an image of a baby or project recorded sounds of the baby.

9. The system of claim 1, further comprising a motor and a sensor for tracking a position of the motor.

10. The system of claim 1, further comprising a controller configured to track inventory.

11. The system of claim 1, further comprising a controller configured to track dates of extracted milk.

12. The system of claim 1, further comprising a controller, wherein the controller adaptively controls one or more of maximum suction pressure level, latch suction pressure level, the suction pressure waveform over the pumping cycle, phases of extraction or feeding times, rest times, heating temperatures and times, vibration frequency and duration, and pumping session time.

13. The system of claim 1, further comprising a controller, wherein the controller controls one or more of pumping mode; frequency of the pumping cycle, maximum suction pressure achieved during the pumping cycle; latch suction pressure achieved during the pumping cycle, pumping force and pumping session time.

14. The system of claim 1, wherein the conduit includes a non-circular region.

15. The system of claim 1, the conduit includes opposing flat sections.

16. The system of claim 1, further comprising a contouring shell configured to provide an appearance of a natural breast contour when the breast adapter is sealed to the breast.

17. The system of claim 1, further comprising a controller, wherein the controller provides or controls one or more of a sleep mode, pumping goals, tracking of efficiency, weaning modes, growing modes, communication with health care providers, maintenance modes, and maximum pump modes.

18. The system of claim 1, wherein walls of the conduit are collapsible to suck remaining milk out of the conduit.

19. The system of claim 1, further comprising one or more controllers, wherein one or more controllers control pumping to match desired suction pressure waveforms.

20. The system of claim 1, further comprising a motor and a sensor, wherein feedback from the sensor is communicated to the control system to control pumping.

21. The system of claim 20, further comprising an encoder mounted to the motor.

22. The system of claim 21, wherein the motor is configured to rotate and the encoder rotates with the motor.

23. The system of claim 21, further comprising an optical monitor configured to observe the encoder.

24. The system of claim 23, wherein the optical monitor is beamed against the encoder and the beam is reflected to the sensor.

25. The system of claim 1, further comprising a motor and a sensor, wherein the sensor communicates with the control system.

26. The system of claim 25, wherein the control system includes a controller that cooperates with the sensor to calculate a position of the motor.

27. The system of claim 26, wherein the controller calculates a position of the compression member that is driven by the motor.

28. The system of claim 27, wherein the position of the compression member is calculated relative to a reference or starting position of the compression member.

* * * * *